US009554995B2

(12) United States Patent
Middelberg et al.

(10) Patent No.: US 9,554,995 B2
(45) Date of Patent: Jan. 31, 2017

(54) NANOEMULSIONS

(71) Applicant: THE UNIVERSITY OF QUEENSLAND, St. Lucia, Queensland (AU)

(72) Inventors: Anton Peter Jacob Middelberg, Brookfield (AU); Bijun Zeng, Forest Lake (AU)

(73) Assignee: The University of Queensland, St. Lucia (AU)

( * ) Notice: Subject to any disclaimer, the term of this patent is extended or adjusted under 35 U.S.C. 154(b) by 0 days.

(21) Appl. No.: 14/407,819

(22) PCT Filed: Jun. 13, 2013

(86) PCT No.: PCT/AU2013/000630
§ 371 (c)(1),
(2) Date: Dec. 12, 2014

(87) PCT Pub. No.: WO2013/185178
PCT Pub. Date: Dec. 19, 2013

(65) Prior Publication Data
US 2015/0132395 A1    May 14, 2015

(30) Foreign Application Priority Data

Jun. 13, 2012  (AU) .................................. 2012902471

(51) Int. Cl.
| A61K 9/107 | (2006.01) |
| C07K 7/06 | (2006.01) |
| C07K 7/08 | (2006.01) |
| C07K 14/00 | (2006.01) |
| A61K 39/39 | (2006.01) |
| A61K 47/48 | (2006.01) |
| C07K 16/28 | (2006.01) |
| A61K 38/00 | (2006.01) |
| A61K 39/00 | (2006.01) |

(52) U.S. Cl.
CPC ............. *A61K 9/107* (2013.01); *A61K 9/1075* (2013.01); *A61K 39/39* (2013.01); *A61K 47/488* (2013.01); *A61K 47/48561* (2013.01); *C07K 7/06* (2013.01); *C07K 7/08* (2013.01); *C07K 14/00* (2013.01); *C07K 14/001* (2013.01); *C07K 16/2851* (2013.01); *A61K 38/00* (2013.01); *A61K 2039/55516* (2013.01); *A61K 2039/55566* (2013.01); *C07K 2319/33* (2013.01)

(58) Field of Classification Search
None
See application file for complete search history.

(56) References Cited

U.S. PATENT DOCUMENTS

| 5,330,682 | A | 7/1994 | Brock et al. |
| 2010/0152420 | A1 | 6/2010 | Middelberg et al. |
| 2010/0172943 | A1 | 7/2010 | Edelson et al. |
| 2012/0003277 | A1 | 1/2012 | Baker et al. |
| 2012/0046444 | A1 | 2/2012 | Middelberg et al. |
| 2013/0085188 | A1 | 4/2013 | Middelberg et al. |
| 2013/0121917 | A1 | 5/2013 | Xu et al. |
| 2013/0251629 | A1 | 9/2013 | Delmas et al. |
| 2016/0009770 | A1 | 1/2016 | Xu et al. |

FOREIGN PATENT DOCUMENTS

| WO | 89/04209 | 5/1989 |
| WO | 2006/089364 | 8/2006 |
| WO | WO 2008/140594 | 11/2008 |
| WO | 2011/101602 | 8/2011 |
| WO | 2011/112999 | 9/2011 |
| WO | WO/2012/079125 | * 6/2012 |

OTHER PUBLICATIONS

Chuan et al. "Co-delivery of antigen and a lipophilic anti-inflammatory drug to cells via a tailorable nanocarrier emulsion," Journal of Colloid and Interface Science 368 (2012) 616-624, available online Nov. 22, 2011.*
Middelberg et al. "A Designed Biosurfactant Protein for Switchable Foam Control," ChemPhysChem 2011, 12, 1426-1429.*
Azeem et al. "Nanoemulsion Components Screening and Selection: a Technical Note," AAPS PharmSciTech, vol. 10, No. 1, Mar. 2009.*
Hak et al. "The Effect of Nanoparticle Polyethylene Glycol Surface Density on Ligand-Directed Tumor Targeting Studied in Vivo by Dual Modality Imaging," ACSNANO, 2012, vol. 6, No. 6, 5648-5658, published online Jun. 6, 2012.*
Ge et al. "The antitumor immune responses induced by nanoemulsionencapsulated MAGE1-HSP70/SEA complex protein vaccine following different administration routes," Oncology Reports 22: 915-920, 2009.*
International Search Report for PCT/AU2013/000630, mailed Jul. 31, 2013, 5 pages.
International Preliminary Report on Patentability dated Dec. 24, 2014 from PCT/AU2013/000630.

(Continued)

*Primary Examiner* — Christina Bradley
(74) *Attorney, Agent, or Firm* — Nixon & Vanderhye PC

(57) ABSTRACT

The invention relates to nanoemulsions useful for analytical techniques and delivery of cargoes such as pharmaceutically active agents. In particular, the invention relates to nanoemulsions comprising an oil phase dispersed in an aqueous phase and at least two peptide surfactants adsorbed at the liquid-liquid interface, one peptide surfactant comprising a short peptide sequence having α-helical propensity and at least one second polypeptide surfactant comprising at least two peptide sequences having α-helical propensity linked by a linking sequence of 3 to 11 amino acid residues. Optionally the at least one second polypeptide surfactant comprises at least one pharmacokinetic modifying agent and/or a targeting agent. Furthermore, the nanoemulsion may further comprise a cargo such as a pharmaceutically active agent.

25 Claims, 10 Drawing Sheets

(56) References Cited

OTHER PUBLICATIONS

Dwyer et al. "Insights into the role of protein molecule size and structure on interfacial properties using designed sequences" *Macromolecules*, 10:1-11 (Jan. 2013).
Chuan et al. "Co-delivery of antigen and a lipophilic anti-inflammatory drug to cells via a tailorable nanocarrier emulsion" *J Colloid Interface Sci*, 368:616-624 (Nov. 2011).
Neelesh et al. "Molecularly targeted nanocarriers deliver the cytolytic peptide melittin specifically to tumor cells in mice, reducing tumor growth" *J Clin Invest*, 119:2830-2842 (Sep. 2009).
Sainsbury et al. "Towards designer nanoemulsions for precision delivery of therapeutics" *Curr Opn Chem Eng*, 4:11-17 (May 2014).
Zeng *Tailorable Nanocarrier Emulsion for Drug Delivery* PhD thesis submitted to Australian Institute for Bioengineering and Nanotechnology at The University of Queensland, retrieved from URL:https://espace.library.uq.edu.au/view/UQ:350657/s4070039_phd_submission.pdf, pp. 1-185 (Jan. 2014).
Zeng et al. "Receptor-specific delivery of protein antigen to dendritic cells by a nanoemulsion formed using top-down non-covalent click self-assembly" *Small*, 9:3736-3742 (Nov. 2013).
Written Opinion of ISA for PCT/AU2013/000630, three pages, dated Jul. 31, 2013.
EPO supplementary search report for related European Appln 13804554, six pages, dated Apr. 5, 2016.

\* cited by examiner a

CHO-K1 to CHO-K1-Clec9A
1:1 b

CHO-K1 to CHO-K1-Clec9A
1:10

SEQUENCE LISTING

<160> NUMBER OF SEQ ID NOS: 67

<210> SEQ ID NO 1
<211> LENGTH: 21

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: acetylmethionine
<220> FEATURE:
<221> NAME/KEY: MISC_FEATURE
<222> LOCATION: (21)..(21)
<223> OTHER INFORMATION: alanine amide

<400> SEQUENCE: 1

Xaa Lys Gln Leu Ala Asp Ser Leu His Gln Leu Ala Arg Gln Val Ser
 1               5                  10                  15

Arg Leu Glu His Xaa
            20

<210> SEQ ID NO 2
<211> LENGTH: 24
<212> TYPE: PRT
<213> ORGANISM: Artificial Sequence
<220> FEATURE:
<223> OTHER INFORMATION: Synthetic

<400> SEQUENCE: 2

Pro Ser Met Lys Gln Leu Ala Asp Ser Leu His Gln Leu Ala Arg Gln
 1               5                  10                  15

Val Ser Arg Leu Glu His Ala Asp
            20

<210> SEQ ID NO 3
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylmethionine
<220> FEATURE:
<221> NAME/KEY: MISC_FEATURE
<222> LOCATION: (21)..(21)
<223> OTHER INFORMATION: Alanine amide

<400> SEQUENCE: 3

Xaa Lys Gln Leu Ala Asp Ser Leu Met Gln Leu Ala Arg Gln Val Ser
 1               5                  10                  15

Arg Leu Glu Ser Xaa
            20

<210> SEQ ID NO 4
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetyl leucine
<220> FEATURE:
<221> NAME/KEY: MISC_FEATURE
<222> LOCATION: (28)..(28)
<223> OTHER INFORMATION: Alanine amide

<400> SEQUENCE: 4
```

-continued

Xaa Met Gln Leu Ala Arg Gln Met Lys Gln Leu Ala Asp Ser Leu Met
1               5                   10                  15

Gln Leu Ala Arg Gln Val Ser Arg Leu Glu Ser Xaa
            20                  25

<210> SEQ ID NO 5
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetyl methionine
<220> FEATURE:
<221> NAME/KEY: MISC_FEATURE
<222> LOCATION: (21)..(21)
<223> OTHER INFORMATION: Alanine amide

<400> SEQUENCE: 5

Xaa Lys Glu Leu Ala Asp Ser Leu Met Gln Leu Ala Arg Gln Val Asp
1               5                   10                  15

Arg Leu Glu Ser Xaa
            20

<210> SEQ ID NO 6
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetyl methionine
<220> FEATURE:
<221> NAME/KEY: MISC_FEATURE
<222> LOCATION: (21)..(21)
<223> OTHER INFORMATION: Alanine amide

<400> SEQUENCE: 6

Xaa Lys Gln Leu Ala Asp Ser Leu His Gln Leu Ala His Gln Val Ser
1               5                   10                  15

His Leu Glu His Xaa
            20

<210> SEQ ID NO 7
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetyl methionine
<220> FEATURE:
<221> NAME/KEY: MISC_FEATURE
<222> LOCATION: (21)..(21)
<223> OTHER INFORMATION: Alanine amide

<400> SEQUENCE: 7

Xaa Glu Glu Leu Ala Asp Ser Leu Glu Glu Leu Ala Arg Gln Val Glu
1               5                   10                  15

Glu Leu Glu Ser Xaa
            20

```
<210> SEQ ID NO 8
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetyl methionine
<220> FEATURE:
<221> NAME/KEY: MISC_FEATURE
<222> LOCATION: (21)..(21)
<223> OTHER INFORMATION: Alanine amide

<400> SEQUENCE: 8

Xaa Lys Lys Leu Ala Asp Ser Leu Lys Lys Leu Ala Arg Gln Val Lys
1               5                   10                  15

Lys Leu Glu Ser Xaa
            20

<210> SEQ ID NO 9
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetyl methionine
<220> FEATURE:
<221> NAME/KEY: MISC_FEATURE
<222> LOCATION: (21)..(21)
<223> OTHER INFORMATION: Alanine amide

<400> SEQUENCE: 9

Xaa Lys Gln Leu Ala Asp Ser Leu His Gln Leu Ala His Lys Val Ser
1               5                   10                  15

His Leu Glu His Xaa
            20

<210> SEQ ID NO 10
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetyl glutamic acid
<220> FEATURE:
<221> NAME/KEY: MISC_FEATURE
<222> LOCATION: (21)..(21)
<223> OTHER INFORMATION: Lysine amide

<400> SEQUENCE: 10

Xaa Ile Ser Ala Leu Glu Lys Glu Ile Ser Ala Leu Glu Lys Glu Ile
1               5                   10                  15

Ser Ala Leu Glu Xaa
            20

<210> SEQ ID NO 11
<211> LENGTH: 21
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (1)..(1)
<223> OTHER INFORMATION: Acetyl lysine
<220> FEATURE:
<221> NAME/KEY: MISC_FEATURE
<222> LOCATION: (21)..(21)
<223> OTHER INFORMATION: Glutamic acid amide

<400> SEQUENCE: 11

Xaa Ile Ser Ala Leu Lys Glu Lys Ile Ser Ala Leu Lys Glu Lys Ile
1               5                   10                  15

Ser Ala Leu Lys Xaa
            20

<210> SEQ ID NO 12
<211> LENGTH: 24
<212> TYPE: PRT
<213> ORGANISM: Artificial Sequence
<220> FEATURE:
<223> OTHER INFORMATION: Synthetic

<400> SEQUENCE: 12

Pro Ser Met Lys Glu Leu Ala Asp Ser Leu His Glu Leu Ala Arg Glu
1               5                   10                  15

Val Ser Arg Leu Glu His Ala Asp
            20

<210> SEQ ID NO 13
<211> LENGTH: 24
<212> TYPE: PRT
<213> ORGANISM: Artificial Sequence
<220> FEATURE:
<223> OTHER INFORMATION: Synthetic

<400> SEQUENCE: 13

Pro Ser Met Lys Glu Leu Ala Asp Ser Leu His Gln Leu Ala Arg Gln
1               5                   10                  15

Val Ser Arg Leu Glu His Ala Asp
            20

<210> SEQ ID NO 14
<211> LENGTH: 24
<212> TYPE: PRT
<213> ORGANISM: Artificial Sequence
<220> FEATURE:
<223> OTHER INFORMATION: Synthetic

<400> SEQUENCE: 14

Pro Ser Met Lys Gln Leu Ala Asp Ser Leu His Glu Leu Ala Arg Gln
1               5                   10                  15

Val Ser Arg Leu Glu His Ala Asp
            20

<210> SEQ ID NO 15
<211> LENGTH: 24
<212> TYPE: PRT
<213> ORGANISM: Artificial Sequence
<220> FEATURE:
<223> OTHER INFORMATION: Synthetic

<400> SEQUENCE: 15

Pro Ser Met Lys Gln Leu Ala Asp Ser Leu His Gln Leu Ala Arg Gln
1               5                   10                  15

Val Ser Arg Leu Glu His Ala Asp
            20
```

```
<210> SEQ ID NO 16
<211> LENGTH: 24
<212> TYPE: PRT
<213> ORGANISM: Artificial Sequence
<220> FEATURE:
<223> OTHER INFORMATION: Synthetic

<400> SEQUENCE: 16

Pro Ser Met Lys Glu Leu Ala Asp Ser Leu His Glu Leu Ala Arg Gln
1               5                   10                  15

Val Ser Arg Leu Glu His Ala Asp
            20

<210> SEQ ID NO 17
<211> LENGTH: 24
<212> TYPE: PRT
<213> ORGANISM: Artificial Sequence
<220> FEATURE:
<223> OTHER INFORMATION: Synthetic

<400> SEQUENCE: 17

Pro Ser Met Lys Glu Leu Ala Asp Ser Leu His Gln Leu Ala Arg Glu
1               5                   10                  15

Val Ser Arg Leu Glu His Ala Asp
            20

<210> SEQ ID NO 18
<211> LENGTH: 24
<212> TYPE: PRT
<213> ORGANISM: Artificial Sequence
<220> FEATURE:
<223> OTHER INFORMATION: Synthetic

<400> SEQUENCE: 18

Pro Ser Met Lys Gln Leu Ala Asp Ser Leu His Glu Leu Ala Arg Glu
1               5                   10                  15

Val Ser Arg Leu Glu His Ala Asp
            20

<210> SEQ ID NO 19
<211> LENGTH: 24
<212> TYPE: PRT
<213> ORGANISM: Artificial Sequence
<220> FEATURE:
<223> OTHER INFORMATION: Synthetic

<400> SEQUENCE: 19

Pro Ser Ala Lys Ser Leu Ala Glu Ser Leu His Ser Leu Ala Arg Ser
1               5                   10                  15

Val Ser Arg Leu Glu His Ala Asp
            20

<210> SEQ ID NO 20
<211> LENGTH: 25
<212> TYPE: PRT
<213> ORGANISM: Artificial Sequence
<220> FEATURE:
<223> OTHER INFORMATION: Synthetic

<400> SEQUENCE: 20

Pro Ser Ala Lys Ser Val Ala Glu Ser Leu His Ser Leu Ala Arg Ser
1               5                   10                  15

Val Ser Arg Leu Val Glu His Ala Asp
```

20                  25

<210> SEQ ID NO 21
<211> LENGTH: 25
<212> TYPE: PRT
<213> ORGANISM: Artificial Sequence
<220> FEATURE:
<223> OTHER INFORMATION: Synthetic

<400> SEQUENCE: 21

Pro Ser Ala His Ser Val Ala Glu Ser Leu His Ser Leu Ala Arg Ser
1               5                   10                  15

Val Ser Arg Leu Val Glu His Ala Asp
            20                  25

<210> SEQ ID NO 22
<211> LENGTH: 25
<212> TYPE: PRT
<213> ORGANISM: Artificial Sequence
<220> FEATURE:
<223> OTHER INFORMATION: Synthetic

<400> SEQUENCE: 22

Pro Ser Ala His Ser Val Ala Lys Ser Leu His Ser Leu Ala Arg Ser
1               5                   10                  15

Val Ser Arg Leu Val Ser His Ala Asp
            20                  25

<210> SEQ ID NO 23
<211> LENGTH: 25
<212> TYPE: PRT
<213> ORGANISM: Artificial Sequence
<220> FEATURE:
<223> OTHER INFORMATION: Synthetic

<400> SEQUENCE: 23

Pro Ser Ala His Ser Val Ala Glu Ser Leu His Ser Leu Ala Glu Ser
1               5                   10                  15

Val Ser Glu Leu Val Ser His Ala Asp
            20                  25

<210> SEQ ID NO 24
<211> LENGTH: 25
<212> TYPE: PRT
<213> ORGANISM: Artificial Sequence
<220> FEATURE:
<223> OTHER INFORMATION: Synthetic

<400> SEQUENCE: 24

Pro Ser Ala Gln Ser Val Ala Gln Ser Leu Ala Gln Leu Ala Gln Ser
1               5                   10                  15

Val Ser Gln Leu Val Ser Gln Ala Asp
            20                  25

<210> SEQ ID NO 25
<211> LENGTH: 25
<212> TYPE: PRT
<213> ORGANISM: Artificial Sequence
<220> FEATURE:
<223> OTHER INFORMATION: Synthetic

<400> SEQUENCE: 25

Pro Ser Ala Glu Ser Val Ala Glu Ser Leu Ala Glu Leu Ala Glu Ser
1               5                   10                  15

Val Ser Glu Leu Val Ser Glu Ala Asp
            20                  25

<210> SEQ ID NO 26
<211> LENGTH: 25
<212> TYPE: PRT
<213> ORGANISM: Artificial Sequence
<220> FEATURE:
<223> OTHER INFORMATION: Synthetic

<400> SEQUENCE: 26

Pro Ser Ala Asn Ser Val Ala Asn Ser Leu Ala Asn Leu Ala Asn Ser
1               5                   10                  15

Val Ser Asn Leu Val Ser Asn Ala Asp
            20                  25

<210> SEQ ID NO 27
<211> LENGTH: 25
<212> TYPE: PRT
<213> ORGANISM: Artificial Sequence
<220> FEATURE:
<223> OTHER INFORMATION: Synthetic

<400> SEQUENCE: 27

Pro Ser Ala Asp Ser Val Ala Asp Ser Leu Ala Asp Leu Ala Asp Ser
1               5                   10                  15

Val Ser Pro Leu Val Ser Asp Ala Asp
            20                  25

<210> SEQ ID NO 28
<211> LENGTH: 25
<212> TYPE: PRT
<213> ORGANISM: Artificial Sequence
<220> FEATURE:
<223> OTHER INFORMATION: Synthetic

<400> SEQUENCE: 28

Pro Ser Ala Gln Ser Val Ala Glu Ser Leu Ala Gln Leu Ala Glu Ser
1               5                   10                  15

Val Ser Glu Leu Val Ser Gln Ala Asp
            20                  25

<210> SEQ ID NO 29
<211> LENGTH: 25
<212> TYPE: PRT
<213> ORGANISM: Artificial Sequence
<220> FEATURE:
<223> OTHER INFORMATION: Synthetic

<400> SEQUENCE: 29

Pro Ser Ala Glu Ser Val Ala Glu Ser Leu Ala Glu Leu Ala Glu Ser
1               5                   10                  15

Val Ser Glu Leu Val Ser Glu Ala Asp
            20                  25

<210> SEQ ID NO 30
<211> LENGTH: 25
<212> TYPE: PRT
<213> ORGANISM: Artificial Sequence
<220> FEATURE:
<223> OTHER INFORMATION: Synthetic

<400> SEQUENCE: 30

Pro Ser Ala Asn Ser Val Ala Glu Ser Leu Ala Asn Leu Ala Glu Ser
1               5                   10                  15

-continued

Val Ser Glu Leu Val Ser Asn Ala Asp
            20              25

<210> SEQ ID NO 31
<211> LENGTH: 25
<212> TYPE: PRT
<213> ORGANISM: Artificial Sequence
<220> FEATURE:
<223> OTHER INFORMATION: Synthetic

<400> SEQUENCE: 31

Pro Ser Ala Asp Ser Val Ala Glu Ser Leu Ala Asp Leu Ala Glu Ser
1               5                   10                  15

Val Ser Glu Leu Val Ser Asp Ala Asp
            20              25

<210> SEQ ID NO 32
<211> LENGTH: 98
<212> TYPE: PRT
<213> ORGANISM: Artificial Sequence
<220> FEATURE:
<223> OTHER INFORMATION: Synthetic

<400> SEQUENCE: 32

Met Asp Pro Ser Met Lys Gln Leu Ala Asp Ser Leu His Gln Leu Ala
1               5                   10                  15

Arg Gln Val Ser Arg Leu Glu His Ala Asp Pro Ser Met Lys Gln Leu
            20                  25                  30

Ala Asp Ser Leu His Gln Leu Ala Arg Gln Val Ser Arg Leu Glu His
        35                  40                  45

Ala Asp Pro Ser Met Lys Gln Leu Ala Asp Ser Leu His Gln Leu Ala
    50                  55                  60

Arg Gln Val Ser Arg Leu Glu His Ala Asp Pro Ser Met Lys Gln Leu
65              70                  75                  80

Ala Asp Ser Leu His Gln Leu Ala Arg Gln Val Ser Arg Leu Glu His
            85                  90                  95

Ala Asp

<210> SEQ ID NO 33
<211> LENGTH: 50
<212> TYPE: PRT
<213> ORGANISM: Artificial Sequence
<220> FEATURE:
<223> OTHER INFORMATION: Synthetic

<400> SEQUENCE: 33

Met Asp Pro Ser Met Lys Gln Leu Ala Asp Ser Leu His Gln Leu Ala
1               5                   10                  15

Arg Gln Val Ser Arg Leu Glu His Ala Asp Pro Ser Met Lys Gln Leu
            20                  25                  30

Ala Asp Ser Leu His Gln Leu Ala Arg Gln Val Ser Arg Leu Glu His
        35                  40                  45

Ala Asp
    50

<210> SEQ ID NO 34
<211> LENGTH: 98
<212> TYPE: PRT
<213> ORGANISM: Artificial Sequence
<220> FEATURE:
<223> OTHER INFORMATION: Synthetic

```
<400> SEQUENCE: 34

Met Asp Pro Ser Ala Lys Ser Leu Ala Glu Ser Leu His Ser Leu Ala
1               5                   10                  15

Arg Ser Val Ser Arg Leu Glu His Ala Asp Pro Ser Ala Lys Ser Leu
            20                  25                  30

Ala Glu Ser Leu His Ser Leu Ala Arg Ser Val Ser Arg Leu Glu His
        35                  40                  45

Ala Asp Pro Ser Ala Lys Ser Leu Ala Glu Ser Leu His Ser Leu Ala
    50                  55                  60

Arg Ser Val Ser Arg Leu Glu His Ala Asp Pro Ser Ala Lys Ser Leu
65                  70                  75                  80

Ala Glu Ser Leu His Ser Leu Ala Arg Ser Val Ser Arg Leu Glu His
                85                  90                  95

Ala Asp

<210> SEQ ID NO 35
<211> LENGTH: 102
<212> TYPE: PRT
<213> ORGANISM: Artificial Sequence
<220> FEATURE:
<223> OTHER INFORMATION: Synthetic

<400> SEQUENCE: 35

Met Asp Pro Ser Ala Lys Ser Val Ala Glu Ser Leu His Ser Leu Ala
1               5                   10                  15

Arg Ser Val Ser Arg Leu Val Glu His Ala Asp Pro Ser Ala Lys Ser
            20                  25                  30

Val Ala Glu Ser Leu His Ser Leu Ala Arg Ser Val Ser Arg Leu Val
        35                  40                  45

Glu His Ala Asp Pro Ser Ala Lys Ser Val Ala Glu Ser Leu His Ser
    50                  55                  60

Leu Ala Arg Ser Val Ser Arg Leu Val Glu His Ala Asp Pro Ser Ala
65                  70                  75                  80

Lys Ser Val Ala Glu Ser Leu His Ser Leu Ala Arg Ser Val Ser Arg
                85                  90                  95

Leu Val Glu His Ala Asp
            100

<210> SEQ ID NO 36
<211> LENGTH: 102
<212> TYPE: PRT
<213> ORGANISM: Artificial Sequence
<220> FEATURE:
<223> OTHER INFORMATION: Synthetic

<400> SEQUENCE: 36

Met Asp Pro Ser Ala His Ser Val Ala Glu Ser Leu His Ser Leu Ala
1               5                   10                  15

Arg Ser Val Ser Arg Leu Val Glu His Ala Asp Pro Ser Ala His Ser
            20                  25                  30

Val Ala Glu Ser Leu His Ser Leu Ala Arg Ser Val Ser Arg Leu Val
        35                  40                  45

Glu His Ala Asp Pro Ser Ala His Ser Val Ala Glu Ser Leu His Ser
    50                  55                  60

Leu Ala Arg Ser Val Ser Arg Leu Val Glu His Ala Asp Pro Ser Ala
65                  70                  75                  80
```

His Ser Val Ala Glu Ser Leu His Ser Leu Ala Arg Ser Val Ser Arg
                85                  90                  95

Leu Val Glu His Ala Asp
            100

<210> SEQ ID NO 37
<211> LENGTH: 102
<212> TYPE: PRT
<213> ORGANISM: Artificial Sequence
<220> FEATURE:
<223> OTHER INFORMATION: Synthetic

<400> SEQUENCE: 37

Met Asp Pro Ser Ala His Ser Val Ala Lys Ser Leu His Ser Leu Ala
1               5                   10                  15

Arg Ser Val Ser Arg Leu Val Ser His Ala Asp Pro Ser Ala His Ser
            20                  25                  30

Val Ala Lys Ser Leu His Ser Leu Ala Arg Ser Val Ser Arg Leu Val
        35                  40                  45

Ser His Ala Asp Pro Ser Ala His Ser Val Ala Lys Ser Leu His Ser
    50                  55                  60

Leu Ala Arg Ser Val Ser Arg Leu Val Ser His Ala Asp Pro Ser Ala
65                  70                  75                  80

His Ser Val Ala Lys Ser Leu His Ser Leu Ala Arg Ser Val Ser Arg
                85                  90                  95

Leu Val Ser His Ala Asp
            100

<210> SEQ ID NO 38
<211> LENGTH: 102
<212> TYPE: PRT
<213> ORGANISM: Artificial Sequence
<220> FEATURE:
<223> OTHER INFORMATION: Synthetic

<400> SEQUENCE: 38

Met Asp Pro Ser Ala His Ser Val Ala Glu Ser Leu His Ser Leu Ala
1               5                   10                  15

Glu Ser Val Ser Glu Leu Val Ser His Ala Asp Pro Ser Ala His Ser
            20                  25                  30

Val Ala Glu Ser Leu His Ser Leu Ala Glu Ser Val Ser Glu Leu Val
        35                  40                  45

Ser His Ala Asp Pro Ser Ala His Ser Val Ala Glu Ser Leu His Ser
    50                  55                  60

Leu Ala Glu Ser Val Ser Glu Leu Val Ser His Ala Asp Pro Ser Ala
65                  70                  75                  80

His Ser Val Ala Glu Ser Leu His Ser Leu Ala Glu Ser Val Ser Glu
                85                  90                  95

Leu Val Ser His Ala Asp
            100

<210> SEQ ID NO 39
<211> LENGTH: 102
<212> TYPE: PRT
<213> ORGANISM: Artificial Sequence
<220> FEATURE:
<223> OTHER INFORMATION: Synthetic

<400> SEQUENCE: 39

Met Asp Pro Ser Ala Gln Ser Val Ala Gln Ser Leu Ala Gln Leu Ala

```
1               5                   10                  15
Gln Ser Val Ser Gln Leu Val Ser Gln Ala Asp Pro Ser Ala Gln Ser
            20                  25                  30

Val Ala Gln Ser Leu Ala Gln Leu Ala Gln Ser Val Ser Gln Leu Val
            35                  40                  45

Ser Gln Ala Asp Pro Ser Ala Gln Ser Val Ala Gln Ser Leu Ala Gln
        50                  55                  60

Leu Ala Gln Ser Val Ser Gln Leu Val Ser Gln Ala Asp Pro Ser Ala
65                  70                  75                  80

Gln Ser Val Ala Gln Ser Leu Ala Gln Leu Ala Gln Ser Val Ser Gln
                85                  90                  95

Leu Val Ser Gln Ala Asp
            100

<210> SEQ ID NO 40
<211> LENGTH: 102
<212> TYPE: PRT
<213> ORGANISM: Artificial Sequence
<220> FEATURE:
<223> OTHER INFORMATION: Synthetic

<400> SEQUENCE: 40

Met Asp Pro Ser Ala Asn Ser Val Ala Asn Ser Leu Ala Asn Leu Ala
1               5                   10                  15

Asn Ser Val Ser Asn Leu Val Ser Asn Ala Asp Pro Ser Ala Asn Ser
            20                  25                  30

Val Ala Asn Ser Leu Ala Asn Leu Ala Asn Ser Val Ser Asn Leu Val
            35                  40                  45

Ser Asn Ala Asp Pro Ser Ala Asn Ser Val Ala Asn Ser Leu Ala Asn
        50                  55                  60

Leu Ala Asn Ser Val Ser Asn Leu Val Ser Asn Ala Asp Pro Ser Ala
65                  70                  75                  80

Asn Ser Val Ala Asn Ser Leu Ala Asn Leu Ala Asn Ser Val Ser Asn
                85                  90                  95

Leu Val Ser Asn Ala Asp
            100

<210> SEQ ID NO 41
<211> LENGTH: 102
<212> TYPE: PRT
<213> ORGANISM: Artificial Sequence
<220> FEATURE:
<223> OTHER INFORMATION: Synthetic

<400> SEQUENCE: 41

Met Asp Pro Ser Ala Gln Ser Val Ala Glu Ser Leu Ala Gln Leu Ala
1               5                   10                  15

Glu Ser Val Ser Glu Leu Val Ser Gln Ala Asp Pro Ser Ala Gln Ser
            20                  25                  30

Val Ala Glu Ser Leu Ala Gln Leu Ala Glu Ser Val Ser Glu Leu Val
            35                  40                  45

Ser Gln Ala Asp Pro Ser Ala Gln Ser Val Ala Glu Ser Leu Ala Gln
        50                  55                  60

Leu Ala Glu Ser Val Ser Glu Leu Val Ser Gln Ala Asp Pro Ser Ala
65                  70                  75                  80

Gln Ser Val Ala Glu Ser Leu Ala Gln Leu Ala Glu Ser Val Ser Glu
                85                  90                  95
```

Leu Val Ser Gln Ala Asp
            100

<210> SEQ ID NO 42
<211> LENGTH: 102
<212> TYPE: PRT
<213> ORGANISM: Artificial Sequence
<220> FEATURE:
<223> OTHER INFORMATION: Synthetic

<400> SEQUENCE: 42

Met Asp Pro Ser Ala Asn Ser Val Ala Glu Ser Leu Ala Asn Leu Ala
1               5                   10                  15

Glu Ser Val Ser Glu Leu Val Ser Asn Ala Asp Pro Ser Ala Asn Ser
            20                  25                  30

Val Ala Glu Ser Leu Ala Asn Leu Ala Glu Ser Val Ser Glu Leu Val
        35                  40                  45

Ser Asn Ala Asp Pro Ser Ala Asn Ser Val Ala Glu Ser Leu Ala Asn
    50                  55                  60

Leu Ala Glu Ser Val Ser Glu Leu Val Ser Asn Ala Asp Pro Ser Ala
65                  70                  75                  80

Asn Ser Val Ala Glu Ser Leu Ala Asn Leu Ala Glu Ser Val Ser Glu
                85                  90                  95

Leu Val Ser Asn Ala Asp
            100

<210> SEQ ID NO 43
<211> LENGTH: 98
<212> TYPE: PRT
<213> ORGANISM: Artificial Sequence
<220> FEATURE:
<223> OTHER INFORMATION: Synthetic

<400> SEQUENCE: 43

Met Asp Pro Ser Met Lys Gln Leu Ala Asp Ser Leu Met Gln Leu Ala
1               5                   10                  15

Arg Gln Val Ser Arg Leu Glu Ser Ala Asp Pro Ser Met Lys Gln Leu
            20                  25                  30

Ala Asp Ser Leu Met Gln Leu Ala Arg Gln Val Ser Arg Leu Glu Ser
        35                  40                  45

Ala Asp Pro Ser Met Lys Gln Leu Ala Asp Ser Leu Met Gln Leu Ala
    50                  55                  60

Arg Gln Val Ser Arg Leu Glu Ser Ala Asp Pro Ser Met Lys Gln Leu
65                  70                  75                  80

Ala Asp Ser Leu Met Gln Leu Ala Arg Gln Val Ser Arg Leu Glu Ser
                85                  90                  95

Ala Asp

<210> SEQ ID NO 44
<211> LENGTH: 126
<212> TYPE: PRT
<213> ORGANISM: Artificial Sequence
<220> FEATURE:
<223> OTHER INFORMATION: Synthetic

<400> SEQUENCE: 44

Met Asp Pro Ser Leu Met Gln Leu Ala Arg Gln Met Lys Gln Leu Ala
1               5                   10                  15

Asp Ser Leu Met Gln Leu Ala Arg Gln Val Ser Arg Leu Glu Ser Ala
            20                  25                  30

```
Asp Pro Ser Leu Met Gln Leu Ala Arg Gln Met Lys Gln Leu Ala Asp
        35                  40                  45

Ser Leu Met Gln Leu Ala Arg Gln Val Ser Arg Leu Glu Ser Ala Asp
 50                  55                  60

Pro Ser Leu Met Gln Leu Ala Arg Gln Met Lys Gln Leu Ala Asp Ser
65                  70                  75                  80

Leu Met Gln Leu Ala Arg Gln Val Ser Arg Leu Glu Ser Ala Asp Pro
                85                  90                  95

Ser Leu Met Gln Leu Ala Arg Gln Met Lys Gln Leu Ala Asp Ser Leu
            100                 105                 110

Met Gln Leu Ala Arg Gln Val Ser Arg Leu Glu Ser Ala Asp
        115                 120                 125

<210> SEQ ID NO 45
<211> LENGTH: 98
<212> TYPE: PRT
<213> ORGANISM: Artificial Sequence
<220> FEATURE:
<223> OTHER INFORMATION: Synthetic

<400> SEQUENCE: 45

Met Asp Pro Ser Met Lys Glu Leu Ala Asp Ser Leu Met Gln Leu Ala
1               5                   10                  15

Arg Gln Val Asp Arg Leu Glu Ser Ala Asp Pro Ser Met Lys Glu Leu
            20                  25                  30

Ala Asp Ser Leu Met Gln Leu Ala Arg Gln Val Asp Arg Leu Glu Ser
        35                  40                  45

Ala Asp Pro Ser Met Lys Glu Leu Ala Asp Ser Leu Met Gln Leu Ala
    50                  55                  60

Arg Gln Val Asp Arg Leu Glu Ser Ala Asp Pro Ser Met Lys Glu Leu
65                  70                  75                  80

Ala Asp Ser Leu Met Gln Leu Ala Arg Gln Val Asp Arg Leu Glu Ser
                85                  90                  95

Ala Asp

<210> SEQ ID NO 46
<211> LENGTH: 98
<212> TYPE: PRT
<213> ORGANISM: Artificial Sequence
<220> FEATURE:
<223> OTHER INFORMATION: Synthetic

<400> SEQUENCE: 46

Met Asp Pro Ser Met Lys Gln Leu Ala Asp Ser Leu His Gln Leu Ala
1               5                   10                  15

His Gln Val Ser His Leu Glu His Ala Asp Pro Ser Met Lys Gln Leu
            20                  25                  30

Ala Asp Ser Leu His Gln Leu Ala His Gln Val Ser His Leu Glu His
        35                  40                  45

Ala Asp Pro Ser Met Lys Gln Leu Ala Asp Ser Leu His Gln Leu Ala
    50                  55                  60

His Gln Val Ser His Leu Glu His Ala Asp Pro Ser Met Lys Gln Leu
65                  70                  75                  80

Ala Asp Ser Leu His Gln Leu Ala His Gln Val Ser His Leu Glu His
                85                  90                  95

Ala Asp
```

<210> SEQ ID NO 47
<211> LENGTH: 98
<212> TYPE: PRT
<213> ORGANISM: Artificial Sequence
<220> FEATURE:
<223> OTHER INFORMATION: Synthetic

<400> SEQUENCE: 47

```
Met Asp Pro Ser Met Glu Glu Leu Ala Asp Ser Leu Glu Glu Leu Ala
1               5                   10                  15

Arg Gln Val Glu Glu Leu Glu Ser Ala Asp Pro Ser Met Glu Glu Leu
            20                  25                  30

Ala Asp Ser Leu Glu Glu Leu Ala Arg Gln Val Glu Glu Leu Glu Ser
        35                  40                  45

Ala Asp Pro Ser Met Glu Glu Leu Ala Asp Ser Leu Glu Glu Leu Ala
    50                  55                  60

Arg Gln Val Glu Glu Leu Glu Ser Ala Asp Pro Ser Met Glu Glu Leu
65                  70                  75                  80

Ala Asp Ser Leu Glu Glu Leu Ala Arg Gln Val Glu Glu Leu Glu Ser
                85                  90                  95

Ala Asp
```

<210> SEQ ID NO 48
<211> LENGTH: 98
<212> TYPE: PRT
<213> ORGANISM: Artificial Sequence
<220> FEATURE:
<223> OTHER INFORMATION: Synthetic

<400> SEQUENCE: 48

```
Met Asp Pro Ser Met Lys Lys Leu Ala Asp Ser Leu Lys Lys Leu Ala
1               5                   10                  15

Arg Gln Val Lys Lys Leu Glu Ser Ala Asp Pro Ser Met Lys Lys Leu
            20                  25                  30

Ala Asp Ser Leu Lys Lys Leu Ala Arg Gln Val Lys Lys Leu Glu Ser
        35                  40                  45

Ala Asp Pro Ser Met Lys Lys Leu Ala Asp Ser Leu Lys Lys Leu Ala
    50                  55                  60

Arg Gln Val Lys Lys Leu Glu Ser Ala Asp Pro Ser Met Lys Lys Leu
65                  70                  75                  80

Ala Asp Ser Leu Lys Lys Leu Ala Arg Gln Val Lys Lys Leu Glu Ser
                85                  90                  95

Ala Asp
```

<210> SEQ ID NO 49
<211> LENGTH: 98
<212> TYPE: PRT
<213> ORGANISM: Artificial Sequence
<220> FEATURE:
<223> OTHER INFORMATION: Synthetic

<400> SEQUENCE: 49

```
Met Asp Pro Ser Met Lys Gln Leu Ala Asp Ser Leu His Gln Leu Ala
1               5                   10                  15

His Lys Val Ser His Leu Glu His Ala Asp Pro Ser Met Lys Gln Leu
            20                  25                  30

Ala Asp Ser Leu His Gln Leu Ala His Lys Val Ser His Leu Glu His
        35                  40                  45
```

```
Ala Asp Pro Ser Met Lys Gln Leu Ala Asp Ser Leu His Gln Leu Ala
 50                  55                  60

His Lys Val Ser His Leu Glu His Ala Asp Pro Ser Met Lys Gln Leu
 65                  70                  75                  80

Ala Asp Ser Leu His Gln Leu Ala His Lys Val Ser His Leu Glu His
                 85                  90                  95

Ala Asp

<210> SEQ ID NO 50
<211> LENGTH: 98
<212> TYPE: PRT
<213> ORGANISM: Artificial Sequence
<220> FEATURE:
<223> OTHER INFORMATION: Synthetic

<400> SEQUENCE: 50

Met Asp Pro Ser Glu Ile Ser Ala Leu Glu Lys Glu Ile Ser Ala Leu
 1               5                  10                  15

Glu Lys Glu Ile Ser Ala Leu Glu Lys Asp Pro Ser Glu Ile Ser Ala
                 20                  25                  30

Leu Glu Lys Glu Ile Ser Ala Leu Glu Lys Glu Ile Ser Ala Leu Glu
             35                  40                  45

Lys Asp Pro Ser Glu Ile Ser Ala Leu Glu Lys Glu Ile Ser Ala Leu
 50                  55                  60

Glu Lys Glu Ile Ser Ala Leu Glu Lys Asp Pro Ser Glu Ile Ser Ala
 65                  70                  75                  80

Leu Glu Lys Glu Ile Ser Ala Leu Glu Lys Glu Ile Ser Ala Leu Glu
                 85                  90                  95

Lys Asp

<210> SEQ ID NO 51
<211> LENGTH: 98
<212> TYPE: PRT
<213> ORGANISM: Artificial Sequence
<220> FEATURE:
<223> OTHER INFORMATION: Synthetic

<400> SEQUENCE: 51

Met Asp Pro Ser Lys Ile Ser Ala Leu Lys Glu Lys Ile Ser Ala Leu
 1               5                  10                  15

Lys Glu Lys Ile Ser Ala Leu Lys Glu Asp Pro Ser Lys Ile Ser Ala
                 20                  25                  30

Leu Lys Glu Lys Ile Ser Ala Leu Lys Glu Lys Ile Ser Ala Leu Lys
             35                  40                  45

Glu Asp Pro Ser Lys Ile Ser Ala Leu Lys Glu Lys Ile Ser Ala Leu
 50                  55                  60

Lys Glu Lys Ile Ser Ala Leu Lys Glu Asp Pro Ser Lys Ile Ser Ala
 65                  70                  75                  80

Leu Lys Glu Lys Ile Ser Ala Leu Lys Glu Lys Ile Ser Ala Leu Lys
                 85                  90                  95

Glu Asp

<210> SEQ ID NO 52
<211> LENGTH: 98
<212> TYPE: PRT
<213> ORGANISM: Artificial Sequence
<220> FEATURE:
<223> OTHER INFORMATION: Synthetic
```

-continued

<400> SEQUENCE: 52

Met Asp Pro Ser Met Lys Glu Leu Ala Asp Ser Leu His Glu Leu Ala
1               5                   10                  15

Arg Glu Val Ser Arg Leu Glu His Ala Asp Pro Ser Met Lys Glu Leu
            20                  25                  30

Ala Asp Ser Leu His Glu Leu Ala Arg Glu Val Ser Arg Leu Glu His
        35                  40                  45

Ala Asp Pro Ser Met Lys Glu Leu Ala Asp Ser Leu His Glu Leu Ala
    50                  55                  60

Arg Glu Val Ser Arg Leu Glu His Ala Asp Pro Ser Met Lys Glu Leu
65                  70                  75                  80

Ala Asp Ser Leu His Glu Leu Ala Arg Glu Val Ser Arg Leu Glu His
                85                  90                  95

Ala Asp

<210> SEQ ID NO 53
<211> LENGTH: 98
<212> TYPE: PRT
<213> ORGANISM: Artificial Sequence
<220> FEATURE:
<223> OTHER INFORMATION: Synthetic

<400> SEQUENCE: 53

Met Asp Pro Ser Met Lys Glu Leu Ala Asp Ser Leu His Gln Leu Ala
1               5                   10                  15

Arg Gln Val Ser Arg Leu Glu His Ala Asp Pro Ser Met Lys Glu Leu
            20                  25                  30

Ala Asp Ser Leu His Gln Leu Ala Arg Gln Val Ser Arg Leu Glu His
        35                  40                  45

Ala Asp Pro Ser Met Lys Glu Leu Ala Asp Ser Leu His Gln Leu Ala
    50                  55                  60

Arg Gln Val Ser Arg Leu Glu His Ala Asp Pro Ser Met Lys Glu Leu
65                  70                  75                  80

Ala Asp Ser Leu His Gln Leu Ala Arg Gln Val Ser Arg Leu Glu His
                85                  90                  95

Ala Asp

<210> SEQ ID NO 54
<211> LENGTH: 98
<212> TYPE: PRT
<213> ORGANISM: Artificial Sequence
<220> FEATURE:
<223> OTHER INFORMATION: Synthetic

<400> SEQUENCE: 54

Met Asp Pro Ser Met Lys Gln Leu Ala Asp Ser Leu His Glu Leu Ala
1               5                   10                  15

Arg Gln Val Ser Arg Leu Glu His Ala Asp Pro Ser Met Lys Gln Leu
            20                  25                  30

Ala Asp Ser Leu His Glu Leu Ala Arg Gln Val Ser Arg Leu Glu His
        35                  40                  45

Ala Asp Pro Ser Met Lys Gln Leu Ala Asp Ser Leu His Glu Leu Ala
    50                  55                  60

Arg Gln Val Ser Arg Leu Glu His Ala Asp Pro Ser Met Lys Gln Leu
65                  70                  75                  80

Ala Asp Ser Leu His Glu Leu Ala Arg Gln Val Ser Arg Leu Glu His
                85                  90                  95

Ala Asp

<210> SEQ ID NO 55
<211> LENGTH: 98
<212> TYPE: PRT
<213> ORGANISM: Artificial Sequence
<220> FEATURE:
<223> OTHER INFORMATION: Synthetic

<400> SEQUENCE: 55

```
Met Asp Pro Ser Met Lys Glu Leu Ala Asp Ser Leu His Glu Leu Ala
1               5                   10                  15

Arg Gln Val Ser Arg Leu Glu His Ala Asp Pro Ser Met Lys Glu Leu
            20                  25                  30

Ala Asp Ser Leu His Glu Leu Ala Arg Gln Val Ser Arg Leu Glu His
        35                  40                  45

Ala Asp Pro Ser Met Lys Glu Leu Ala Asp Ser Leu His Glu Leu Ala
    50                  55                  60

Arg Gln Val Ser Arg Leu Glu His Ala Asp Pro Ser Met Lys Glu Leu
65                  70                  75                  80

Ala Asp Ser Leu His Glu Leu Ala Arg Gln Val Ser Arg Leu Glu His
                85                  90                  95

Ala Asp
```

<210> SEQ ID NO 56
<211> LENGTH: 98
<212> TYPE: PRT
<213> ORGANISM: Artificial Sequence
<220> FEATURE:
<223> OTHER INFORMATION: Synthetic

<400> SEQUENCE: 56

```
Met Asp Pro Ser Met Lys Glu Leu Ala Asp Ser Leu His Gln Leu Ala
1               5                   10                  15

Arg Glu Val Ser Arg Leu Glu His Ala Asp Pro Ser Met Lys Glu Leu
            20                  25                  30

Ala Asp Ser Leu His Gln Leu Ala Arg Glu Val Ser Arg Leu Glu His
        35                  40                  45

Ala Asp Pro Ser Met Lys Glu Leu Ala Asp Ser Leu His Gln Leu Ala
    50                  55                  60

Arg Glu Val Ser Arg Leu Glu His Ala Asp Pro Ser Met Lys Glu Leu
65                  70                  75                  80

Ala Asp Ser Leu His Gln Leu Ala Arg Glu Val Ser Arg Leu Glu His
                85                  90                  95

Ala Asp
```

<210> SEQ ID NO 57
<211> LENGTH: 98
<212> TYPE: PRT
<213> ORGANISM: Artificial Sequence
<220> FEATURE:
<223> OTHER INFORMATION: Synthetic

<400> SEQUENCE: 57

```
Met Asp Pro Ser Met Lys Gln Leu Ala Asp Ser Leu His Glu Leu Ala
1               5                   10                  15

Arg Glu Val Ser Arg Leu Glu His Ala Asp Pro Ser Met Lys Gln Leu
            20                  25                  30
```

Ala Asp Ser Leu His Glu Leu Ala Arg Glu Val Ser Arg Leu Glu His
            35                  40                  45

Ala Asp Pro Ser Met Lys Gln Leu Ala Asp Ser Leu His Glu Leu Ala
    50                  55                  60

Arg Glu Val Ser Arg Leu Glu His Ala Asp Pro Ser Met Lys Gln Leu
65                  70                  75                  80

Ala Asp Ser Leu His Glu Leu Ala Arg Glu Val Ser Arg Leu Glu His
                85                  90                  95

Ala Asp

<210> SEQ ID NO 58
<211> LENGTH: 102
<212> TYPE: PRT
<213> ORGANISM: Artificial Sequence
<220> FEATURE:
<223> OTHER INFORMATION: Synthetic

<400> SEQUENCE: 58

Met Asp Pro Ser Ala Glu Ser Val Ala Glu Ser Leu Ala Glu Leu Ala
1               5                   10                  15

Glu Ser Val Ser Glu Leu Val Ser Glu Ala Asp Pro Ser Ala Glu Ser
            20                  25                  30

Val Ala Glu Ser Leu Ala Glu Leu Ala Glu Ser Val Ser Glu Leu Val
            35                  40                  45

Ser Glu Ala Asp Pro Ser Ala Glu Ser Val Ala Glu Ser Leu Ala Glu
    50                  55                  60

Leu Ala Glu Ser Val Ser Glu Leu Val Ser Glu Ala Asp Pro Ser Ala
65                  70                  75                  80

Glu Ser Val Ala Glu Ser Leu Ala Glu Leu Ala Glu Ser Val Ser Glu
                85                  90                  95

Leu Val Ser Glu Ala Asp
            100

<210> SEQ ID NO 59
<211> LENGTH: 102
<212> TYPE: PRT
<213> ORGANISM: Artificial Sequence
<220> FEATURE:
<223> OTHER INFORMATION: Synthetic

<400> SEQUENCE: 59

Met Asp Pro Ser Ala Asp Ser Val Ala Asp Ser Leu Ala Asp Leu Ala
1               5                   10                  15

Asp Ser Val Ser Pro Leu Val Ser Ala Asp Pro Ser Ala Asp Ser
            20                  25                  30

Val Ala Asp Ser Leu Ala Asp Leu Ala Asp Ser Val Ser Pro Leu Val
            35                  40                  45

Ser Asp Ala Asp Pro Ser Ala Asp Ser Val Ala Asp Ser Leu Ala Asp
    50                  55                  60

Leu Ala Asp Ser Val Ser Pro Leu Val Ser Asp Ala Asp Pro Ser Ala
65                  70                  75                  80

Asp Ser Val Ala Asp Ser Leu Ala Asp Leu Ala Asp Ser Val Ser Pro
                85                  90                  95

Leu Val Ser Asp Ala Asp
            100

<210> SEQ ID NO 60
<211> LENGTH: 102

```
<212> TYPE: PRT
<213> ORGANISM: Artificial Sequence
<220> FEATURE:
<223> OTHER INFORMATION: Synthetic

<400> SEQUENCE: 60

Met Asp Pro Ser Ala Glu Ser Val Ala Glu Ser Leu Ala Glu Leu Ala
1               5                   10                  15

Glu Ser Val Ser Glu Leu Val Ser Glu Ala Asp Pro Ser Ala Glu Ser
            20                  25                  30

Val Ala Glu Ser Leu Ala Glu Leu Ala Glu Ser Val Ser Glu Leu Val
        35                  40                  45

Ser Glu Ala Asp Pro Ser Ala Glu Ser Val Ala Glu Ser Leu Ala Glu
    50                  55                  60

Leu Ala Glu Ser Val Ser Glu Leu Val Ser Glu Ala Asp Pro Ser Ala
65                  70                  75                  80

Glu Ser Val Ala Glu Ser Leu Ala Glu Leu Ala Glu Ser Val Ser Glu
                85                  90                  95

Leu Val Ser Glu Ala Asp
            100

<210> SEQ ID NO 61
<211> LENGTH: 102
<212> TYPE: PRT
<213> ORGANISM: Artificial Sequence
<220> FEATURE:
<223> OTHER INFORMATION: Synthetic

<400> SEQUENCE: 61

Met Asp Pro Ser Ala Asp Ser Val Ala Glu Ser Leu Ala Asp Leu Ala
1               5                   10                  15

Glu Ser Val Ser Glu Leu Val Ser Asp Ala Asp Pro Ser Ala Asp Ser
            20                  25                  30

Val Ala Glu Ser Leu Ala Asp Leu Ala Glu Ser Val Ser Glu Leu Val
        35                  40                  45

Ser Asp Ala Asp Pro Ser Ala Asp Ser Val Ala Glu Ser Leu Ala Asp
    50                  55                  60

Leu Ala Glu Ser Val Ser Glu Leu Val Ser Asp Ala Asp Pro Ser Ala
65                  70                  75                  80

Asp Ser Val Ala Glu Ser Leu Ala Asp Leu Ala Glu Ser Val Ser Glu
                85                  90                  95

Leu Val Ser Asp Ala Asp
            100

<210> SEQ ID NO 62
<211> LENGTH: 9
<212> TYPE: PRT
<213> ORGANISM: Artificial Sequence
<220> FEATURE:
<223> OTHER INFORMATION: Synthetic

<400> SEQUENCE: 62

Cys Gly Asn Lys Arg Thr Arg Gly Cys
1               5

<210> SEQ ID NO 63
<211> LENGTH: 14
<212> TYPE: PRT
<213> ORGANISM: Artificial Sequence
<220> FEATURE:
<223> OTHER INFORMATION: Synthetic
```

```
<400> SEQUENCE: 63

Gln Gln Arg Leu Gly Asn Gln Trp Ala Val Gly His Leu Met
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Synthetic

<400> SEQUENCE: 64

Cys Arg Gly Asp Lys Arg Gly Pro Asp Glu Cys
1               5                   10

<210> SEQ ID NO 65
<211> LENGTH: 5
<212> TYPE: PRT
<213> ORGANISM: Artificial Sequence
<220> FEATURE:
<223> OTHER INFORMATION: Synthetic

<400> SEQUENCE: 65

Gly Gly Gly Gly Ser
1               5

<210> SEQ ID NO 66
<211> LENGTH: 4
<212> TYPE: PRT
<213> ORGANISM: Artificial Sequence
<220> FEATURE:
<223> OTHER INFORMATION: Synthetic

<400> SEQUENCE: 66

Gly Gly Gly Ser
1

<210> SEQ ID NO 67
<211> LENGTH: 8
<212> TYPE: PRT
<213> ORGANISM: Artificial Sequence
<220> FEATURE:
<223> OTHER INFORMATION: Synthetic

<400> SEQUENCE: 67

Ser Ile Ile Asn Phe Glu Lys Leu
1               5
```

NANOEMULSIONS

This application is the U.S. national phase of International Application No. PCT/AU2013/000630, filed 13 Jun. 2013, which designated the U.S. and claims priority to AU Application No. 2012902471, filed 13 Jun. 2012, the entire contents of each of which are hereby incorporated by reference.

FIELD OF THE INVENTION

The invention relates to nanoemulsions useful for analytical techniques and delivery of cargoes such as pharmaceutically active agents. In particular, the invention relates to nanoemulsions comprising an oil phase dispersed in an aqueous phase and at least two peptide surfactants adsorbed at the liquid-liquid interface, one peptide surfactant comprising a short peptide sequence having α-helical propensity and at least one second polypeptide surfactant comprising at least two peptide sequences having α-helical propensity linked by a linking sequence of 3 to 11 amino acid residues. Optionally the at least one second polypeptide surfactant comprises at least one pharmacokinetic modifying agent and/or a targeting agent. Furthermore, the nanoemulsion may further comprise a cargo such as a pharmaceutically active agent.

BACKGROUND OF THE INVENTION

Almost 40% of new therapeutic agents and over 30% of pipeline pharmaceuticals exhibit poor water solubility which provides challenges in delivery, such as the delivery of therapeutic levels of pharmaceuticals to achieve a desired therapeutic outcome. Furthermore, many drugs have side effect profiles that make it advantageous to be able to deliver directly to the site of action thereby minimizing the amount of drug required for a given therapeutic effect.

While liposomes, nanoemulsions and dendrimers have been used to package pharmaceuticals for delivery, they often require complex preparation procedures, use solvents not suitable for pharmaceutical use and/or result in polydisperse structures that are difficult to define and characterize to a level that allows pharmaceutical registration. Complex polymer architectures, such as dendrimers, also lack a safe history of in vivo use. Addition of pharmacokinetic modifying agents and/or targeting agents to liposomes, nanoemulsions and dendrimers adds complexity and polydispersity to these structures.

There is a need for pharmaceutical delivery carriers that are easy to prepare in the absence of non-pharmaceutical solvents, can carry a variety of pharmaceuticals, have appropriate pharmacokinetic properties including stability under biological conditions and/or deliver a pharmaceutical to a particular tissue or receptor. Additionally these pharmaceutical delivery vehicles should encapsulate or shield the pharmaceutical and deliver it in a concentrated fashion to the site of desired action, meanwhile masking it from immune clearance. There is a further need for pharmaceutical delivery carriers to deliver low amounts of pharmaceutical (e.g. antigenic protein) to specific cell types (e.g. dendritic cells) in a targeted fashion, in order to induce a sub-immunogenic activation of T cells. Alternatively, a concentrated bolus of pharmaceutical, for example a chemotherapeutic agent, should be delivered to cells again in a targeted fashion, so as to kill the target cell(s).

SUMMARY OF THE INVENTION

The present invention is predicated in part on the discovery that tailorable nanoemulsions (TNEs) comprising at least one peptide surfactant adsorbed at the liquid-liquid interface and at least one polypeptide surfactant comprising at least one pharmacokinetic modifying agent or targeting agent, were easy to prepare and improved the pharmacokinetic and/or targeting properties of the nanoemulsion.

In a first aspect, the present invention provides a nanoemulsion comprising an oil phase dispersed in an aqueous phase, at least one peptide surfactant and at least one polypeptide surfactant; wherein:

i) the at least one peptide surfactant comprising the amino acid sequence:

$$X_1\text{-}(abcdd'efg)_n\text{-}X_2$$

wherein n is an integer from 2 to 12;
amino acid residues a and d are hydrophobic amino acid residues;
amino acid residue d' is absent or is a hydrophobic amino acid residue;
at least one of residues b and c and at least one of residues e and f are hydrophilic amino acid residues and the other of amino acid residues b and c and e and f are any amino acid residue;
amino acid residue g is any amino acid residue;
$X_1$ is absent, an N-terminal capping group, an amino acid residue or a peptide of 2 to 10 amino acid residues optionally capped with an N-terminal capping group; and
$X_2$ is absent, a C-terminal capping group, an amino acid residue or a peptide of 2 to 10 amino acid residues optionally capped with a C-terminal capping group; and ii) the at least one polypeptide surfactant comprising at least two peptides having α-helical propensity linked by a linking sequence of 3 to 11 amino acid residues, wherein each peptide having α-helical propensity comprises the amino acid sequence:

$$(tuvww'xyz)_m$$

wherein m is an integer from 2 to 12;
amino acid residues t and w are hydrophobic amino acid residues;
amino acid residue w' is absent or is a hydrophobic amino acid residue;
at least one of residues u and v and at least one of residues x and y are hydrophilic amino acid residues and the other of amino acid residues u and v and x and y are any amino acid residue; and
amino acid residue z is any amino acid residue.

In some embodiments, the sequence (a b c d d' e f g)$_n$ is the same as the sequence (t u v w w' x y z)$_m$. In other embodiments, the sequence (a b c d d' e f g)$_n$ differs from the sequence (t u v w w' x y z)$_m$ by no more than 10 amino acid residues, especially where any amino acid substitution is conservative.

In some embodiments, the at least one polypeptide surfactant is conjugated to at least one pharmacokinetic modifying agent or at least one targeting agent. In some embodiments, the pharmacokinetic modifying agent is polyethylene glycol (PEG), especially where the PEG has a molecular weight of between 2000 and 25000 Da, more especially about 5000 Da. In some embodiments, the at least one polypeptide surfactant is conjugated to between 1 and 5 pharmacokinetic modifying agents. In some embodiments, the targeting agent is an antibody or fragment thereof.

In some embodiments, the nanoemulsion comprises one type of peptide surfactant and one type of polypeptide surfactant. In other embodiments, the nanoemulsion comprises one type of peptide surfactant and more than one type of polypeptide surfactant. In some embodiments, the nanoemulsion comprises more than one type of peptide surfactant and one type of polypeptide surfactant. In yet other embodiments, the nanoemulsion comprises more than one type of peptide surfactant and more than one type of polypeptide surfactant. In some embodiments, the nanoemulsion comprises a peptide surfactant and a polypeptide surfactant conjugated to a pharmacokinetic modifying agent. In some embodiments, the nanoemulsion comprises a peptide surfactant, a polypeptide surfactant conjugated to a pharmacokinetic modifying agent and a further polypeptide surfactant conjugated to a targeting agent. In some embodiments, the nanoemulsion comprises two different types of peptide surfactant and a polypeptide surfactant conjugated to a pharmacokinetic modifying agent and optionally a polypeptide surfactant or other moiety conjugated to a targeting agent.

In some embodiments, the nanoemulsion further comprises a coating comprising a polypeptide surfactant conjugated to a pharmacokinetic modifying agent. In some embodiments, the nanoemulsion further comprises a pharmaceutically active agent. In particular embodiments, the pharmaceutically active agent is sparingly soluble in aqueous solution and is incorporated into the oil phase of the nanoemulsion. In other embodiments, the pharmaceutically active agent is soluble in aqueous solution and is incorporated into the nanoemulsion as a solid particulate, for example, a solid-in-oil nanodispersion. In a particular embodiment, the pharmaceutically active agent is a protein antigen.

In another aspect of the invention there is provided a method of preparing a nanoemulsion of the invention comprising the steps of:

1. providing an oil phase and an aqueous phase, said aqueous phase comprising a peptide comprising the amino acid sequence:

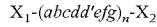

X$_1$-(abcdd'efg)$_n$-X$_2$ wherein n is an integer from 2 to 12;
amino acid residues a and d are hydrophobic amino acid residues;
amino acid residue d' is absent or is a hydrophobic amino acid residue;
at least one of residues b and c and at least one of residues e and f are hydrophilic amino acid residues and the other of amino acid residues b and c and e and f are any amino acid residue;
amino acid residue g is any amino acid residue;
X$_1$ is absent, an N-terminal capping group, or an amino acid residue or a peptide of 2 to 10 amino acid residues an optionally capped with an N-terminal capping group; and
X$_2$ is absent, a C-terminal capping group, or an amino acid residue or a peptide of 2 to 10 amino acid residues optionally capped with a C-terminal capping group;

2. mixing the oil phase and aqueous phase to provide a nanoemulsion;

3. adding to the nanoemulsion formed in step 2, a polypeptide surfactant comprising at least two peptides having α-helical propensity linked by a linking sequence of 3 to 11 amino acid residues, wherein each peptide having α-helical propensity comprises the amino acid sequence:

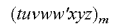

(tuvww'xyz)$_m$ wherein m is an integer from 2 to 12;
amino acid residues t and w are hydrophobic amino acid residues;
amino acid residue w' is absent or is a hydrophobic amino acid residue;
at least one of residues u and v and at least one of residues x and y are hydrophilic amino acid residues and the other of amino acid residues u and v and x and y are any amino acid residue; and
amino acid residue z is any amino acid residue;

4. mixing the mixture of step 3 to provide a nanoemulsion.

In yet another aspect of the invention there is provided a polypeptide surfactant comprising at least two peptides having α-helical propensity linked by a linking sequence of 3 to 11 amino acid residues, wherein each peptide having α-helical propensity comprises the amino acid sequence:

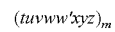

(tuvww'xyz)$_m$ wherein m is an integer from 2 to 12;
amino acid residues t and w are hydrophobic amino acid residues;
amino acid residue w' is absent or is a hydrophobic amino acid residue;
at least one of residues u and v and at least one of residues x and y are hydrophilic amino acid residues and the other of amino acid residues u and v and x and y are any amino acid residue; and
amino acid residue z is any amino acid residue;
wherein the polypeptide surfactant is conjugated to at least one pharmacokinetic modifying agent or a targeting agent.

In another aspect of the invention there is provided a use of a nanoemulsion as an analytical standard, said nanoemulsion comprising an oil phase dispersed in an aqueous phase, at least one peptide surfactant and at least one polypeptide surfactant; wherein:

i) the at least one peptide surfactant comprising the amino acid sequence:

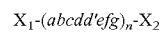

X$_1$-(abcdd'efg)$_n$-X$_2$ wherein n is an integer from 2 to 12;
amino acid residues a and d are hydrophobic amino acid residues;
amino acid residue d' is absent or is a hydrophobic amino acid residue;
at least one of residues b and c and at least one of residues e and f are hydrophilic amino acid residues and the other of amino acid residues b and c and e and f are any amino acid residue;
amino acid residue g is any amino acid residue;
X$_1$ is absent, an N-terminal capping group, an amino acid residue or a peptide of 2 to 10 amino acid residues optionally capped with an N-terminal capping group; and
X$_2$ is absent, a C-terminal capping group, an amino acid residue or a peptide of 2 to 10 amino acid residues optionally capped with a C-terminal capping group; and ii) the at least one polypeptide surfactant comprising at least two peptides having α-helical propensity linked by a linking sequence of 3 to 11 amino acid residues, wherein each peptide having α-helical propensity comprises the amino acid sequence:

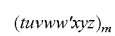

(tuvww'xyz)$_m$ wherein m is an integer from 2 to 12;

amino acid residues t and w are hydrophobic amino acid residues;

amino acid residue w' is absent or is a hydrophobic amino acid residue;

at least one of residues u and v and at least one of residues x and y are hydrophilic amino acid residues and the other of amino acid residues u and v and x and y are any amino acid residue; and amino acid residue z is any amino acid residue.

In some embodiments, the at least one polypeptide surfactant is conjugated to at least one pharmacokinetic modifying agent. In some embodiments, the pharmacokinetic modifying agent is polyethylene glycol (PEG), especially where the PEG has a molecular weight of between 2000 and 25000 Da, more especially about 5000 Da. In some embodiments, the at least one polypeptide surfactant is conjugated to between 1 and 5 pharmacokinetic modifying agents.

DESCRIPTION OF THE INVENTION

Definitions

Figure 1:
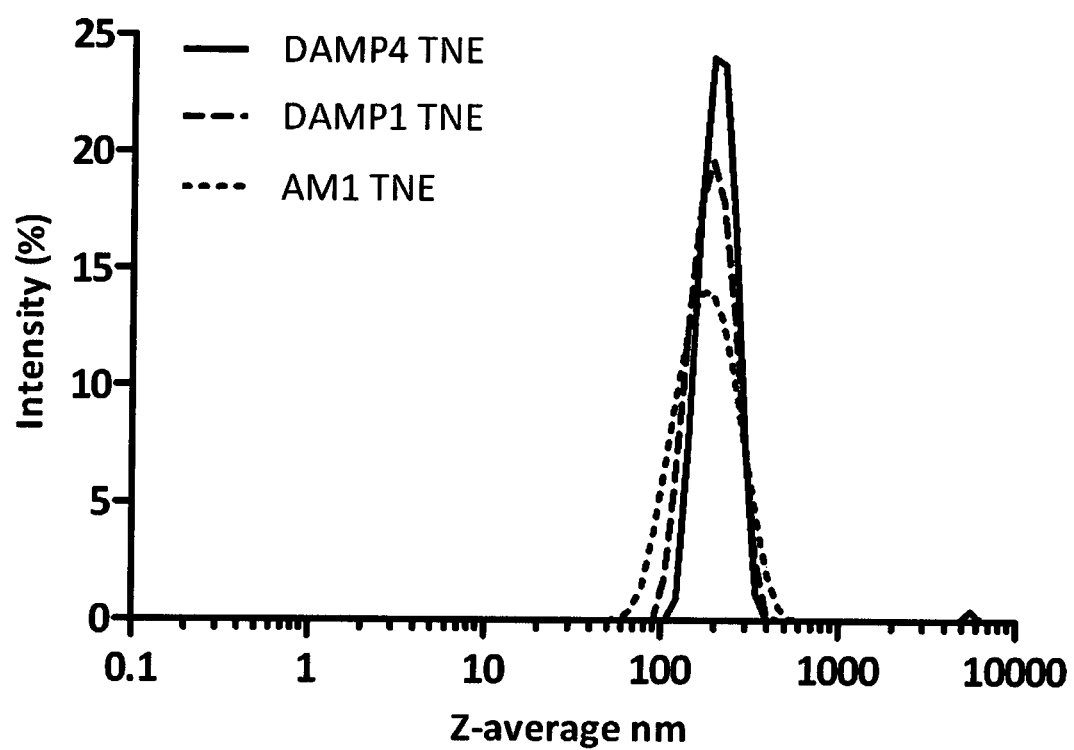
FIG. 1 is a graphical representation showing droplet size distributions of tailorable nanoemulsions (TNEs) prepared from SEQ ID NO:1 (AM1, - - - ), SEQ ID NO:2 (DAMP1, —— - ) and SEQ ID NO:32 (DAMP4, ____).

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 30%, 20%, or 10% to a reference quantity, level, value, dimension, size, or amount.

The term "amphiphilic" refers to molecules having both hydrophilic and hydrophobic regions. The term amphiphilic is synonymous with "amphipathic" and these terms may be used interchangeably.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The term "hydrophilic" refers to a molecule or portion of a molecule that is attracted to water and other polar solvents. A hydrophilic molecule or portion of a molecule is polar and/or charged or has an ability to form interactions such as hydrogen bonds with water or polar solvents.

The term "hydrophobic" refers to a molecule or portion of a molecule that repels or is repelled by water and other polar solvents. A hydrophobic molecule or portion of a molecule is non-polar, does not bear a charge and is attracted to non-polar solvents.

As used herein, the terms "peptide", "polypeptide" and "protein" refer to two or more naturally occurring or non-naturally occurring amino acids joined by peptide bonds. While there are no rules that govern the boundaries between these terms, generally peptides contain less amino acid residues than polypeptides and polypeptides contain less amino acid residues than proteins.

As used herein, the term "amino acid" refers to an α-amino acid or a β-amino acid and may be a L- or D-isomer. The amino acid may have a naturally occurring side chain (see Table 1) or a non-naturally occurring side chain (see Table 2). The amino acid may also be further substituted in the α-position or the β-position with a group selected from —$C_1$-$C_6$alkyl, —$(CH_2)_nCOR_1$, —$(CH_2)_nR_2$, —$PO_3H$, —$(CH_2)_n$heterocyclyl or —$(CH_2)_n$aryl where $R_1$ is —OH, —$NH_2$, —$NHC_1$-$C_3$alkyl, —$OC_1$-$C_3$alkyl or —$C_1$-$C_3$alkyl and $R_2$ is —OH, —SH, —$SC_1$-$C_3$alkyl, —$OC_1$-$C_3$alkyl, —$C_3$-$C_{12}$cycloalkyl, —$NH_2$, —$NHC_1$-$C_3$alkyl or —NHC(C=NH)$NH_2$ and where each alkyl, cycloalkyl, aryl or heterocyclyl group may be substituted with one or more groups selected from —OH, —$NH_2$, —$NHC_1$-$C_3$alkyl, —$OC_1$-$C_3$alkyl, —SH, —$SC_1$-$C_3$alkyl, —$CO_2H$, —$CO_2C_1$-$C_3$alkyl, —$CONH_2$ or —$CONHC_1$-$C_3$alkyl.

Amino acid structure and single and three letter abbreviations used throughout the specification are defined in Table 1, which lists the twenty naturally occurring amino acids which occur in proteins as L-isomers.

TABLE 1

(1)

| Amino Acid | Three-letter Abbreviation | One-letter symbol | Structure of side chain (R) |
|---|---|---|---|
| Alanine | Ala | A | —$CH_3$ |
| Arginine | Arg | R | —$(CH_2)_3NHC(=N)NH_2$ |
| Asparagine | Asn | N | —$CH_2CONH_2$ |
| Aspartic acid | Asp | D | —$CH_2CO_2H$ |
| Cysteine | Cys | C | —$CH_2SH$ |
| Glutamine | Gln | Q | —$(CH_2)_2CONH_2$ |
| Glutamic acid | Glu | E | —$(CH_2)_2CO_2H$ |
| Glycine | Gly | G | —H |
| Histidine | His | H | —$CH_2$(4-imidazolyl) |
| Isoleucine | Ile | I | —$CH(CH_3)CH_2CH_3$ |
| Leucine | Leu | L | —$CH_2CH(CH_3)_2$ |
| Lysine | Lys | K | —$(CH_2)_4NH_2$ |
| Methionine | Met | M | —$(CH_2)_2SCH_3$ |
| Phenylalanine | Phe | F | —$CH_2Ph$ |
| Proline | Pro | P | see formula (2) above for structure of amino acid |
| Serine | Ser | S | —$CH_2OH$ |
| Threonine | Thr | T | —$CH(CH_3)OH$ |
| Tryptophan | Trp | W | —$CH_2$(3-indolyl) |
| Tyrosine | Tyr | Y | —$CH_2$(4-hydroxyphenyl) |
| Valine | Val | V | —$CH(CH_3)_2$ |

The term "α-amino acid" as used herein, refers to a compound having an amino group and a carboxyl group in which the amino group and the carboxyl group are separated by a single carbon atom, the α-carbon atom. An α-amino acid includes naturally occurring and non-naturally occurring L-amino acids and their D-isomers and derivatives thereof such as salts or derivatives where functional groups are protected by suitable protecting groups. The α-amino acid may also be further substituted in the α-position with a group selected from —$C_1$-$C_6$alkyl, —$(CH_2)_nCOR_1$, —$(CH_2)_nR_2$, —$PO_3H$, —$(CH_2)_n$heterocyclyl or —$(CH_2)_n$aryl where $R_1$ is —OH, —$NH_2$, —$NHC_1$-$C_3$alkyl, —$OC_1$-$C_3$alkyl or —$C_1$-$C_3$alkyl and $R_2$ is —OH, —SH, —$SC_1$-$C_3$alkyl, —$OC_1$-$C_3$alkyl, —$C_3$-$C_{12}$cycloalkyl, —$NH_2$, —$NHC_1$-$C_3$alkyl or —NHC(C=NH)$NH_2$ and where each alkyl, cycloalkyl, aryl or heterocyclyl group may be substituted with one or more groups selected from —OH, —$NH_2$, —$NHC_1$-$C_3$alkyl, —$OC_1$-$C_3$alkyl, —SH, —$SC_1$-$C_3$alkyl, —$CO_2H$, —$CO_2C_1$-$C_3$alkyl, —$CONH_2$ or —$CONHC_1$-$C_3$alkyl.

As used herein, the term "β-amino acid" refers to an amino acid that differs from an α-amino acid in that there are two (2) carbon atoms separating the carboxyl terminus and the amino terminus. As such, β-amino acids with a specific side chain can exist as the R or S enantiomers at either of the α (C2) carbon or the β (C3) carbon, resulting in a total of 4 possible isomers for any given side chain. The side chains may be the same as those of naturally occurring α-amino acids (see Table 1 above) or may be the side chains of non-naturally occurring amino acids (see Table 2 below).

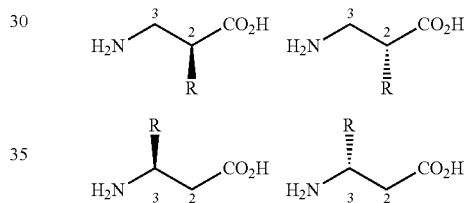

Furthermore, the β-amino acids may have mono-, di-, tri- or tetra-substitution at the C2 and C3 carbon atoms. Mono-substitution may be at the C2 or C3 carbon atom. Di-substitution includes two substituents at the C2 carbon atom, two substituents at the C3 carbon atom or one substituent at each of the C2 and C3 carbon atoms. Tri-substitution includes two substituents at the C2 carbon atom and one substituent at the C3 carbon atom or two substituents at the C3 carbon atom and one substituent at the C2 carbon atom. Tetra-substitution provides for two substituents at the C2 carbon atom and two substituents at the C3 carbon atom. Suitable substituents include —$C_1$-$C_6$alkyl, —$(CH_2)_nCOR_1$, —$(CH_2)_nR_2$, —$PO_3H$, —$(CH_2)_n$heterocyclyl or —$(CH_2)_n$aryl where $R_1$ is —OH, —$NH_2$, —$NHC_1$-$C_3$alkyl, —$OC_1$-$C_3$alkyl or —$C_1$-$C_3$alkyl and $R_2$ is —OH, —SH, —$SC_1$-$C_3$alkyl, —$OC_1$-$C_3$alkyl, —$C_3$-$C_{12}$cycloalkyl, —$NH_2$, —$NHC_1$-$C_3$alkyl or —NHC(C=NH)$NH_2$ and where each alkyl, cycloalkyl, aryl or heterocyclyl group may be substituted with one or more groups selected from —OH, —$NH_2$, —$NHC_1$-$C_3$alkyl, —$OC_1$-$C_3$alkyl, —SH, —$SC_1$-$C_3$alkyl, —$CO_2H$, —$CO_2C_1$-$C_3$alkyl, —$CONH_2$ or —$CONHC_1$-$C_3$alkyl.

Other suitable β-amino acids include conformationally constrained β-amino acids. Cyclic β-amino acids are conformationally constrained and are generally not accessible to enzymatic degradation. Suitable cyclic β-amino acids include, but are not limited to, cis- and trans-2-aminocyclopropyl carboxylic acids, 2-aminocyclobutyl and cyclobutenyl carboxylic acids, 2-aminocyclopentyl and cyclopentenyl carboxylic acids, 2-aminocyclohexyl and cyclohexenyl carboxylic acids and 2-amino-norbornane carboxylic acids and their derivatives, some of which are shown below:

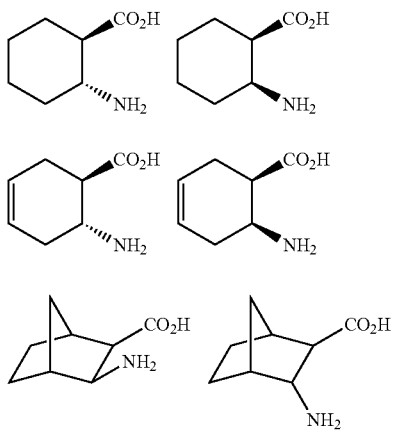

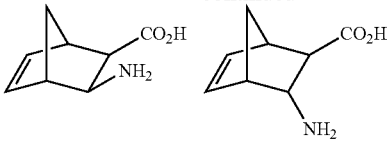

Suitable derivatives of β-amino acids include salts and may have functional groups protected by suitable protecting groups.

The term "non-naturally occurring amino acid" as used herein, refers to amino acids having a side chain that does not occur in the naturally occurring L-α-amino acids. Examples of non-natural amino acids and derivatives include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, citrulline, sarcosine, 4-amino-3-hydroxy-6-methylheptanoic acid, 2-thienyl alanine and/or D-isomers of amino acids. A list of unnatural amino acids that may be useful herein is shown in Table 2.

TABLE 2

| Non-Conventional amino acid | Code | Non-Conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisoleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |

TABLE 2-continued

| Non-Conventional amino acid | Code | Non-Conventional amino acid | Code |
|---|---|---|---|
| D-N-methylasparagine | Dnmasn | N-cycloundecylglycine | Ncund |
| D-N-methylasparatate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylethyl)glycine | Nhtrp |
| D-N-methyllysine | Dnmlys | N-methyl-y-aminobutyrate | Nmgabu |
| N-methylcyclohexylalanine | Nmchexa | D-N-methylmethionine | Dnmmet |
| D-N-methylorinithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methylnapthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylasparate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenylethylamino)cyclopropane | Nmbc | | |

The term "alkyl" as used herein refers to straight chain or branched hydrocarbon groups. Suitable alkyl groups include, but are not limited to methyl, ethyl, propyl, isopropyl, butyl, isobutyl, pentyl, hexyl, heptyl, octyl, nonyl, decyl, dodecyl, tetradecyl, hexadecyl and octadecyl. The term alkyl may be prefixed by a specified number of carbon atoms to indicate the number of carbon atoms or a range of numbers of carbon atoms that may be present in the alkyl group. For example, $C_1$-$C_3$alkyl refers to methyl, ethyl, propyl and isopropyl.

The term "cycloalkyl" as used herein, refers to cyclic hydrocarbon groups. Suitable cycloalkyl groups include, but are not limited to, cyclopropyl, cyclobutyl, cyclopentyl, cyclohexyl, cycloheptyl, cyclooctyl, cyclononyl, cyclodecyl, cycloundecyl and cyclododecyl.

The term "heterocyclyl" as used herein refers to 5 or 6 membered saturated, partially unsaturated or aromatic cyclic hydrocarbon groups in which at least one carbon atom has been replaced by N, O or S. Optionally, the heterocyclyl group may be fused to a phenyl ring. Suitable heterocyclyl groups include, but are not limited to pyrrolidinyl, piperidinyl, pyrrolyl, thiophenyl, furanyl, oxazolyl, imidazolyl, thiazolyl, isoxazolyl, pyrazolyl, isothiazolyl, pyridinyl, quinolinyl, isoquinolinyl, indolyl, benzofuranyl, benzothiophenyl, oxadiazolyl, tetrazolyl, triazolyl and pyrimidinyl.

The term "aryl" as used herein, refers to $C_6$-$C_{10}$ aromatic hydrocarbon groups, for example phenyl and naphthyl.

The term "alkylene" as used herein refers to a divalent saturated carbon containing chain —$(CH_2)_q$—. The alkylene group may have any number of —$CH_2$— groups, especially 1 to 20 —$CH_2$— groups in the chain, more especially 1 to 15 or 1 to 10 —$CH_2$— groups in the chain. The term "alkenylene" similarly refers to a divalent unsaturated carbon containing chain in which the unsaturation is at least one double bond. Similarly, the term "alkynylene" refers to a divalent unsaturated carbon containing chain in which the unsaturation is at least one triple bond. While the number of atoms in the alkenylene or alkynylene group is not particularly limited, they preferably have 2 to 20 carbon atoms, especially 2 to 15 or 2 to 10 carbon atoms.

The term "α-helix breaking amino acid residue" refers to an amino acid residue that has a low frequency of occurrence in known α-helical conformations and which promotes termination of an α-helix. α-Helix breaking amino acid residues may lack an amide hydrogen to participate in hydrogen bonding within the helix or may be too conformationally flexible or inflexible to form the constrained α-helical conformation in an energy efficient manner. Examples of α-helix breaking amino acid residues include, but are not limited to proline and glycine.

The term "hydrophilic amino acid residue" as used herein refers to an amino acid residue in which the side chain is polar or charged. Examples include glycine, L-serine, L-threonine, L-cysteine, L-tyrosine, L-asparagine, L-glutamine, L-aspartic acid, L-glutamic acid, L-lysine, L-arginine, L-histidine, L-ornithine, D-serine, D-threonine, D-cysteine, D-tyrosine, D-asparagine, D-glutamine, D-aspartic acid, D-glutamic acid, D-lysine, D-arginine, D-histidine and D-ornithine, especially L-serine, L-threonine, L-cysteine, L-tyrosine, L-asparagine, L-glutamine, L-aspartic acid, L-glutamic acid, L-lysine, L-arginine, L-histidine and L-ornithine.

As used herein, the term "hydrophobic amino acid residue" refers to an amino acid residue in which the side chain is non-polar. Examples include, but are not limited to L-alanine, L-valine, L-leucine, L-isoleucine, L-proline, L-methionine, L-phenylalanine, L-tryptophan, L-aminoisobutyric acid, D-alanine, D-valine, D-leucine, D-isoleucine, D-proline, D-methionine, D-phenylalanine, D-tryptophan, D-aminoisobutyric acid, L-cyclohexylalanine, D-cyclohexylalanine, L-cyclopentylalanine, D-cyclopentylalanine, L-norleucine, D-norleucine, L-norvaline, D-norvaline, L-tert-butylglycine, D-tert-butylglycine, L-ethylglycine and D-ethylglycine, especially L-alanine, L-valine, L-leucine, L-isoleucine, L-proline, L-methionine, L-phenylalanine, L-tryptophan and L-aminoisobutyric acid.

As used herein, the term "positively charged amino acid residue" refers to an amino acid residue having a side chain capable of bearing a positive charge. Examples include, but are not limited to L-lysine, L-arginine, L-histidine, L-ornithine, D-lysine, D-arginine, D-histidine and D-ornithine.

As used herein, the term "negatively charged amino acid residue" refers to an amino acid residue having a side chain capable of bearing a negative charge. Examples include, but are not limited to L-aspartic acid, L-glutamic acid, D-aspartic acid and D-glutamic acid.

As used herein, the term "polar amino acid residue" refers to an amino acid residue having a side chain that has a dipole moment. Examples of polar amino acid residues, include, but are not limited to glycine, L-serine, L-threonine, L-cysteine, L-tyrosine, L-asparagine, L-glutamine, D-serine, D-threonine, D-cysteine, D-tyrosine, D-asparagine and D-glutamine.

The term "amino acid having a small side chain" refers to amino acid residues having a side chain with 4 or less non-hydrogen atoms, especially 3 or less non-hydrogen atoms.

Examples include, but are not limited to, glycine, L-alanine, L-valine, L-leucine, L-isoleucine, L-methionine, L-serine, L-threonine, L-cysteine, L-asparagine, L-aspartic acid, D-alanine, D-valine, D-leucine, D-isoleucine, D-methionine, D-serine, D-threonine, D-cysteine, D-asparagine and D-aspartic acid, especially glycine, L-alanine, L-valine, L-serine, L-threonine and L-cysteine.

The term "conservative amino acid substitution" refers to substituting one amino acid in a sequence with another amino acid that has similar properties of size, polarity and/or aromaticity and does not change the nature of activity of the peptide. For example, one polar amino acid residue may be substituted with another polar amino acid residue or an amino acid residue having a small side chain may be substituted with another amino acid residue having a small side chain.

The term "α-helical propensity" refers to a peptide that includes amino acid residues that favour formation of an α-helical structure. While the peptides may form helices under conditions that favour helix formation, for example, at a liquid-liquid interface, under other conditions that do not favour helix formation, such as in a bulk aqueous solution, they may lack a high content of well defined secondary structure. The propensity of a peptide to form an α-helix can be determined using titration with 2,2,2-trifluoroethanol as known in the art (Jasonoff and Fersht, *Biochemistry*, 1994, 23(8):2129-35).

The term "liquid-liquid interface" refers to the region forming the common boundary between the immiscible liquids, the oil phase and polar phase, in the nanoemulsion.

The term "self-assembled" refers to a population of peptide or polypeptide surfactant molecules with an affinity for the liquid-liquid interface and which relocate themselves from the bulk solution to the liquid-liquid interface.

The solubility of a drug as used herein as defined in Table 3:

TABLE 3

Values for estimating drug solubility based upon "USP definition"*

| Descriptive Term | Appropriate Volume of Solvent In Milliliters Per Gram of Solute |
|---|---|
| Very soluble | Less than 1 part solvent needed to dissolve 1 part solute |
| Freely soluble | From 1 to 10 parts solvent needed to dissolve 1 part solute |
| Soluble | From 10 to 30 parts solvent needed to dissolve 1 part solute |
| Sparingly soluble | From 30 to 100 parts solvent needed to dissolve 1 part solute |
| Slightly soluble | From 100 to 1000 parts solvent needed to dissolve 1 part solute |
| Very slightly soluble | From 1000 to 10,000 parts solvent needed to dissolve 1 part solute |
| Practically insoluble | More than 10,000 parts solvent needed to dissolve 1 part solute |

*The United Stated Pharmacopeia, USP 26, NF 21, 2003.

Nanoemulsions

The nanoemulsions of the present invention comprise at least one peptide surfactant and at least one polypeptide surfactant at the liquid-liquid interface.

The peptide surfactant comprises an amino acid sequence:

$$X_1\text{-}(abcdd'efg)_n\text{-}X_2 \qquad (I)$$

wherein n is an integer from 2 to 12;
amino acid residues a and d are hydrophobic amino acid residues;
amino acid residue d' is absent or is a hydrophobic amino acid residue;
at least one of residues b and c and at least one of residues e and f are hydrophilic amino acid residues and the other of amino acid residues b and c and e and f are any amino acid residue;
amino acid residue g is any amino acid residue;
$X_1$ is absent, an N-terminal capping group, an amino acid residue or a peptide of 2 to 10 amino acid residues optionally capped with an N-terminal capping group; and
$X_2$ is absent, a C-terminal capping group, an amino acid residue or a peptide of 2 to 10 amino acid residues optionally capped with a C-terminal capping group.

In the peptide n is 2 to 12, especially 2 to 6, more especially 2 to 5. In some embodiments n is 3 or 4.

In some embodiments, at least a portion of the peptide surfactant having α-helical propensity comprises hydrophobic and hydrophilic groups that can partition at a liquid-liquid interface to create an amphiphilic structure having a hydrophobic face and a hydrophilic face. This amphiphilic character provides the peptide with an affinity for the liquid-liquid interface such that the peptide self-assembles at the liquid-liquid interface.

In some embodiments, $X_1$ is absent, an amino acid residue, a peptide of 2 to 6 amino acid residues or an N-terminal capping group. In some embodiments, $X_1$ is absent leaving a free N-terminus. In other embodiments, when $X_1$ is an amino acid residue it may be any amino acid residue but especially one that is α-helix breaking such as glycine. When $X_1$ is a peptide, it is preferably a flexible peptide, optionally comprising an amino acid that is α-helix breaking. In some embodiments, $X_1$ comprises at least one glycine or proline, alanine or serine residue. In some embodiments $X_1$ is GlyGlyGlyGlySer-, GlySerGlySer- or $(Ala)_{1-6}$.

As used herein, the N-terminal capping group, when present, is any group that blocks the reactivity of the N-terminal amino group. Suitable examples include acyl groups such as acetyl (ethanoyl), propanoyl, butanoyl, pentanoyl and hexanoyl, especially acetyl.

In some embodiments, $X_2$ is absent, an amino acid residue, a peptide of 2 to 6 amino acid residues or a C-terminal capping group. Some embodiments, $X_2$ is absent leaving a free C-terminal carboxyl group. In other embodiments, when $X_2$ is an amino acid, it may be any amino acid residue but especially an α-helix breaking residue such as glycine or proline. When $X_2$ is a peptide it is preferably a flexible peptide optionally comprising an α-helix breaking residue such as glycine. In some embodiments $X_2$ comprises at least one glycine, serine or alanine residue. In some embodiments, $X_2$ is GlyGlyGlyGlySer-, GlySerGlySer- or $(Ala)_{1-6}$.

As used herein, the C-terminal capping group, when present, is any suitable group that blocks the reactivity of the C-terminal carboxyl group. Suitable examples include amino groups thereby forming an amide. Examples include —$NH_2$, —NH(alkyl) and —$NH(alkyl)_2$.

In some embodiments where $X_1$ and $X_2$ are an amino acid residue or a peptide, the number of amino acid residues in $X_1+X_2$ is between 2 and 11, especially 2 and 6, more especially 3.

In some embodiments, one of $X_1$ and $X_2$ is absent and the other is present. In other embodiments, both of $X_1$ and $X_2$ are absent. In yet other embodiments, $X_1$ and $X_2$ are present.

In other embodiments, $X_1$ comprises an amino acid residue that is an α-helix-breaking amino acid residue such as proline or glycine, especially a proline residue. In some embodiments, $X_1$ comprises a peptide P-X where X is any amino acid, especially a small amino acid. In some embodiments P-X comprises a peptide P-S or consists of the peptide P-S.

In some embodiments, $X_2$ comprises an amino acid residue or peptide, especially a small amino acid residue such as a serine, glycine, cysteine or threonine residue, or a negatively charged amino acid residue such as aspartic acid or glutamic acid, especially an aspartic acid residue or a serine residue. In some embodiments, $X_2$ consists of an aspartic acid residue.

In any embodiment where $X_1$ or $X_2$ is an amino acid or peptide, the N-terminal and/or C-terminal amino acid of $X_1$ and $X_2$ are optionally capped with an N-terminal capping group or C-terminal capping group respectively.

Amino acid residues a and d are hydrophobic amino acid residues. In some embodiments, amino acid residues a and d are independently selected from L-alanine, L-valine, L-leucine, L-methionine, L-isoleucine, L-phenylalanine, L-tyrosine, D-alanine, D-valine, D-leucine, D-methionine, D-isoleucine, D-phenylalanine, D-tyrosine, especially L-alanine, L-methionine, L-valine and L-leucine.

Amino acid residue d' may be absent or may be a hydrophobic amino acid residue. The residue d' may be included in longer sequences, for example, where n is 3, 6, 9 or 12, to counteract perturbations in helix turn when a helix is formed, that may result in misalignment of the hydrophobic residues on one face of the helix. In some embodiments, d' is present in the third, sixth, ninth and/or twelfth sequence of $(a\ b\ c\ d\ d'\ e\ f\ g)_n$ when n is 3, 6, 9 and 12, but is absent in the other (a b c d d' e f g) sequences in a peptide having α-helical propensity. In some embodiments, when present, amino acid d' may be selected from L-alanine, L-valine, L-leucine, L-methionine, L-isoleucine, L-phenylalanine, L-tyrosine, D-alanine, D-valine, D-leucine, D-methionine, D-isoleucine, D-phenylalanine, D-tyrosine, especially L-alanine, L-methionine, L-valine and L-leucine.

At least one of b and c is a hydrophilic amino acid residue, such as L-serine, L-threonine, L-cysteine, L-tyrosine, L-asparagine, L-glutamine, L-aspartic acid, L-glutamic acid, L-lysine, L-histidine, L-ornithine, D-serine, D-threonine, D-cysteine, D-tyrosine, D-asparagine, D-glutamine, D-aspartic acid, D-glutamic acid, D-lysine, D-histidine and D-ornithine, especially L-serine, L-threonine, L-cysteine, L-tyrosine, L-asparagine, L-glutamine, L-aspartic acid, L-glutamic acid, L-lysine, L-histidine and L-ornithine. The other one of amino acid residues b and c is any amino acid residue, especially an amino acid residue that has a propensity to form α-helices, such as alanine, lysine, uncharged glutamic acid, methionine, leucine and aminoisobutyric acid or a small amino acid residue such as alanine, serine, valine, leucine or isoleucine, or a hydrophilic amino acid residue such as glutamine, asparagine, serine, glutamic acid and aspartic acid, provided that b and c are not both charged amino acid residues that have the same charge.

At least one of e and f is a hydrophilic amino acid residue, such as L-serine, L-threonine, L-cysteine, L-tyrosine, L-asparagine, L-glutamine, L-aspartic acid, L-glutamic acid, L-lysine, L-histidine, L-ornithine, D-serine, D-threonine, D-cysteine, D-tyrosine, D-asparagine, D-glutamine, D-aspartic acid, D-glutamic acid, D-lysine, D-histidine and D-ornithine, especially L-serine, L-threonine, L-cysteine, L-tyrosine, L-asparagine, L-glutamine, L-aspartic acid, L-glutamic acid, L-lysine, L-histidine and L-ornithine. The other one of amino acid residues e and f is any amino acid residue, especially an amino acid residue that has a propensity to form α-helices, such as alanine, lysine, uncharged glutamic acid, methionine, leucine and aminoisobutyric acid or a small amino acid residue such as alanine, serine, valine, leucine or isoleucine, or a hydrophilic amino acid residue such as glutamine, asparagine, serine, glutamic acid and aspartic acid, provided that e and f are not both charged amino acid residues that have the same charge.

Amino acid residue g may be any amino acid residue. In particular embodiments, amino acid residue g is a residue that has a propensity to form α-helices, such as alanine, lysine, uncharged glutamic acid, methionine, leucine and aminoisobutyric acid, especially alanine, lysine and uncharged glutamic acid; or amino acid residues that are not detrimental to α-helix formation, for example, amino acid residues other than proline and glycine.

In some embodiments, each amino acid residue b is independently selected from a small hydrophobic amino acid residue, such as alanine, leucine, valine, methionine and isoleucine, or a hydrophilic amino acid residue, especially a polar or charged amino acid residue such as L-serine, L-threonine, L-cysteine, L-tyrosine, L-asparagine, L-glutamine, L-lysine, L-arginine, L-histidine, aspartic acid or glutamic acid. In some embodiments, each b is independently selected from L-lysine, L-histidine, L-serine, L-alanine, L-asparagine and L-glutamine.

In some embodiments, each amino acid residue c is independently selected from a polar, positively charged or negatively charged amino acid residue, such as L-serine, L-threonine, L-cysteine, L-tyrosine, L-asparagine, L-glutamine, L-lysine, L-arginine, L-histidine, L-aspartic acid or L-glutamic acid. In some embodiments, each c is independently selected from L-glutamine, L-arginine, L-serine, L-glutamic acid and L-asparagine.

Each amino acid residue e is independently any amino acid residue and may be hydrophobic or hydrophilic. In some embodiments, each e is independently selected from L-alanine, L-valine, L-leucine, L-isoleucine, L-serine, L-threonine, L-aspartic acid and L-glutamic acid, especially L-alanine, L-serine and L-glutamic acid.

In some embodiments, each amino acid residue f is a polar, positively charged or negatively charged amino acid residue, such as L-serine, L-threonine, L-cysteine, L-tyrosine, L-asparagine, L-glutamine, L-lysine, L-arginine, L-histidine, L-aspartic acid or L-glutamic acid. In some embodiments, each f is independently selected from L-aspartic acid, L-glutamic acid, L-arginine, L-glutamine, L-histidine, L-lysine and L-asparagine.

Amino acid residue g is independently any amino acid residue and may be hydrophobic or hydrophilic. In some embodiments, the residue g is independently selected from a small hydrophobic residue or a charged or polar uncharged residue. In some embodiments, each g is independently selected from L-alanine, L-valine, L-leucine, L-isoleucine, L-serine, L-threonine, L-asparagine L-lysine, L-glutamic acid and L-glutamine, especially L-alanine, L-serine and L-glutamine.

In some embodiments, the peptide surfactant is a peptide selected from one of the following sequences:

```
SEQ ID NO: 1:
Ac-MKQLADS-LHQLARQ-VSRLEHA-CONH₂ (AM1)

SEQ ID NO: 2:
PS-MKQLADS-LHQLARQ-VSRLEHA-D (DAMP1)

SEQ ID NO: 3:
Ac-MKQLADS-LMQLARQ-VSRLESA-CONH₂

SEQ ID NO: 4:
Ac-LMQLARQ-MKQLADS-LMQLARQ-VSRLESA-CONH₂

SEQ ID NO: 5:
Ac-MKELADS-LMQLARQ-VDRLESA-CONH₂

SEQ ID NO: 6:
Ac-MKQLADS-LHQLAHQ-VSHLEHA-CONH₂

SEQ ID NO: 7:
Ac-MEELADS-LEELARQ-VEELESA-CONH₂

SEQ ID NO: 8:
Ac-MKKLADS-LKKLARQ-VKKLESA-CONH₂

SEQ ID NO: 9:
Ac-MKQLADS-LHQLAHK-VSHLEHA-CONH₂

SEQ ID NO: 10:
Ac-EISALEK-EISALEK-EISALEK-CONH₂

SEQ ID NO: 11:
Ac-KISALKE-KISALKE-KISALKE-CONH₂

SEQ ID NO: 12:
PS-MKELADS-LHELARE-VSRLEHA-D

SEQ ID NO: 13:
PS-MKELADS-LHQLARQ-VSRLEHA-D

SEQ ID NO: 14:
PS-MKQLADS-LHELARQ-VSRLEHA-D

SEQ ID NO: 15:
PS-MKQLADS-LHQLARQ-VSRLEHA-D

SEQ ID NO: 16:
PS-MKELADS-LHELARQ-VSRLEHA-D

SEQ ID NO: 17:
PS-MKELADS-LHQLARE-VSRLEHA-D

SEQ ID NO: 18:
PS-MKQLADS-LHELARE-VSRLEHA-D

SEQ ID NO: 19:
PS-AKSLAES-LHSLARS-VSRLEHA-D

SEQ ID NO: 20:
PS-AKSVAES-LHSLARS-VSRLVEHA-D

SEQ ID NO: 21:
PS-AHSVAES-LHSLARS-VSRLVEHA-D

SEQ ID NO: 22:
PS-AHSVAKS-LHSLARS-VSRLVSHA-D

SEQ ID NO: 23:
PS-AHSVAES-LHSLAES-VSELVSHA-D

SEQ ID NO: 24:
PS-AQSVAQS-LAQLAQS-VSQLVSQA-D

SEQ ID NO: 25:
PS-AESVAES-LAELAES-VSELVSEA-D

SEQ ID NO: 26:
PS-ANSVANS-LANLANS-VSNLVSNA-D

SEQ ID NO: 27:
PS-ADSVADS-LADLADS-VSPLVSDA-D

SEQ ID NO: 28:
PS-AQSVAES-LAQLAES-VSELVSQA-D

SEQ ID NO: 29:
PS-AESVAES-LAELAES-VSELVSEA-D

SEQ ID NO: 30:
PS-ANSVAES-LANLAES-VSELVSNA-D

SEQ ID NO: 31:
PS-ADSVAES-LADLAES-VSELVSDA-D.
```

The peptide surfactant may be prepared by methods such as solid phase or solution phase synthesis as known in the art.

The polypeptide surfactant is a polypeptide comprising at least two peptides having α-helical propensity linked by a linking sequence of 3 to 11 amino acid residues, wherein each peptide having α-helical propensity comprises the amino acid sequence:

$$(tuvww'xyz)_m$$

wherein m is an integer from 2 to 12;
amino acid residues t and w are hydrophobic amino acid residues;
amino acid residue w' is absent or is a hydrophobic amino acid residue;
at least one of residues u and v and at least one of residues x and y are hydrophilic amino acid residues and the other of amino acid residues u and v and x and y are any amino acid residue; and
amino acid residue z is any amino acid residue.

The polypeptide has at least 45 amino acid residues in its sequence, especially in the range of 50 to 300 amino acid residues, for example, in the range of 60 to 250 amino acid residues, 70 to 200 amino acid residues, 80 to 150 amino acid residues or 90 to 120 amino acid residues. In some embodiments, the polypeptides have 90 to 110 amino acid residues.

In some embodiments, the polypeptide has a folded tertiary structure that is a well defined bundle of α-helix subunits lacking elements of beta secondary structure when in bulk solution. In some embodiments, the folded tertiary structure is a 2-5 helix bundle, especially a 4 helix bundle.

In some embodiments, the polypeptides comprise at least two peptides having α-helical propensity, especially 2 to 5 peptides, more especially 2 to 4 peptides and most especially 4 peptides having α-helical propensity. Each peptide having α-helical propensity within the polypeptide may be the same or different.

In particular embodiments, the polypeptide has a sequence (t u v w w' x y z)$_m$ that is the same as the peptide sequence (a b c d d' e f g)$_n$. In other embodiments, the peptide sequence (t u v w w' x y z)$_m$ differs from the peptide sequence (a b c d d' e f g)$_n$ in up to 10 amino acid residues, especially less than 8 residues, less than 7 residues, less than 6 residues, less than 5 residues, less than 4 residues, less than 3 residues or less than 2 residues. When the amino acid sequence (t u v w w' x y z)$_m$ differs from the sequence (a b c d d' e f g)$_n$, the differing residues are residues that do not affect the amphiphilic nature of the polypeptide and are preferably conservative substitutions. For example, a conservative substitution may be one hydrophobic amino acid residue for another hydrophobic amino acid residue, one small amino acid residue for another small amino acid residue, one negatively charged amino acid residue for another negatively charged amino acid residue, one positively charged amino acid residue for another positively charged amino acid residue, or a polar amino acid residue for another polar amino acid residue.

In some embodiments, the polypeptide has a sequence (t u v w w' x y z)$_m$ that is different from the peptide sequence (a b c d d' e f g)$_n$. In these embodiments, the polypeptide sequence may have one or more charged amino acid residues to facilitate interaction with the peptide or peptides at the liquid-liquid interface by electrostatic interaction or by coordination.

Without wishing to be bound by theory, it is believed that the peptide $X_1$-(a b c d d' e f g)$_n$-$X_2$ stabilizes the emulsion by adsorbing at the liquid-liquid interface. The polypeptide conjugated to the pharmacokinetic modifying agent or targeting agent is able to associate with the peptide-stabilized emulsion droplet surface decorating the surface with pharmacokinetic modifying agents or targeting agents without the necessity of attaching such agents to the emulsion interface by chemical reaction or covalent bond. This process occurs spontaneously when the polypeptide conjugated to the pharmacokinetic modifying agent or targeting agent is added to the pre-formed peptide stabilized nanoemulsion due to energetic considerations.

The peptides having α-helical propensity in the polypeptide surfactant are linked by a sequence of 3 to 11 amino acid residues that enable folding of the peptides in bulk solution so that the peptides may interact with one another to form a folded tertiary structure such as a 2, 3, 4 or 5 α-helix bundle. In some embodiments, the peptides having α-helical propensity are linked by 3 to 9, 3 to 7, 3 to 5 amino acid residues. In a particular embodiment, the peptides having α-helical propensity are linked by 3 amino acid residues.

In some embodiments, the sequence of amino acid residues linking the peptides having α-helical propensity includes an amino acid residue that is an α-helix breaking amino acid residue. This residue assists in terminating any α-helical structure formed by the preceding peptide having α-helical propensity and allowing the linking amino acid residues flexibility for folding. α-Helix breaking amino acid residues include amino acid residues that are unable to contribute to α-helical structure, such as proline, have high flexibility, for example serine. The charged group on aspartic acid is also known to have low helix propensity. Common α-helix breaking amino acid residues include proline and glycine.

The sequence of amino acid residues linking the peptides having α-helical propensity also may include one or more residues that allow flexibility so that two adjacent peptides can fold so that they interact with one another. In particular embodiments, the sequence of amino acid residues linking the peptides having α-helical propensity allows the peptides to fold in a manner to form a 2, 3, 4 or 5 helix bundle, especially a 4-helix bundle, in bulk solution. In some embodiments, the flexibility is imparted by one or more amino acid residues having a small side chain, for example, glycine, serine, alanine, valine, cysteine and threonine. In some embodiments, these same amino acids play a dual role of conferring flexibility to the overall sequence of linking amino acid residues as well as helix termination.

When more than one linking sequence is present in the polypeptide, for example, where there are three to five α-helical peptides, each linking sequence may be the same or different.

In some embodiments, the linking sequence comprises D-P-X where X is a small amino acid residue such as serine, glycine, cysteine or threonine. In some embodiments, the linking sequence comprises D-P-S. In some embodiments, the linking sequence is D-P-S.

Amino acid residues t and w are hydrophobic amino acid residues. In some embodiments, amino acid residues t and w are independently selected from L-alanine, L-valine, L-leucine, L-methionine, L-isoleucine, L-phenylalanine, L-tyrosine, D-alanine, D-valine, D-leucine, D-methionine, D-isoleucine, D-phenylalanine, D-tyrosine, especially L-alanine, L-methionine, L-valine and L-leucine.

Amino acid residue w' may be absent or may be a hydrophobic amino acid residue. The residue w' may be included in longer helix sequences, for example, where m is 3, 6, 9 or 12, to counteract perturbations in the helix turn that may result in misalignment of the hydrophobic residues on one face of the helix. In some embodiments, w' is present in the third, sixth, ninth and/or twelfth sequence of (t u v w w' x y z)$_m$ when m is 3, 6, 9 and 12, but is absent in the other (t u v w w' x y z) sequences in an α-helical peptide. In some embodiments, when present, amino acid w' may be selected from L-alanine, L-valine, L-leucine, L-methionine, L-isoleucine, L-phenylalanine, L-tyrosine, D-alanine, D-valine, D-leucine, D-methionine, D-isoleucine, D-phenylalanine, D-tyrosine, especially L-alanine, L-methionine, L-valine and L-leucine.

At least one of u and v is a hydrophilic amino acid residue, such as L-serine, L-threonine, L-cysteine, L-tyrosine, L-asparagine, L-glutamine, L-aspartic acid, L-glutamic acid, L-lysine, L-histidine, L-ornithine, D-serine, D-threonine, D-cysteine, D-tyrosine, D-asparagine, D-glutamine, D-aspartic acid, D-glutamic acid, D-lysine, D-histidine and D-ornithine, especially L-serine, L-threonine, L-cysteine, L-tyrosine, L-asparagine, L-glutamine, L-aspartic acid, L-glutamic acid, L-lysine, L-histidine and L-ornithine. The other one of amino acid residues u and v is any amino acid residue, especially an amino acid residue that has a propensity to form α-helices, such as alanine, lysine, uncharged glutamic acid, methionine, leucine and aminoisobutyric acid or a small amino acid residue such as alanine, serine, valine, leucine or isoleucine, or a hydrophilic amino acid residue such as glutamine, asparagine, serine, glutamic acid and aspartic acid, provided that u and v are not both charged amino acid residues that have the same charge.

At least one of x and y is a hydrophilic amino acid residue, such as L-serine, L-threonine, L-cysteine, L-tyrosine, L-asparagine, L-glutamine, L-aspartic acid, L-glutamic acid, L-lysine, L-histidine, L-ornithine, D-serine, D-threonine, D-cysteine, D-tyrosine, D-asparagine, D-glutamine, D-aspartic acid, D-glutamic acid, D-lysine, D-histidine and D-ornithine, especially L-serine, L-threonine, L-cysteine, L-tyrosine, L-asparagine, L-glutamine, L-aspartic acid, L-glutamic acid, L-lysine, L-histidine and L-ornithine. The other one of amino acid residues x and y is any amino acid residue, especially an amino acid residue that has a propensity to form α-helices, such as alanine, lysine, uncharged glutamic acid, methionine, leucine and aminoisobutyric acid or a small amino acid residue such as alanine, serine, valine, leucine or isoleucine, or a hydrophilic, amino acid residue such as glutamine, asparagine, serine, glutamic acid and aspartic acid, provided that x and y are not both charged amino acid residues that have the same charge.

Amino acid residue z may be any amino acid residue. In particular embodiments, amino acid residue z is a residue that has a propensity to form α-helices, such as alanine, lysine, uncharged glutamic acid, methionine, leucine and aminoisobutyric acid, especially alanine, lysine and uncharged glutamic acid; or amino acid residues that are not detrimental to α-helix formation, for example, amino acid residues other than proline and glycine.

In some embodiments, each amino acid residue u is independently selected from a small hydrophobic amino acid residue, such as alanine, leucine, valine and isoleucine, or a hydrophilic amino acid residue, especially a polar or positively charged amino acid residue such as L-serine, L-threonine, L-cysteine, L-tyrosine, L-asparagine, L-glutamine, L-lysine, L-arginine or L-histidine. In some embodiments, each u is independently selected from L-lysine, L-histidine, L-serine, L-alanine, L-asparagine and L-glutamine.

In some embodiments, each amino acid residue v is independently selected from a polar, positively charged or negatively charged amino acid residue, such as L-serine, L-threonine, L-cysteine, L-tyrosine, L-asparagine, L-glutamine, L-lysine, L-arginine, L-histidine, L-aspartic acid or L-glutamic acid. In some embodiments, each v is independently selected from L-glutamine, L-arginine, L-serine, L-glutamic acid and L-asparagine.

Each amino acid residue x is independently any amino acid residue and may be hydrophobic or hydrophilic. In some embodiments, each x is independently selected from L-alanine, L-valine, L-leucine, L-isoleucine, L-serine, L-threonine, L-aspartic acid and L-glutamic acid, especially L-alanine, L-serine and L-glutamic acid.

In some embodiments, each amino acid residue y is a polar, positively charged or negatively charged amino acid residue, such as L-serine, L-threonine, L-cysteine, L-tyrosine, L-asparagine, L-glutamine, L-lysine, L-arginine, L-histidine, L-aspartic acid or L-glutamic acid. In some embodiments, each y is independently selected from L-aspartic acid, L-glutamic acid, L-arginine, L-glutamine, L-histidine, L-lysine and L-asparagine.

Amino acid residue z is independently any amino acid residue and may be hydrophobic or hydrophilic. In some embodiments, the residue z is independently selected from a small hydrophobic residue or a polar uncharged residue. In some embodiments, each z is independently selected from L-alanine, L-valine, L-leucine, L-isoleucine, L-serine, L-threonine, L-asparagine and L-glutamine, especially L-alanine, L-serine and L-glutamine.

In particular embodiments, at least one peptide of the polypeptide comprises an amino acid residue with an amino group or carboxylic acid group in its side chain. In some embodiments, each peptide of the polypeptide comprises an amino acid residue with an amino or carboxylic acid in its side chain. In some embodiments, at least one peptide in the polypeptide comprises a lysine residue. In some embodiments, each peptide in the polypeptide comprises a lysine residue. In other embodiments, at least one peptide in the polypeptide comprises a glutamic acid or aspartic acid residue. In some embodiments, each peptide propensity in the polypeptide comprises a glutamic acid or aspartic acid residue.

In some embodiments, the polypeptide has one of the following sequences:

```
SEQ ID NO: 32:
MD(PS-MKQLADS-LHQLARQ-VSRLEHA-D)4(DAMP4)

SEQ ID NO: 33:
MD(PS-MKQLADS-LHQLARQ-VSRLEHA-D)2

SEQ ID NO: 34:
MD(PS-AKSLAES-LHSLARS-VSRLEHA-D)4

SEQ ID NO: 35:
MD(PS-AKSVAES-LHSLARS-VSRLVEHA-D)4

SEQ ID NO: 36:
MD(PS-AHSVAES-LHSLARS-VSRLVEHA-D)4

SEQ ID NO: 37:
MD(PS-AHSVAKS-LHSLARS-VSRLVSHA-D)4

SEQ ID NO: 38:
MD(PS-AHSVAES-LHSLAES-VSELVSHA-D)4

SEQ ID NO: 39:
MD(PS-AQSVAQS-LAQLAQS-VSQLVSQA-D)4

SEQ ID NO: 40:
MD(PS-ANSVANS-LANLANS-VSNLVSNA-D)4

SEQ ID NO: 41:
MD(PS-AQSVAES-LAQLAES-VSELVSQA-D)4

SEQ ID NO: 42:
MD(PS-ANSVAES-LANLAES-VSELVSNA-D)4.

SEQ ID NO: 43:
MD(PS-MKQLADS-LMQLARQ-VSRLESA-D)4.

SEQ ID NO: 44:
MD(PS-LMQLARQ-MKQLADS-LMQLARQ-VSRLESA-D)4.

SEQ ID NO: 45:
MD(PS-MKELADS-LMQLARQ-VDRLESA-D)4.

SEQ ID NO: 46:
MD(PS-MKQLADS-LHQLAHQ-VSHLEHA-D)4.

SEQ ID NO: 47:
MD(PS-MEELADS-LEELARQ-VEELESA-D)4.

SEQ ID NO: 48:
MD(PS-MKKLADS-LKKLARQ-VKKLESA-D)4.

SEQ ID NO: 49:
MD(PS-MKQLADS-LHQLAHK-VSHLEHA-D)4.

SEQ ID NO: 50:
MD(PS-EISALEK-EISALEK-EISALEK-D)4.
```

-continued
SEQ ID NO: 51:
MD(PS-KISALKE-KISALKE-KISALKE-D)$_4$.

SEQ ID NO: 52:
MD(PS-MKELADS-LHELARE-VSRLEHA-D)$_4$.

SEQ ID NO: 53:
MD(PS-MKELADS-LHQLARQ-VSRLEHA-D)$_4$.

SEQ ID NO: 54:
MD(PS-MKQLADS-LHELARQ-VSRLEHA-D)$_4$.

SEQ ID NO: 55:
MD(PS-MKELADS-LHELARQ-VSRLEHA-D)$_4$.

SEQ ID NO: 56:
MD(PS-MKELADS-LHQLARE-VSRLEHA-D)$_4$.

SEQ ID NO: 57:
MD(PS-MKQLADS-LHELARE-VSRLEHA-D)$_4$.

SEQ ID NO: 58:
MD(PS-AESVAES-LAELAES-VSELVSEA-D)$_4$.

SEQ ID NO: 59:
MD(PS-ADSVADS-LADLADS-VSPLVSDA-D)$_4$.

SEQ ID NO: 60:
MD(PS-AESVAES-LAELAES-VSELVSEA-D)$_4$.

SEQ ID NO: 61:
MD(PS-ADSVAES-LADLAES-VSELVSDA-D)$_4$.

In some embodiments, the polypeptide surfactant is conjugated to at least one pharmacokinetic modifying agent. In some embodiments, the pharmacokinetic modifying agent is a polyalkylene glycol, a polyalkyloxazoline such as polyethyloxazoline (PEOX), or polyvinylpyrolidone, especially a polyalkylene glycol such as polyethylene glycol or polypropylene glycol, more especially polyethylene glycol (PEG). The polyethylene glycol may have a molecular weight between 2500 and 25000 Da, especially 2500 and 20000 Da. In a particular embodiment, the PEG has a molecular weight of about 5000 Da.

In some embodiments, the polypeptide surfactant includes 1 to 15 pharmacokinetic modifying agents, especially 1 to 13, 1 to 9 or 1 to 5, more especially 1 to 5 pharmacokinetic modifying agents.

The pharmacokinetic modifying agent may be conjugated to the polypeptide through a side chain reactive group and/or through the C-terminal carboxyl group or the N-terminal amino group. For example, the pharmacokinetic modifying agent may be conjugated to an amino group in the side chain of a lysine residue or ornithine residue or to a carboxyl group of an aspartic acid residue or a glutamic acid residue and/or be conjugated to the C- or N-terminus. In some embodiments, at least one pharmacokinetic modifying agent is attached to the N- or C-terminus and at least one side chain amino or carboxyl group, especially the N- or C-terminus and more than one side chain amino or carboxyl group. In some embodiments, the pharmacokinetic modifying agent is conjugated to the N- or C-terminus and one amino acid side chain in each α-helical peptide of the polypeptide surfactant. In some embodiments, the pharmacokinetic modifying agent is conjugated to the polypeptide at the N-terminus and a side chain amino group in each α-helical peptide of the polypeptide, especially a side chain amino group of a lysine residue.

In other embodiments, the polypeptide surfactant is conjugated to at least one targeting agent. The targeting agent may be any molecule that binds to a cell surface receptor in the target tissue or organ to which the nanoemulsion is to be delivered. For example, the targeting agent may be a small molecule such as folate or an oestrogen, peptides such as tumor-targeting peptide or may be an antibody or antibody fragment such as an scFv or diabody, directed to a particular cell surface receptor.

Suitable targeting peptides include Lyp-1 (CGNKRTRGC; SEQ ID NO:62), Bombesin peptide (QQRLGNQWAVGHLM; SEQ ID NO:63) and suitable tumor-targeting peptides include RGD peptides such as RGD, cyclic RGD dimer and CRGDKRGPDEC (iRGD; SEQ ID NO:64).

Suitable antibodies or fragments thereof include anti-PSMA and anti-HER2, target receptors for IL-6, IFN8, VEGF, EGF, CA-125, Clec9A, Clec12A, TNF-α, CD4, CD8, CD19, CD64, CD3, CD28, CD40, CD326 and CD20 (rituximab), or monoclonal antibodies targeting cancer-associated proteoglycans such as melanoma-associated proteoglycans, or cancer-associated gangliosides, for example, GD2 and GD3).

In some embodiments, there is one targeting agent, such as an antibody or fragment thereof, conjugated to each polypeptide surfactant. In other embodiments, different antibodies or fragments thereof are conjugated to polypeptide surfactants, where the polypeptide surfactants may be the same or different. In these embodiments, multiple types of antibodies, for example, two different antibodies or fragments thereof are presented on the surface of the nanoemulsion. Multiple antibodies or fragments thereof may be selected to target a particular cell, tissue or tumour.

Optionally the pharmacokinetic modifying agent or targeting agent is conjugated to the polypeptide surfactant through a linker. The linker may be any divalent molecule able to covalently bind to both the polypeptide surfactant and the pharmacokinetic modifying agent or targeting agent. Suitable linkers include divalent alkylene, alkenylene or alkynylene groups, which may be linear or branched or where one or more —$CH_2$— groups in the alkylene, alkenylene or alkynylene group may be replaced by —O—, —S—, —NH—, —N(alkyl)-, —C(O)NH—, —NH—C(O)—, 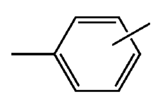 or

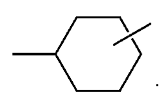

.

Alternatively, the linker may be an amino acid residue or peptide. For example, the linker may be a peptide that confers flexibility on the linker and is made up of amino acid residues having small side chains. Exemplary peptide linkers include polyalanine, -GlyGlyGlyGlySer- (SEQ ID NO:65) and -GlySerGlySer- (SEQ ID NO:66).

The polypeptide surfactant may be prepared by methods known in the art, such as solid phase synthesis or solution phase synthesis using Fmoc or Boc protected amino acid residues. Alternatively, the polypeptide surfactant may be prepared by recombinant techniques as known in the art using standard microbial culture technology, genetically engineered microbes and recombinant DNA technology (Sambrook and Russell, Molecular Cloning: A Laboratory Manual ($3^{rd}$ Edition), 2001, CSHL Press).

In brief, the genetically engineered microbes contain a polynucleotide sequence that comprises a nucleotide sequence that encodes the polypeptide. The nucleotide sequence is operably linked to a promoter sequence. The microbes may be any microbes suitable for use in culturing processes such as fermentation. Examples of suitable microbes include *E. coli, Saccharomyces cerevisiae, Bacillis subtilis* and *Piccia pastoris*, especially *E. coli*. Any culturing process may be used, for example, fermentation. During the culturing process the microbes express the polypeptide.

Once culturing is complete, the microbial cells may be further treated in the culture medium, for example, the fermentation broth, or may be isolated and stored or resuspended in the same or different media. Cells may be isolated by commonly used techniques such as centrifugation or filtration. Optionally cells may undergo a cell-conditioning step after cell recovery. For example, the cells may be collected and resuspended in water or buffered solution prior to storage or use.

After culturing, the microbial cells are disrupted to provide a disruptate composition comprising soluble proteins and cell debris. Cell disruption may be achieved by means known in the art including mechanical means and non-mechanical means. Small scale disruption may be achieved by methods such as sonication or homogenization. Large scale disruption may be achieved by mechanical means such as bead milling, homogenization and microfluidization, or non-mechanical means including physical means such as decompression, osmotic shock and thermolysis; chemical means such as antibiotics, chelating agents, chaotropes, detergents, solvents, hydroxide and hyperchlorite; and enzymatic means such as lytic enzymes, autolysis and cloned phage lysis.

Optionally after the cell disruption step, solid cell debris is removed by techniques known in the art such as centrifugation or filtration. Removal of cell debris provides a solution of soluble cell proteins that includes the polypeptide surfactant.

Purification of the polypeptide from other contaminating cell proteins and polypeptides may be achieved by treating the cell disruptate, either directly from cell disruption or clarified by removal insoluble cell debris, with a kosmotropic salt in an amount suitable to salt-out cell derived contaminants but salt-in the protein or polypeptide molecule of the invention.

The kosmotropic salt may be formed from a kosmotropic ion. Examples of kosmotropic ions include sulphate, carbonate, phosphate, lithium, fluoride, calcium and acetate. The counterion of the salt may be any suitable counterion of opposite charge.

The amount of kosmotropic salt is an amount suitable to precipitate contaminating proteins and polypeptides but not the polypeptide of interest. This amount can readily be determined by those skilled in the art by exposing a sample of cell disruptate, with or without clarification, to a range of salt concentrations, separating the precipitate, and supernatant and analyzing the supernatant to determine the amount of contaminating proteins in the supernatant and pellet by SDS-PAGE or HPLC. In some embodiments, the amount of kosmotropic salt is in the range of 0.2 M and 2.0 M. In some embodiments, the amount of kosmotropic salt is in the range of 0.2 M and 0.5 M, for example, about 0.25 M. In other embodiments, the amount of kosmotropic salt is in the range of 0.5 M and 2.9 M, for example, 1.0 M and 2.0 M, especially about 1.5 M.

After treatment with the kosmotropic salt, the precipitate containing cell contaminants and the supernatant containing the polypeptide may be separated by methods known in the art such as gravity sedimentation, centrifugation or filtration.

Alternatively, established chromatography methods may be used to separate the cell contaminants and polypeptide surfactant.

The polypeptide may be readily conjugated with at least one pharmacokinetic modifying agent by methods known in the art, for example, amide formation. In one embodiment, a suitably derivatized or activated PEG molecule may be reacted with the N-terminal amine and/or amino group(s) in the side chain(s) of amino acid(s) in the polypeptide. A suitably derivatized or activated PEG molecule is N-hydroxysuccinamide-PEG. Alternatively, the derivatized or activated PEG may be reacted with the C-terminal carboxy group and/or carboxy group(s) in the side chain(s) of the polypeptide. A suitable derivatized PEG is $H_2N$-PEG. The carboxy groups of the polypeptide may be activated by means known in the art for forming amide bonds.

The targeting agent may also be conjugated to the polypeptide by formation of an amide bond with the N- or C-terminus or an amino group or carboxy group of a side chain in the polypeptide. When the targeting agent is a peptide or an antibody or fragment thereof, the targeting agent may be conjugated or be included by preparation of a fusion protein whereby the fusion protein is produced recombinantly by methods known in the art where the polynucleotide sequence encodes both antibody and polypeptide. For example, the fusion protein may be prepared recombinantly and purified using protein purification techniques known in the art, such as Protein A chromatography and/or ion exchange chromatography. Alternatively a fusion protein containing the antibody or fragment thereof may be purified by precipitation with molecular crowding techniques, such as PEG precipitation.

In some embodiments, the nanoemulsion comprises one type of peptide surfactant and one type of polypeptide surfactant. In other embodiments, the nanoemulsion comprises more than one type of peptide surfactant and one type of polypeptide surfactant. In yet other embodiments, the nanoemulsion comprises one type of peptide surfactant and more than one type of polypeptide surfactant. In further embodiments, the nanoemulsion comprises more than one type of peptide surfactant and more than one type of polypeptide surfactant.

In some embodiments where there is more than one peptide surfactant, the peptide surfactants may be selected to have attractive properties between them. Without wishing to be bound by theory, it is thought that when the peptide surfactants are able to interact at the liquid-liquid interface, more peptides may be adsorbed at the liquid-liquid interface.

In some embodiments, the nanoemulsion comprises at least one peptide surfactant and a polypeptide surfactant conjugated to at least one pharmacokinetic modifying agent, such as PEG. This combination confers stability to isotonic salt conditions, such as biological conditions.

In some embodiments, the nanoemulsion comprises at least one peptide surfactant and a polypeptide surfactant conjugated to at least one targeting agent, such as an antibody or fragment thereof. This combination confers targeting properties on the nanoemulsion.

In some embodiments, the nanoemulsion comprises at least one peptide surfactant and more than one polypeptide surfactant, wherein one polypeptide surfactant is conjugated to at least one pharmacokinetic modifying agent and another polypeptide surfactant is conjugated to at least one targeting agent. This combination confers stability to isotonic salt conditions and targeting properties on the nanoemulsion.

In some embodiments where the nanoemulsion comprises at least one peptide surfactant and at least one polypeptide surfactant, a targeting agent may be provided to the surface of the nanoemulsion using an entity other than a polypeptide surfactant. For example, the entity may be a peptide or protein that has affinity for a charged surface presented by the peptide surfactants at the liquid-liquid interface. In these embodiments, especially where the peptide surfactant at the liquid-liquid interface is rich in lysine or arginine residues, the entity conjugated to the antibody or fragment thereof may be rich in negative charges, thereby able to electrostatically interact with the surface of the nanoemulsion droplet. Alternatively the entity conjugated to the antibody or fragment thereof may be rich in positive charges, which is then able to coordinate to the surface of the nanoemulsion droplet via electrostatic attraction to carboxyl functionalities within the peptide surfactant located at the liquid-liquid interface. Alternatively coordination chemistry may be used, for example, via coordination to transition metal ions, eg: $Zn^{++}$, $Ni^{++}$ or $Cn^{++}$ using histidine groups (eg: His6) agent and those in the sequence of the peptide or polypeptide surfactant adsorbed at the liquid-liquid interface.

In some embodiments the targeting agent may be added to the terminus of the polypeptide comprising the pharmacokinetic modifying agent before or after it is located at the liquid-liquid interface, for example, SEQ ID NO: 32—conjugated to PEG, using techniques known in the art such as biotin-streptavidin linkage or "click chemistry" approaches.

In some embodiments, the nanoemulsion comprises a peptide surfactant and at least one polypeptide surfactant where the polypeptide surfactant is conjugated to a pharmacokinetic modifying agent or a targeting agent and the nanoemulsion comprise another entity conjugated to a targeting agent, wherein the two targeting agents are different.

In some embodiments, the nanoemulsion comprises at least one peptide surfactant and more than one type of polypeptide surfactant, wherein one polypeptide surfactant is conjugated to a pharmacokinetic modifying agent and another polypeptide surfactant is conjugated to an antibody or fragment thereof or other entity bound to another antibody or fragment thereof, wherein the two antibodies or fragments thereof are different.

The nanoemulsion has an average droplet size in the range of between 25 and 1000 nm, especially 50 and 500 nm, more especially 50 to 250 nm.

The nanoemulsions include an oil phase and a polar or aqueous phase that is immiscible with the oil phase. Suitable polar or aqueous phases include water, buffer, methanol, ethanol, propenol and mixtures thereof. Suitable oil phases include neutral esters of saturated coconut and palm kernel oil-derived caprylic and capric fatty acids and glycerine or propylene glycol such as Miglyol® 810, 812, 818, 829 and 840, edible oils such as olive oil, sunflower oil, safflower oil, grapeseed oil, sesame oil, coconut oil, canola oil, corn oil, flaxseed oil, palm oil, palm kernel oil, peanut oil and soyabean oil, or triglycerides rich in unsaturated fatty acids or mixtures thereof.

In some embodiments, the nanoemulsion droplets further comprise a coating comprising a polypeptide conjugated to a pharmacokinetic modifying agent as previously described, such as PEG. Without wishing to be bound by theory, the coating provides a backfilling of the surface of the nanoemulsion where there is no pharmacokinetic modifying agent or antibody on the surface of the nanoemulsion providing a surface coating that assists in preventing non-specific binding of the nanoemulsion to cells in tissues and organs.

In some embodiments, the nanoemulsion further comprises a pharmaceutically active agent. In some embodiments, the pharmaceutically active agent is sparingly soluble, slightly soluble, very slightly soluble or practically insoluble in water but is very soluble, freely soluble or soluble in the oil phase. In these embodiments, the pharmaceutically active agent may be delivered in therapeutic doses overcoming solubility issues. Suitable sparingly soluble, slightly soluble, very slightly soluble and insoluble pharmaceutically active agents include cancer drugs such as taxol, paclitaxel, docetaxel, carbazitaxel, camptothecin, 10-hydroxycamptothecin, irinotecan, doxorubicin, etoposide, temolzolomide, teniposide, amsacrine, actinomycin D, ellipticine and bis-dioxopiperazines such as ICRF-1893; corticosteroids such as methylprednisilone, prednisilone, prednisone, betametasone and budesonid; and steroid hormones such as testosterone, progesterone and levonorgestrel.

In some embodiments, the pharmaceutically active agent is soluble in aqueous solution, for example, the pharmaceutically active agent is a protein antigen or siRNA. In some embodiments, the protein antigens may elicit an immunogenic response against an invading pathogen, for example, in infectious disease. In other embodiments, the protein antigen may elicit a tolerogenic response in an autoimmune disease or in organ replacement or repair. Suitable protein antigens include tumour-associated cell lysates, CD1, CD3, CD4, CD5, CD8, CD15, CD27, CD30, CD31, CD44, C47, LRRC16 and prostate specific antigen (PSA) or other protein antigens associated with autoimmunity or infectious disease. Tumour cell lysates are derived from a patient's tumour and contain antigens specific to the tumour from which they are derived optionally together with cytokines, allowing for the use of nanoemulsion directed to personal medicine approaches.

In some embodiments, where a tolerogenic response is required, the nanoemulsion further comprises at least one inhibitor of NF-κB in an amount sufficient to inhibit the NF-κB pathway of the antigen presenting cells to which the antigen is being delivered. Suitable NF-κB inhibitors include antioxidants, proteosome and protease inhibitors of REL/NF-κB, phosphorylation and/or degradation inhibitors and other NF-κB inhibitors. Suitable antioxidants include α-lipoic acid, α-tocopherol, aged garlic extract (allicin), 2-Amino-1-methyl-6-phenylimidazo[4,5-b]pyridine (PhIP), allopurinol, 5,6,3',5'-tetramethoxy-7,4'-hydroxyflavone, bis-eugenol, butylated hydroxyanisole (BHA), 3,4-dihydroxycinnamic acid, curcumin, diethyldithiocarbamate, ethyl pyruvate, folic acid, glutathione, hydroquinone, melatonin, N-acetyl-cysteine, quercetin, spironolactone and vitamin C. Suitable proteosome and protease inhibitors of REL/NF-kB include N-acetyl-leucinyl-leucinyl-norleucinyl (ALLnL), N-acetyl-leucinyl-leucinyl-methionyl (LLM), carbobenzoxyl-leucinyl-leucinyl-norvalinyl (Z-LLnV), carbobenzoxyl-leucinyl-leucinyl-leucinyl (Z-LLL), bortezomib, cyclosporine A, tacrolimus, disulfiram, N-acetyl-DL-phenylalanine-β-naphthyl ester, N-benzoyl L-tyrosine-ethyl ester, 3,4-dichloroisocoumarin, diisopropyl fluorophosphate, N-α-tosyl-L-phenylalanine chloromethyl ketone and N-α-tosyl-L-lysine chloromethyl ketone. Suitable phosphorylation or degradation inhibitors include desloratiadine, salmeterol, fluticasone propionate, LY29, LY30, evodiamine, geldanamycin, 4-(2'-aminoethyl)amino-1,8-dimethylimidazo(1,2-a)-quinoxaline, cobrotoxin, nitric oxide, thienopyridine, 2-amino-6-[2-(cyclopropylmethoxy)-6-hydroxyphenyl]-4-piperidin-4-yl nicotinonitrile, N-(4-hydroxyphenyl)retinamide, scytonemin, zerumbone, silibinin, sulfasalazine, quercetin, rosmarinic acid, staurosporine, gamma-tocotrienol, thalidomide, anethole, benzylisothiocyanate, digitoxin, interferon-α, methotrexate, capsaicin, genistein and ursodeoxycholic acid. Other NF-kB inhibitors include α-pinene, indole-3-carbinol, 1,2,3,4,6-penta-O-galloyl-β-D-glucose, selenomethionine, neomycin, rapamycin, ethylpyruvate, 2-acetylaminofluorene, 7-amino-4-methylcoumarin, camptothecin, cinnamaldehyde, clarithromycin, erythromycin, glycyrrhizin, linoleic acid, 2-methoxyestradiol, prostaglandin E2, rapomycin, raloxifene, ribavirin, ritonavir, rosiglitazone and xylitol.

In some embodiments, the pharmaceutically active agent is soluble, freely soluble or very soluble in water and is included in the nanoemulsion oil phase on a nanoparticle such as a dendrimer, or in an aqueous nanodroplet within the oil phase, or by oil-phase solubilisation using a surfactant or polymer to alter the surface properties of the pharmaceutically active agent from hydrophilic to hydrophobic.

The nanoemulsions of the invention may be useful in solubilizing sparingly soluble, slightly soluble, very slightly soluble or insoluble pharmaceutically active agents and may be useful in providing targeted delivery of any pharmaceutically active agent, soluble or insoluble, to a particular organ, tissue or site in the body.

The nanoemulsions of the invention may be prepared by methods known in the art for preparing nanoemulsions, for example, high energy mixing, homogenization or sonication.

The nanoemulsion may be prepared in a stepwise manner whereby an initial nanoemulsion is formed comprising oil and aqueous phase in which the aqueous phase comprises the at least one peptide surfactant. The polypeptide surfactant is included in the initial nanoemulsion by adding the polypeptide surfactant to the initial nanoemulsion and subjecting the mixture to high energy mixing. In some embodiments, the polypeptide surfactant is conjugated to a pharmacokinetic modifying agent or a targeting agent.

In some embodiments, in which the nanoemulsion includes two polypeptide surfactants, one comprising a pharmacokinetic modifying agent and the other comprising a targeting agent, the initial nanoemulsion comprising the peptide surfactant is vigorously mixed with a polypeptide surfactant comprising one of a pharmacokinetic modifying agent and a targeting agent to form an intermediate nanoemulsion followed by a further subsequent step of vigourously mixing the intermediate nanoemulsion with another polypeptide surfactant comprising the other of a pharmacokinetic modifying agent or targeting agent.

The backfilling coating may be added by mixing the nanoemulsion comprising the at least one peptide surfactant and the at least one polypeptide surfactant conjugated to a pharmacokinetic modifying agent or targeting agent with further polypeptide surfactant comprising a pharmacokinetic modifying agent such as PEG and vigorously mixing the nanoemulsion and further polypeptide.

If a pharmaceutically active agent is to be incorporated into the nanoemulsion, it is included in the oil phase when preparing the initial nanoemulsion comprising the first peptide surfactant. In some embodiments, the pharmaceutically active agent is soluble in the oil phase. In other embodiments the pharmaceutically active agent is insoluble in the oil phase. When the pharmaceutically active agent is insoluble in the oil phase, solubilisation may be achieved by use of a suitable surfactant. In other embodiments, the pharmaceutically active agent may be included as a solid particulate dispersed in the oil phase, for example as a solid-in-oil nanodispersion in which a hydrophilic molecule, such as a protein antigen, is coated with a hydrophobic surfactant and lyophilised to produce a hydrophobic particulate solid (Tahara, et al., J. Contr. Release, 2008, 131: 14-18).

The ratios of peptide surfactant and polypeptide conjugated to a pharmacokinetic modifying agent and/or targeting agent will vary depending on the formulation of the nanoemulsion and will depend on the amount of oil used in the nanoemulsion, the drug being used, the targeting agent and the level of cell receptor being targeted.

In some embodiments, the oil phase is present in the initial emulsion in an amount between 0.5 to 10% v/v, especially 0.5 to 5% v/v, more especially 1 to 3% v/v, most especially around 2% v/v. For administration the formed emulsion may be concentrated prior to pharmaceutical use by methods known in the art including gravitational or centrifugal separation.

In some embodiments, the ratio of peptide surfactant to polypeptide surfactant conjugated to a pharmacokinetic modifying agent is 1:1 to 30:1 on a w/w basis, especially about 10:1 to 25:1, more especially 20:1.

The ratio of peptide surfactant to polypeptide surfactant conjugated to a targeting agent which is an antibody may vary depending on the antibody used and the density of cell receptor being targeted.

In embodiments where the nanoemulsion includes a coating or is backfilled with polypeptide conjugated with a pharmacokinetic modifying agent such as PEG, the amount of polypeptide conjugated to pharmacokinetic modifying agent is sufficient to coat the surface of the nanoemulsion droplet where there is no presentation of targeting agent.

The loading of pharmaceutically active agent in the oil phase may be any pharmaceutically active agent loading that is suitable to deliver a therapeutic level of pharmaceutical and will depend on the drug being administered and the patient being treated.

In yet another aspect of the invention there is provided a method of preparing a nanoemulsion of the invention comprising the steps of:

1. providing an oil phase and an aqueous phase, said aqueous phase comprising a peptide comprising the amino acid sequence:

$X_1\text{-}(abcdd'efg)n\text{-}X_2$ wherein n is an integer from 2 to 12;
    amino acid residues a and d are hydrophobic amino acid residues;
    amino acid residue d' is absent or is a hydrophobic amino acid residue;
    at least one of residues b and c and at least one of residues e and f are hydrophilic amino acid residues and the other of amino acid residues b and c and e and f are any amino acid residue;
    amino acid residue g is any amino acid residue;
    $X_1$ is absent, an N-terminal capping group, or an amino acid residue or a peptide of 2 to 10 amino acid residues optionally capped with an N-terminal capping group; and
    $X_2$ is absent, a C-terminal capping group, or an amino acid residue or a peptide of 2 to 10 amino acid residues optionally capped with a C-terminal capping group;

2. mixing the oil phase and aqueous phase to provide a nanoemulsion;

3. adding to the nanoemulsion formed in step 2, a polypeptide surfactant comprising at least two peptides having α-helical propensity linked by a linking sequence of 3 to 11 amino acid residues, wherein each peptide having α-helical propensity comprises the amino acid sequence:

$(tuvww'xyz)_m$ wherein m is an integer from 2 to 12;
    amino acid residues t and w are hydrophobic amino acid residues;

amino acid residue w' is absent or is a hydrophobic amino acid residue;

at least one of residues u and v and at least one of residues x and y are hydrophilic amino acid residues and the other of amino acid residues u and v and x and y are any amino acid residue; and amino acid residue z is any amino acid residue;

4. mixing the mixture of step 3 to provide a nanoemulsion.

In some embodiments, the polypeptide surfactant is conjugated to a pharmacokinetic modifying agent or a targeting agent. In some embodiments the pharmacokinetic modifying agent is PEG, especially PEG with a molecular weight of between 2000 and 25000 Da, more especially about 5000 Da. In some embodiments, the polypeptide surfactant is conjugated to between 1 and 5 pharmacokinetic modifying agents. In some embodiments, the oil phase comprises a drug.

In some embodiments, where step 3. utilizes a polypeptide surfactant conjugated to a pharmacokinetic modifying agent, the method optionally further comprises the step of:

i) adding a polypeptide surfactant according to the invention conjugated to a targeting agent, to the stabilized nanoemulsion formed from step 4 and mixing the nanoemulsion to form a stabilized, targeted nanoemulsion.

In some embodiments, where step 3 utilizes a polypeptide surfactant conjugated to a targeting agent, the method optionally comprises the step of:

ii) adding a polypeptide surfactant according to the invention conjugated to a pharmacokinetic agent, to the stabilized nanoemulsion formed in step 4 and mixing the nanoemulsion to provide a stabilized, targeted nanoemulsion.

In some embodiments, the method further comprises the step of:

iii) adding to the nanoemulsion formed in any one of steps 4, i) or ii) a polypeptide surfactant conjugated to a pharmacokinetic modifying agent and mixing the mixture to provide a coated nanoemulsion.

In a particular embodiment, the method of the invention comprises the steps of:

a) providing an oil phase and an aqueous phase, said aqueous phase comprising a peptide comprising the amino acid sequence:

$X_1$-$(abcdd'efg)_n$-$X_2$ wherein n is an integer from 2 to 12;

amino acid residues a and d are hydrophobic amino acid residues;

amino acid residue d' is absent or is a hydrophobic amino acid residue;

at least one of residues b and c and at least one of residues e and f are hydrophilic amino acid residues and the other of amino acid residues b and c and e and f are any amino acid residue;

amino acid residue g is any amino acid residue;

$X_1$ is absent, an N-terminal capping group, or an amino acid residue or a peptide of 2 to 10 amino acid residues optionally capped with an N-terminal capping group; and $X_2$ is absent, a C-terminal capping group, or an amino acid residue or a peptide of 2 to 10 amino acid residues optionally capped with a C-terminal capping group;

b) mixing the composition of step a) to provide a nanoemulsion;

c) adding to the nanoemulsion of step b), a polypeptide surfactant comprising at least two peptides having α-helical propensity linked by a linking sequence of 3 to 11 amino acid residues, wherein each peptide having α-helical propensity comprises the amino acid sequence:

$(tuvww'xyz)_m$ wherein m is an integer from 2 to 12;

amino acid residues t and w are hydrophobic amino acid residues;

amino acid residue w' is absent or is a hydrophobic amino acid residue;

at least one of residues u and v and at least one of residues x and y are hydrophilic amino acid residues and the other of amino acid residues u and v and x and y are any amino acid residue; and amino acid residue z is any amino acid residue, wherein the polypeptide surfactant is conjugated to a pharmacokinetic modifying agent or a targeting moiety;

d) mixing the mixture of step c) to form a stabilized or targeted nanoemulsion.

In this embodiment of the method, when the polypeptide surfactant of step c) comprises a pharmacokinetic modifying agent, the method may further comprise the step of:

e) adding a polypeptide surfactant of the invention conjugated to a targeting agent to the stabilized nanoemulsion of step d) and mixing the mixture to form a stabilized, targeted nanoemulsion.

The embodiment of the invention may also comprise the further step of:

f) adding a polypeptide surfactant of the invention conjugated to a pharmacokinetic modifying agent to the stabilized or targeted nanoemulsion of step d) or the stabilized, targeted nanoemulsion of step e) and mixing the nanoemulsion to provide a coated (backfilled) stabilized and/or targeted nanoemulsion.

The mixing used in this aspect of the invention may be high energy mixing, such as homogenization or sonication.

In another aspect of the invention there is provided a polypeptide surfactant comprising at least two peptides having α-helical propensity linked by a linking sequence of 3 to 11 amino acid residues, wherein each peptide having α-helical propensity comprises the amino acid sequence:

$(tuvww'xyz)_m$ wherein m is an integer from 2 to 12;

amino acid residues t and w are hydrophobic amino acid residues;

amino acid residue w' is absent or is a hydrophobic amino acid residue;

at least one of residues u and v and at least one of residues x and y are hydrophilic amino acid residues and the other of amino acid residues u and v and x and y are any amino acid residue; and amino acid residue z is any amino acid residue; wherein the polypeptide surfactant is conjugated to at least one pharmacokinetic modifying agent or a targeting agent.

In some embodiments, the polypeptide surfactant is conjugated to at least one pharmacokinetic modifying agent, especially PEG. In some embodiments, the PEG has a molecular weight of 2000 Da to 25000 Da, especially about 5000 Da. In some embodiments, the polypeptide surfactant is conjugated to 1 to 5 pharmacokinetic modifying agents.

In some embodiments, the polypeptide surfactant is conjugated to a targeting agent, especially an antibody or fragment thereof or small molecule receptor ligand such as folate or oestrogen, more especially an antibody or fragment thereof.

Optionally, the pharmacokinetic modifying agent or antibody is conjugated to the polypeptide surfactant through a linker. The linker may be any divalent molecule able to covalently bind to both the polypeptide surfactant and the pharmacokinetic modifying agent or targeting agent. Suitable linkers include divalent alkylene, alkenylene or alkynylene groups, which may be linear or branched or where one or more —CH$_2$— groups in the alkylene, alkenylene or alkynylene group may be replaced by —O—, —S—, —NH—, —N(alkyl)-, —C(O)NH—, —NH—C(O)—,

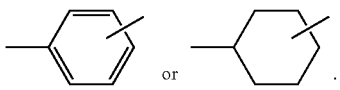

Alternatively, the linker may be an amino acid residue or peptide. For example, the linker may be a peptide that confers flexibility on the linker and is made up of amino acid residues having small side chains. Exemplary peptide linkers include a polyalanine, -GlyGlyGlyGlySer- (SEQ ID NO:65) and -GlySerGlySer- (SEQ ID NO:66).

Although the invention is useful for delivering a cargo such as a pharmaceutically active agent, the nanoemulsions of the present invention also have the advantage that the particles are very stable and therefore retain their size and shape without coalescence even in complex mixtures. Therefore, the nanoemulsions of the invention, especially those that have a pharmacokinetic modifying agent on the surface, can be used as an internal standard in analytical techniques that analyse particle size or to calibrate instruments that measure particle size.

In another aspect of the invention there is provided a use of a nanoemulsion as an analytical standard, said nanoemulsion comprising an oil phase dispersed in an aqueous phase, at least one peptide surfactant and at least one polypeptide surfactant; wherein:

i) the at least one peptide surfactant comprising the amino acid sequence:

$X_1$-(abcdd'efg)$_n$-$X_2$ wherein n is an integer from 2 to 12;
amino acid residues a and d are hydrophobic amino acid residues;
amino acid residue d' is absent or is a hydrophobic amino acid residue;
at least one of residues b and c and at least one of residues e and f are hydrophilic amino acid residues and the other of amino acid residues b and c and e and f are any amino acid residue;
amino acid residue g is any amino acid residue;
$X_1$ is absent, an N-terminal capping group, an amino acid residue or a peptide of 2 to 10 amino acid residues optionally capped with an N-terminal capping group; and
$X_2$ is absent, a C-terminal capping group, an amino acid residue or a peptide of 2 to 10 amino acid residues optionally capped with a C-terminal capping group; and
ii) the at least one polypeptide surfactant comprising at least two peptides having α-helical propensity linked by a linking sequence of 3 to 11 amino acid residues, wherein each peptide having α-helical propensity comprises the amino acid sequence:

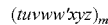

wherein m is an integer from 2 to 12;
amino acid residues t and w are hydrophobic amino acid residues;
amino acid residue w' is absent or is a hydrophobic amino acid residue;
at least one of residues u and v and at least one of residues x and y are hydrophilic amino acid residues and the other of amino acid residues u and v and x and y are any amino acid residue; and
amino acid residue z is any amino acid residue.

In some embodiments, the at least one polypeptide surfactant is conjugated to at least one pharmacokinetic modifying agent. In some embodiments, the pharmacokinetic modifying agent is polyethylene glycol (PEG), especially where the PEG has a molecular weight of between 2000 and 25000 Da, more especially about 5000 Da. In some embodiments, the at least one polypeptide surfactant is conjugated to between 1 and 5 pharmacokinetic modifying agents.

In order that the invention may be readily understood and put into practical effect, particular embodiments will now be described by way of the following non-limiting examples.

EXAMPLES

Example 1

Preparation of the Peptide of SEQ ID NO:32 (DAMP4)

1. DAMP4 Expression

Protein surfactant SEQ ID NO:32 (also referred to as DAMP4) sequence was cloned into pET48b vector and expressed in *E. coli* with high expression and solubility. Briefly, DAMP4 was expressed as a soluble protein in *E. coli* BL21 (DE3). Glycerol stock of the transformed cells was streaked onto an LB plate (15 g L$^{-1}$ agar, 10 g L$^{-1}$ peptone, 5 g L$^{-1}$ yeast extract, 10 g L$^{-1}$ NaCl) containing kanamycin sulphate (50 mg L$^{-1}$). A single colony from the plate was inoculated into 10 mL LB media (10 g L$^{-1}$ peptone, 5 g L$^{-1}$ yeast extract, 10 g L$^{-1}$ NaCl) and incubated for 16 h at 37° C. as a seed culture. 400 μL of seed culture was inoculated into 400 mL LB media containing 50 mg L$^{-1}$ of kanamycin and incubated at 37° C. in an orbital shaker (BioLine, Alexandria, Australia) at 180 rpm.

When the OD$_{600}$ reached 0.5, cultures were induced with 0.1 mM isopropyl β-D-1-thiogalactopyranoside (IPTG) (AMRESCO®, Solon, US) and incubated for another 5 h at 37° C. The cell pellet was collected by centrifugation for 15 min at 2000 g at 4° C. (Beckman. Coulter-Avanti® J-20 XPI) and stored at −80° C. until further use.

2. DAMP4 Purification

The purification of DAMP4 involved sequential chromatographic methods, specifically immobilized metal affinity chromatography (IMAC), ion exchange (IEX) and then reversed-phase HPLC (RP-HPLC) polishing. In brief, cell pellets were resuspended in lysis buffer (50 mM NaCl, 25 mM NaH$_2$PO$_4$, 2 mM MgCl$_2$, 0.5% v/v Triton X-100 pH 7.5) and disrupted by ultrasonication (4 cycles of 45 seconds each; Branson Ultrasonics Corporation, Connecticut, USA). Homogenate was centrifuged at 8000 g (Avanti® J-26 XPI, Beckman Coulter) at 4° C. for 30 min and the supernatant was filtered through a 0.45 μm filter. Clarified cell lysate was loaded to a Ni$^{2+}$ charged 5 mL HisTrap FF IMAC column using an ÄKTA Explorer™ 10 chromatography system (GE Healthcare Biosciences) pre-equilibrated with five column volumes (CV) of Buffer A (50 mM NaCl, 25 mM $NaH_2PO_4$, pH 7.5). Unbound sample was washed out by 4 CV of Buffer A. Pre-elution was performed for 3.8 CV at 6% Buffer B (50 mM NaCl, 25 mM $NaH_2PO_4$, 500 mM imidazole, pH 7.5) and DAMP4 was eluted from the column with 80% Buffer B for 8 CV. Elution fractions were pooled and further purified on a HiTrap QFF 1 mL column coupled with a HiTrap SP FF 1 mL column. Only flow-through fractions were collected from this step. DAMP4 collected from IEX was further purified on semi-preparative RP-HPLC to confirm that the function was similar to RP-HPLC-purified chemically synthesized biosurfactant. A Jupiter C5 10 μm 300 Å 250 mm×10 mm column (Phenomenex) with 0.1% (v/v) TFA (A) and 90% acetonitrile, 0.1% 9 v/v TFA (B) as the solvent system was used. DAMP4-containing fractions were lyophilized and store at −80° C. until the PEGylation. Quantification of DAMP4 was performed on RP-HPLC using a standard curve.

Example 2

Preparation and Characterization of Nano-Scale Emulsions

Miglyol 812 was a gift from Sasol (Rosebank, Johannesburg, South Africa). Peptide of SEQ ID NO:1 (also referred to as AM1) (MW 2473.9, >95% purity by RP-HPLC) and peptide of SEQ ID NO:2 (also referred to as DAMP1) (MW2731, >95% purity by HPLC) were custom synthesized by GenScript Corporation (Piscataway, N.J., USA). Polypeptide of SEQ ID NO:32 (DAMP4) (MW 11116.5 Da) was recombinantly produced and purified as described in Example 1. Lyophilized aliquots were stored at −80° C. for use as needed. Peptide concentration was determined by quantitative amino acid analysis (Australian Proteome Analysis Facility, Sydney, Australia) on lyophilized samples.

To prepare nanoemulsions, lyophilized. SEQ ID NO:1 or SEQ ID NO:2 (400 μM) was dissolved in 980 μL 25 mM HEPES, 800 μM $ZnCl_2$ pH 7.0. Miglyol® 812 (20 μL was added to give an oil volume fraction of 2% (v/v). Lyophilized SEQ ID NO:32 was dissolved in a buffer containing 25 mM HEPES (pH 7.0) and 200 μM $ZnCl_2$ to a final concentration of 100 μM. Miglyol® 812 (20 μL) was added to give an oil volume fraction of 2% (v/v). The mixture was homogenized using a Branson Sonifier 450 ultrasonicator for four 30-second bursts at 60 W. The resulting nanoemulsion was diluted 100-fold into water prior to analysis. Particle size measurements were performed using a Malvern Zetasizer Nano ZS (Malvern, Worcestershire, UK) equipped with a He—Ne laser (633 nm).

As shown in FIG. 1, at the same peptide to Zn (II) ratio, SEQ ID NO:1 nanoemulsion droplets had the smallest size (167.0±1.1 nm), while the ones prepared from SEQ ID NO:2 and SEQ ID NO:32 had z-averaged diameters of 202.1±2.5 and 246.0±1.1 nm respectively.

Example 3

Conjugation of Polyethylene Glycol to SEQ ID NO:32

Figure 2:
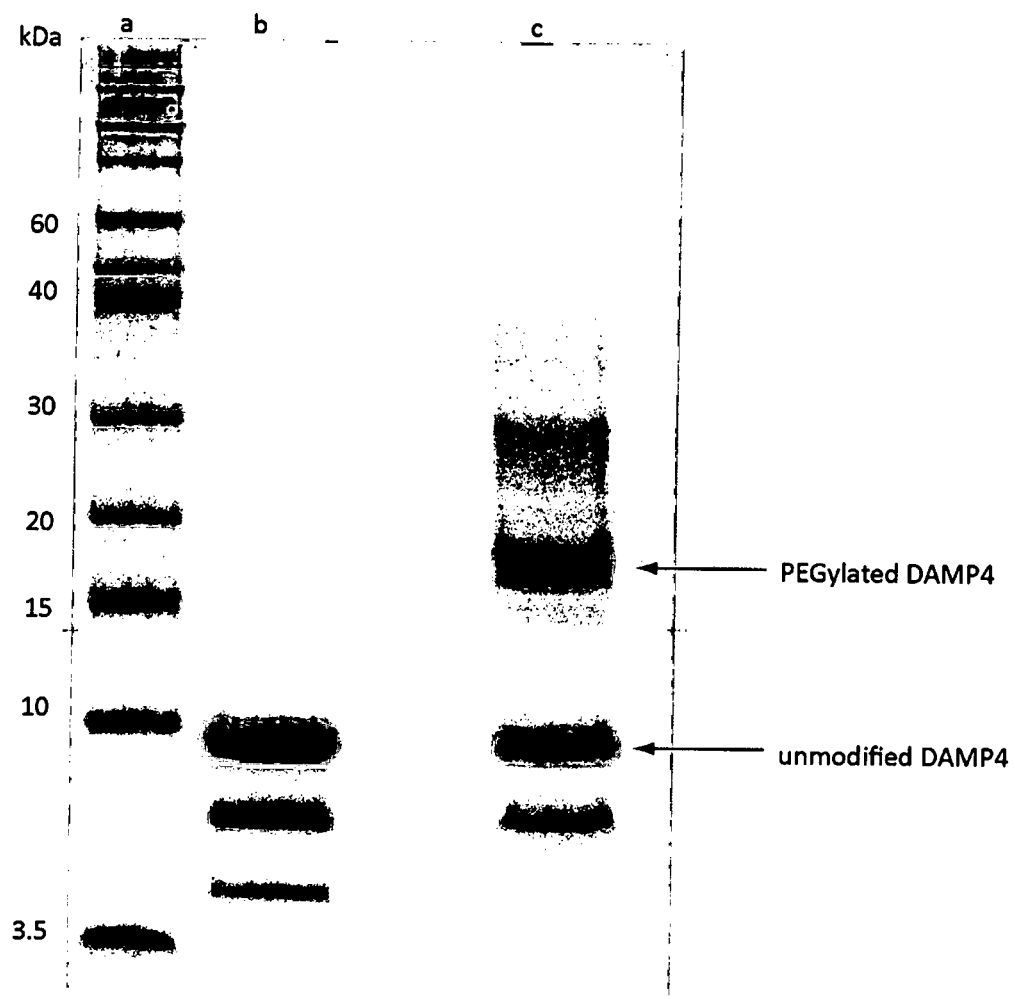
FIG. 2 is a photographic representation of an SDS-PAGE gel showing samples from a PEGylation reaction of SEQ ID NO:32 (DAMP4). Lane a: Novex® Sharp Pre-stained Protein Standard (Novex®, Mulgrave, Australia); Lane b: Lyophilized SEQ ID NO:32 (DAMP4) re-dissolved in 25 mM HEPES; Lane c: SEQ ID NO:32 (DAMP4) PEGylation reaction mixture.

Methyoxyl N-hydroxylsuccinamide (NHS) functionalized polyethylene glycol (mPEG-NHS) (average MW 5000, PDI<1.08, purity>95%) was purchased from Nanocs (New York, USA). Lyophilized SEQ ID NO:32 was dissolved in 25 mM HEPES, pH 7.0 and a known amount of mPEG-NHS (molar ratio of mPEG:SEQ ID NO:32=20:1) was added to the solution, and the conjugation reaction was performed for 12 hours at 4° C. The reaction product, which contained PEGylated SEQ ID NO:32 (PEG-DAMP4), unmodified SEQ ID NO:32 and free PEG, was analysed by SDS-PAGE using 10% SDS-PAGE tricine gel. In FIG. 2, the additional band at size ~17.5 kDa, indicates that PEGylation of SEQ ID NO:32 with 5 kDa PEG was successful.

Example 4

Decorating a Nanoemulsion with PEG and Testing of Serum Stability

The nanoemulsion (TNE) must be isotonic to biological cells for therapeutic application. Hence the stability of a nanoemulsion comprising a minimum amount of PEG-DAMP4 (10 μM) (S-TNE) for stabilization in physiological salt conditions (PBS) was examined. To produce the PEGylated nanoemulsion, 500 μL of SEQ ID NO:1 nanoemulsion from Example 2 was added to 500 μL of 20 μM PEGylated DAMP4 solution prepared according to Example 3 (using either 5 kDa or 20 kDa PEG) followed by 60 seconds of vigorous stirring using a magnetic stirrer.

Concentration of PEGylated DAMP4 was determined based on the amount of SEQ ID NO:32 that had been added into the PEGylation mixture, which was calculated based on an established RP-HPLC standard curve. As controls, SEQ ID NO:1 nanoemulsion was also mixed with 60 mg $mL^{-1}$ of 5 kDa non-conjugated PEG or 20 μM SEQ ID NO:32. The stability of the resulting PEGylated nanoemulsion was determined by measuring their Z-average size after 100-fold dilution in the isotonic PBS.

The results are shown in Table 4. Only nanoemulsion mixed with PEGylated DAMP4 remained stable in PBS, indicating that the PEGylated SEQ ID NO:32 created sufficient steric repulsion around the oil droplets, preventing flocculation and coalescence in the presence of a high concentration of salt.

TABLE 4

| Formulation | Average droplet size in water (nm) | Average droplet size in PBS (nm) |
|---|---|---|
| SEQ ID NO: 1 nanoemulsion | 166.7 ± 3.9 | flocculated |
| SEQ ID NO: 1 nanoemulsion with 5 kDa PEG | 181.3 ± 2.1 | flocculated |
| SEQ ID NO: 1 nanoemulsion with DAMP4 | 171.6 ± 1.0 | flocculated |
| SEQ ID NO: 1 nanoemulsion with 5 kDa PEGylated DAMP4 | 174.3 ± 2.4 | 176.1 ± 2.5 |
| SEQ ID NO: 1 nanoemulsion with 20 kDa PEGylated DAMP4 | 197.6 ± 3.4 | 197.0 ± 2.7 |

Figure 3:
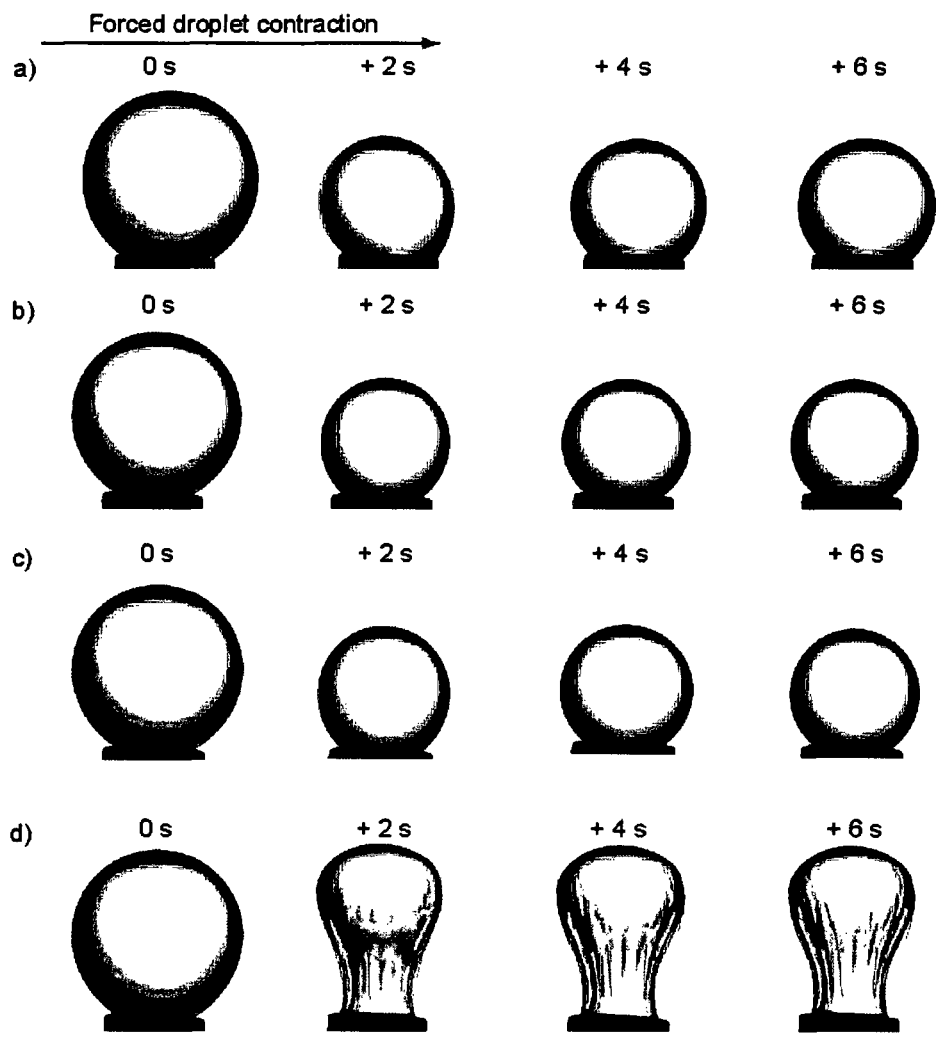
FIG. 3 is a photographic representation of a 10 minute old Miglyol® 812 droplet formed from an inverted needle in AM1-$Zn^{++}$ solution, aged for 10 minutes followed by the addition of one of (a) HEPES buffer, (b) SEQ ID NO:32 (DAMP4), (c) PEG or (d) PEGylated SEQ ID NO:32 (PEG-DAMP4). Droplets were subjected to a sudden contraction in droplet volume. Only the droplet aged in the presence of PEG-DAMP4 showed crumpling on the droplet surface, while the others aged with either PEG or DAMP4 alone, rapidly relaxed back to a spherical shape.
Figure 4:
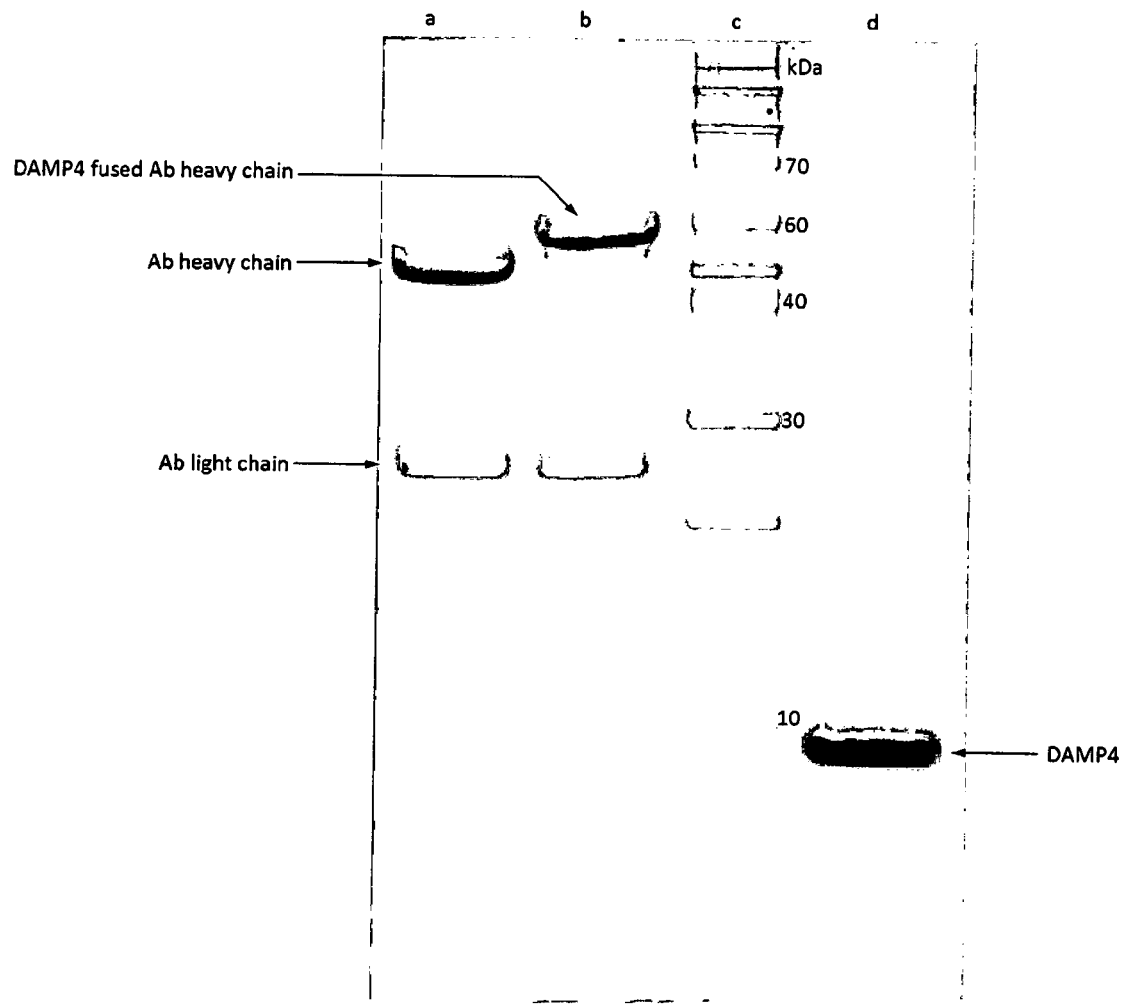
FIG. 4 is a photographic representation of an SDS-PAGE gel showing: Lane a: anti-Clec9A antibody; Lane b: SEQ ID NO:32 fused with anti-Clec9A antibody; Lane c: Novex® Sharp pre-stained Protein Standard (Novex®, Mulgrave, Australia); Lane d: SEQ ID NO:32 (DAMP4).

A droplet contraction experiment provided further evidence of droplet surface PEGylation via the added PEG-DAMP4 solution. A Miglyol® 812 droplet was formed by injection of oil through an inverted needle into a SEQ ID NO:1—Zn solution and allowed to age for 10 minutes. An addition of 10 μM SEQ ID NO:32, 2.4 μM non-conjugated PEG or 10 μM PEG-DAMP4 was made and the droplet was aged for a further 10 minutes. After a sudden contraction in the droplet volume, only the bubble aged with PEG-DAMP4 showed an elastic skin and wrinkle effects. Meanwhile bubbles aged with either SEQ ID NO:32 or PEG rapidly relaxed back to a spherical shape (FIG. 3).

Example 5

Binding of PEGylated Nanoemulsion to CHO-K1 Cell Lines

The cell binding profile of the PEGylated nanoemulsion was determined using confocal laser scanning microscopy (CLSM). The PEGylated nanoemulsion was prepared as described in Example 4. In order to visualize nanoemulsion under confocal microscopy, emulsion droplets were internally labeled with 1,1'-dioctadecyl-3,3,3'3'-tetramethyl-indocarbocyanine perchlorate (DiI). DiI is a low toxic, lipophilic red fluorescent dye which is preferentially integrated into Miglyol® 812 without causing any background signals from free dye in the aqueous phase. Briefly, DiI (Molecular Probes®, Eugene, US) was dissolved in ethanol to a concentration of 10 mg $mL^{-1}$. The resulting DiI solution was added to Miglyol® 812 at 8-fold dilution followed by vigorous mixing. The DiI loaded Miglyol® 812 was used for preparing the PEGylated nanoemulsion following the same process detailed in Example 4.

Chinese hamster ovary (CHO)-K1 and mouse Clec9A transfected. CHO-K1-5B6 cell lines were provided by Walter and Eliza Hall Institute (WEHI, NSW Australia). Both cell lines were grown in RPMI 1640 medium (Gibco®, Mulgrave, Aus) supplemented with 10% heat inactivated fetal calf serum (FCS) at 37° C. in a 5% $CO_2$ humidified atmosphere. Cell medium for growing CHO-K1-5B6 was supplemented with 500 μg $mL^{-1}$ of G418 (A.G. Scientific, San Diego, US) for selection pressure.

For cell binding experiments, CHO-K1 and CHO-K1-5B6 cells were seeded onto 12 $mm^2$ coverslips in 24-well tissue culture plates at a density of $2\times10^5$ cells per well and incubated at 37° C. in a 5% $CO_2$ humidified atmosphere overnight prior to further treatment. The PEGylated nanoemulsion was added to cells at 20-fold dilution and incubated for 1 h at 4° C. to prevent internalization of bound nanoemulsion. Unbound emulsion was removed by washing with cold PBS three times. Cells were fixed with 4% (w/v) paraformaldehyde for 15 min at 4° C. Fixed cells were washed 3 times with PBS before counter-staining with Alexa 647-conjugated phalloidin (Molecular Probes®, Mulgrave, Aus) for cell membrane and DAPI (Molecular Probes®, Mulgrave, Aus) for nucleus. Coverslips were mounted onto glass slides using DAKO fluorescence mounting medium (DAKO, California, US). Images were acquired on Zeiss Confocal LSM510 META (Carl-Ziess, Sydney, Australia) and processed using Zen software.

PEG is a commonly employed surface coating polymer for decreasing interaction with biological interfaces (Cortez, Tomaskovic-Crook et al. 2006). Ideally, a PEGylated nanoemulsion should have minimum association to non-target cells. However, intensive DiI fluorescence co-localized with the phalloidin was observed in both cell lines suggesting that while the deposited PEG on SEQ ID NO:1 emulsion droplet surface provided stability towards salt solutions, it was not sufficient to create a barrier and such PEGylated nanoemulsions non-selectively bound to both cell lines.

Example 6

Construction of a Coated (Backfilled) PEGylated Nanoemulsion (BS-TNE)

Figure 5:
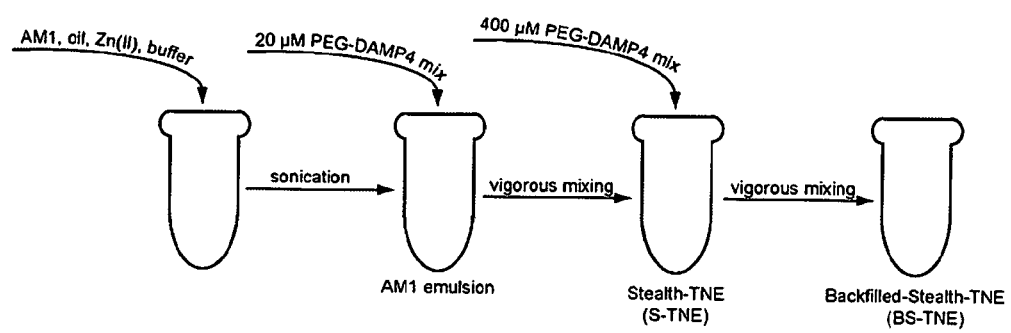
FIG. 5 is a pictorial representation of the preparation of a nanoemulsion stabilized with PEGylated SEQ ID NO:32 (PEG-DAMP4) and coated with PEG-DAMP4 to give a backfilled-stabilized (stealth) tailorable nanoemulsion (BS-TNE).

To reduce non-specific binding of the PEGylated nanoemulsion, an increased amount of PEGylated DAMP4 was used to coat or ‘backfill’ the available surface area of SEQ ID NO:1 emulsion not covered by the low concentration of PEG-DAMP4 mix used initially. As demonstrated in FIG. 5, a PEG-DAMP4 backfilled S-TNE (BS-TNE) was constructed by mixing same volume of S-TNE and 400 μM of PEG-DAMP4.

Example 7

Cell Binding of BS-TNE

The cell binding profile of the BS-TNE was tested in the CHO-K1 cell lines as described in Example 5.

The CLSM results showed a significant decrease of signal in the DiI channel of the CLSM image from the BS-TNE indicating that the non-specific binding of the nanoemulsion was significantly downshifted. This experiment confirms that SEQ ID NO:1-based nanoemulsions coated with sufficient PEGylated DAMP-4 showed very low non-specific cell binding propensity.

Example 8

Figure 6:
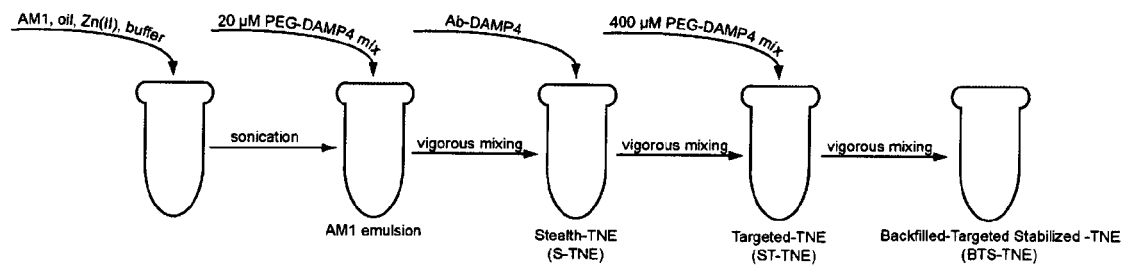
FIG. 6 is a pictorial representation of the preparation of a nanoemulsion stabilized with PEGylated SEQ ID NO:32 (PEG-DAMP4), targeted with SEQ ID NO:32 conjugated to an antibody (Ab-DAMP4) and coated with PEG-DAMP4 to give a backfilled-targeted-stabilized-(stealth)-tailorable nanoemulsion (BTS-TNE).
Figure 7:
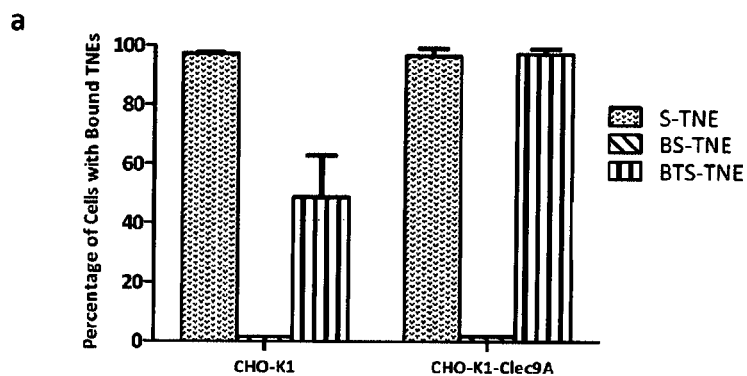
FIG. 7 is a graphical representation of mean 1,1'-dioctadecyl-3,3,3',3'-tetramethyl-indocarbocyanine perchlorate (DiI) fluorescence intensity calculated from flow cytometry analysis of the binding of nanoemulsions to a mixed cell population of (a) 1:1 and (b) 10:1 mixed CHO-K1 and CHO-Clec9A modified cells.
Figure 7:
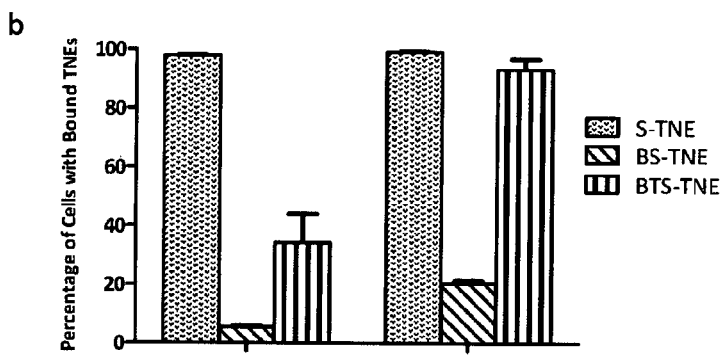
Figure 8:
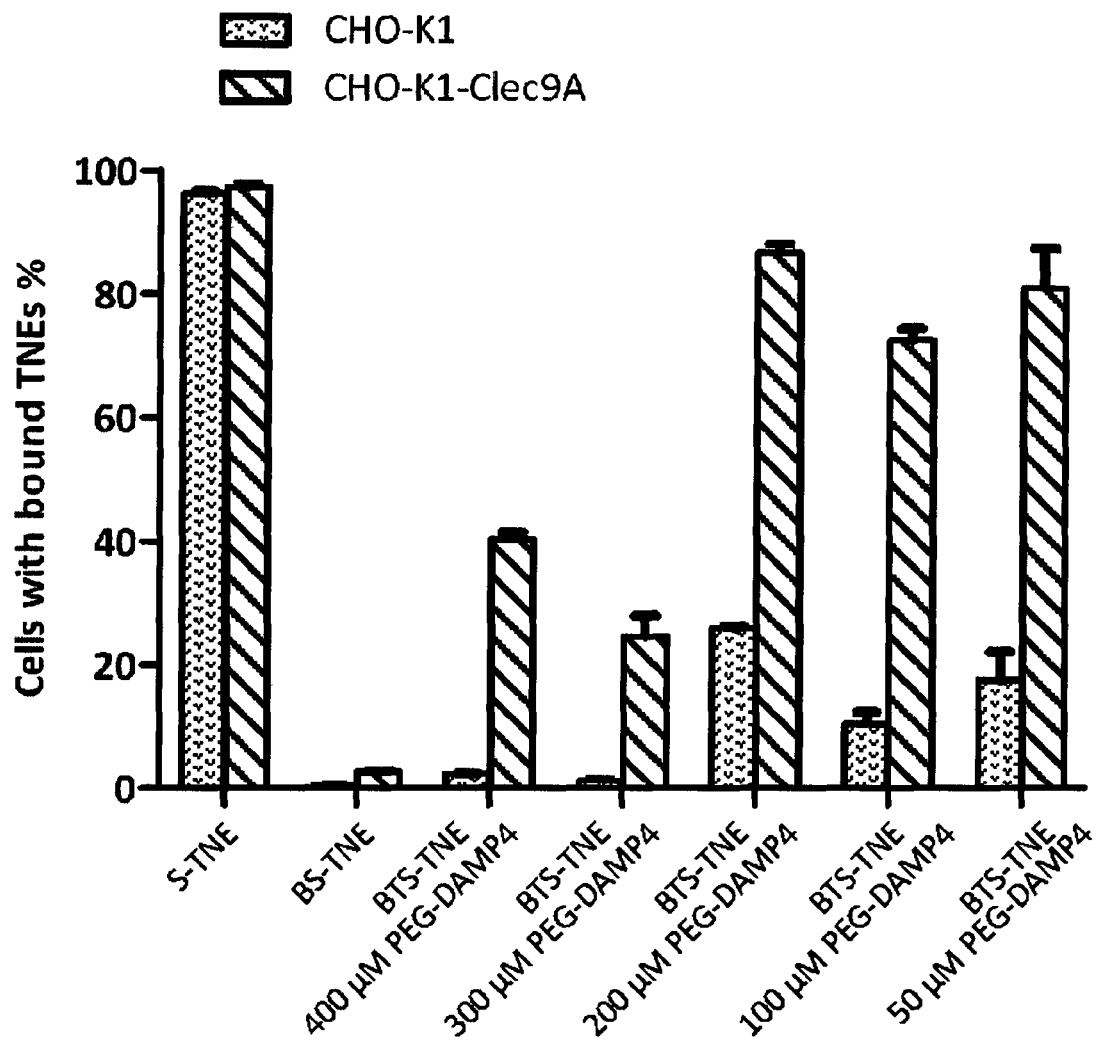
FIG. 8 is a graphical representation of the percentage of cells bound with nanoemulsion calculated from flow cytograms showing the effects of varying PEG content in the nanoemulsion system containing 20 antibodies per droplet.
Figure 9:
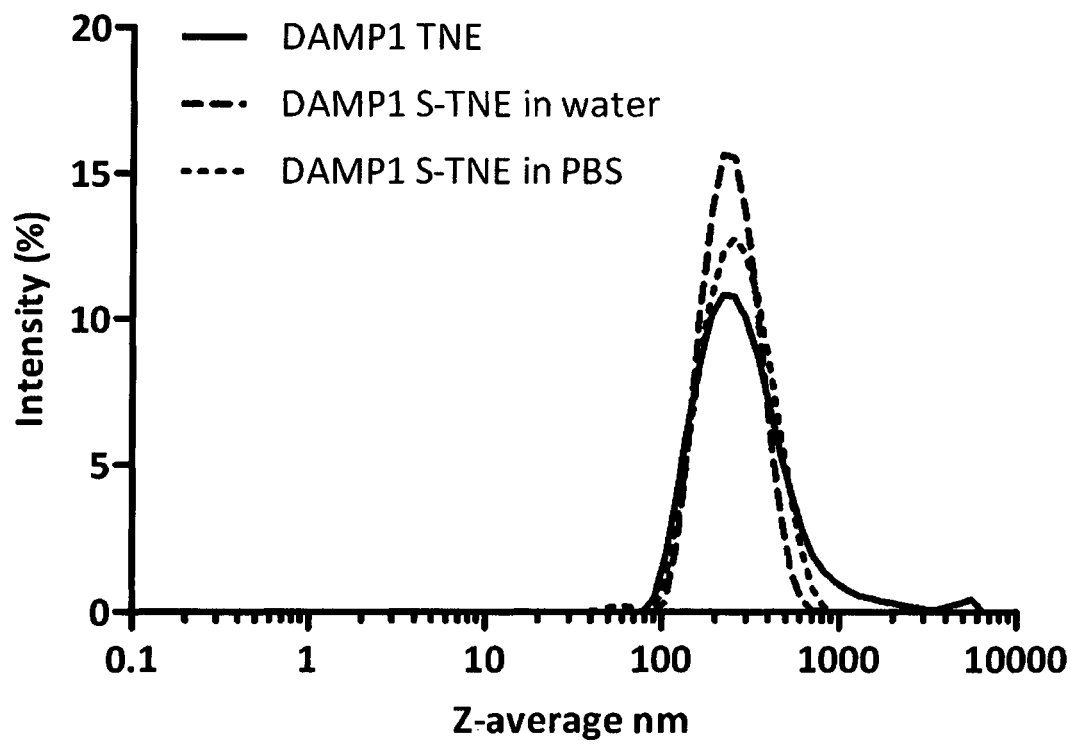
FIG. 9 is a graphical representation showing droplet size distributions of tailorable nanoemulsions (TNEs) prepared from SEQ ID NO:2 (DAMP1). DAMP1 alone in water (____) DAMP1 and PEGylated DAMP4 in water (— — - ); DAMP1 and PEGylated-DAMP4 in PBS ( - - - ).

Fusion of Antibody and SEQ ID NO:32 (Ab-DAMP4)

Rat anti-mouse Clec9A antibody fused with SEQ ID NO:32 (Clec9A-DAMP4) was generated using recombinant DNA techniques. SEQ ID NO:32 sequence was cloned into an expression vector, in-frame with the end of the heavy chain of rat-anti-Clec9A mAb, and expressed using standard cell-culture techniques known in the art. The fusion Ab was analyzed on 10% tricine SDS-PAGE gel, compared with the rat anti-mouse Clec9A Ab and unmodified SEQ ID NO:32 (shown in FIG. 4) confirming the expected size shift.

Example 9

Preparation of a Backfilled Targeted Stabilized Nanoemulsion

Having demonstrated the successful decoration of a SEQ ID NO:1 nanoemulsion with PEG via conjugation to SEQ ID NO:32, resulting in a nanoemulsion stable in isotonic salt, a backfilled-targeted-stabilized nanoemulsion (BTS-TNE), which integrated both targeting (T) and stabilizing (S) characteristics, with control of cell-non-specific binding by additional backfilling (B) using PEG-DAMP4, was undertaken.

To prepare BTS-TNE, antibody labelled SEQ ID NO:32 (Ab-DAMP4) prepared via Example 8 was first integrated into a PEGylated nanoemulsion prepared according to Example 4, via physical adsorption. Specifically, 36 μL of 0.5 mg $mL^{-1}$ Ab-DAMP4 (Example 8) was added to 1 mL of PEGylated nanoemulsion (Example 4) followed by 60 s of vigorous mixing. Based on the molecular mass of the Ab-DAMP4 (~170 kDa), the resulting TS-TNE was coated with approximately 100 Ab molecules per oil droplet, assuming complete adsorption. Then 200 μL of the resulting TS-TNE mixture was added to the same volume of 400 μM PEG-DAMP4 solution, prepared according to Example 3, to introduce additional PEGylated DAMP4 to the TS-TNE droplet surface as shown in FIG. 6. This "backfilling" step, whereby exposed SEQ ID NO:1 surface without any PEG or Ab coating is blocked by further PEG-conjugated SEQ ID NO:32, gives the final BTS-TNE.

Example 10

Targeted Delivery of BTS-TNE to Cells

Figure 10:
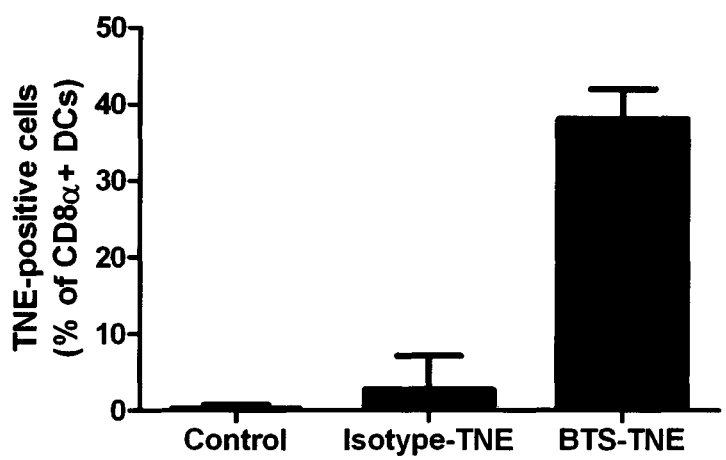
FIG. 10 is a graphical representation of the percentage of $CD8\alpha^+$ dendritic cells bound with backfilled targeted stabilized tailorable nanoemulsion (BTS-TNE) and Isotype-TNE calculated from flow cytometry. The graph shows mean±standard deviation of three experiments.

To test the specificity of BTS-TNE to the ligand-expressing cells, the binding profile of BTS-TNE to the ligand negative cells CHO-K1 and ligand positive cells CHO-K1-Clec9A was determined by CLSM. CHO-K1 and CHO-K1-Clec9A cells were seeded onto 12 mm$^2$ coverslips in 24-well tissue culture plates at a density of $2\times10^5$ cells per well and incubated at 37° C. in a 5% $CO_2$ humidified atmosphere overnight prior to further treatment. BTS-TNE was added to cells at 20-fold dilution and incubated for 1 hour at 4° C. to prevent internalization of bound particles. Unbound BTS-TNE was removed by washing with cold PBS three times. Cells were fixed with 4 w/v % paraformaldehyde for 15 minutes at 4° C. Fixed cells were washed three times with PBS before counter-staining with Alexa 647-conjugated phalloidin (Molecular Probes, Mulgrave, Australia) for cell membrane and DAPI (Molecular Probes, Mulgrave Australia) for nucleus. Coverslips were mounted onto glass slides using DAKO fluorescence mounting medium (DAKO, California, US). Images were acquired on Zeiss Confocal LSM510 META (Carl-Ziess, Sydney, Australia and processed using Zen software.

The CLSM images showed that the binding of BTS-TNE to the ligand-expressing cell line CHO-K1-Clec9A was not hampered by the backfilling of PEG-DAMP4 within the BTS-TNE. Conversely, the presence of additional PEG-DAMP4 within the BTS-TNE system reduced the non-specific binding of BTS-TNE to the ligand-negative cells showing cell specificity and targeting.

The specificity of the established BTS-TNE to ligand expressing cells was further tested using a mixed cell population comprising CHO-K1 and CHO-K1-Clec9A and measured by flow cytometry. CHO-K1-Clec9A was fluorescently labelled with nucleus stain Hoechst 33342 (Molecular Probes, Mulgrave, Aus) before mixing with CHO-K1 at a ratio of 1:1 or 10:1. BTS-TNE was added to the mixed cells at 20-fold dilution and incubated for 1 hour at 4° C. Cells were resuspended in 200 μL of PBS and transferred to flow cytometry tubes, analysed by a Beckman Coulter Gallios™ Flow Cytometer. Flow cytometry data were analysed by Kaluza® software.

Mean fluorescence intensity was calculated from the flow cytometry data. The results are shown in FIG. 7. FIG. 7*a* shows that at 1:1 ratio of CHO-K1 to CHO-K1-Clec9A cells the BTS-TNE showed selectivity for the labelled cells. This selectivity was enhanced when cells were present in a ratio of 10:1 CHO-K1 to CHO-K1-Clec9A cells (FIG. 7*b*).

Example 11

Varying Ratios of Antibody to PEG on the Nanoemulsion

First the target specificity of BTS-TNE containing from 1 to 200 Ab molecules per droplet was tested in a 1:1 mixed CHO-K1 and CHO-Clec9A cell population. The specificity of BTS-TNE was not affected by the variation in Ab molecule to droplet number ratio. Conversely, by significantly increasing the extent of backfilling through increase in the PEG-DAMP4 concentration, the binding of the BTS-TNE with the non-target cells could be significantly down-shifted as shown in FIG. 8.

Example 12

Formation of an S-TNE from a Pre-Formed SEQ ID NO:2-TNE

The potential of SEQ ID NO:2-(DAMP1)-TNE as a starting point for preparing S-TNE was tested. DAMP1-TNE was prepared according to Example 2 and the DAMP1 S-TNE was prepared following the same procedures as detailed in Example 4 except that the lyophilized DAMP1 peptide was used instead of SEQ ID NO:1 (AM1). Stability of the resulting DAMP1 S-TNE was determined by measuring its Z-average size after 100-fold dilution in either PBS or water.

DAMP1-TNE flocculated upon mixing with PBS. However, DAMP1 S-TNE remained stable in water and physiological salt condition (PBS). As shown in FIG. 9, similar DLS Z-averaged size obtained from DAMP1 S-TNE diluted either in water (251.8±6.4 nm) or PBS (241.6±0.7 nm), indicating that the DAMP1 S-TNE also remain stable in salt condition.

Example 13

Formation of an S-TNE from a Pre-Formed DAMP4-TNE

DAMP4-TNE was prepared according to Example 2 using lyophilized DAMP4 peptide and a Z-averaged size distribution of 246.0±1.1 nm was obtained when DAMP4-TNE 1:100 diluted in water. DAMP4-TNE was not stable in PBS. In addition, the attempt of preparing DAMP4-S-TNE was not successful as DAMP4-TNE flocculated upon the mixing with PEGylated DAMP4.

Example 14

BTS-TNE In Vitro Selectivity for Mouse Splenocytes

The in vitro selectivity of the established BTS-TNE was tested using mouse splenocyte. Mice were bred at the Diamantina Institute Biological Research Facility (BRF). The animals were housed in an air-conditioned environment with constant temperature and fed with standard rodent feed under pathogen-free conditions. Spleen was excised from mice and digested with Collagenase Type III (Worthington) at 37° C. for 25 min. Digested tissue was passed through a cell strainer and cells were collected by centrifugation at 800 g for 2 min. Red blood cells were removed by incubation in ACK lysis buffer (0.15 M $NH_4Cl$, 1 mM $KHCO_3$, 0.1 mM $Na_2EDTA$) for 45 s at 37° C. The harvested splenocytes were resuspended in RPMI 1640 media (Sigma) supplemented with 10% FCS at a density of $10^6$ cells per mL. DiI labeled BTS-TNE was prepared according to Example 9. As a control, DiI labeled isotype Ab decorated TNE (Isotype-TNE) was prepared following the same procedure detailed in Example 9, except an isotype Ab-SEQ ID NO:32 (isotype Ab-DAMP4) conjugate was used instead of the Clec9A Ab-DAMP4 conjugate. 1 mL of splenocyte was incubated with 100 μL of BTS-TNE or Isotype-TNE for 1 hr at 4° C.

Splenocytes were washed with fresh RPMI 1640 media supplemented with 10% FCS before staining with I-A/I-E, CD11c and CD8α antibodies. TNE binding level was confirmed by flow cytometry. Clec9A positive dendritic cells (DCs) were gated as I-A/I-E$^{hi}$CD11c$^+$ CD8α$^+$. Flow cytometry data were analyzed by Kaluza® software. FIG. 10 shows the binding of isotype-TNE and BTS-TNE to the CD8α$^+$ DCs after 1 hour incubation. The binding of Clec9A Ab decorated. BTS-TNE to the CD8α$^+$ DCs was 20-fold higher than for the isotype-TNE.

Example 15

In Vivo Selectivity BTS-TNE in Mice

Figure 11:
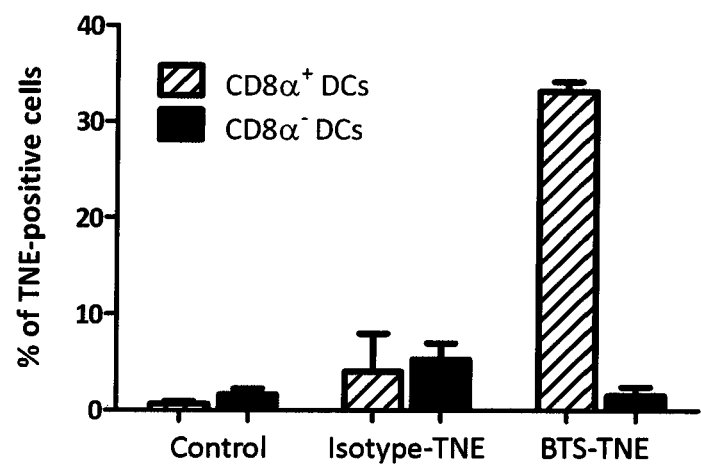
FIG. 11 is a graphical representation of the percentage of $CD8\alpha^+$ and $CD8\alpha^-$ dendritic cells bound with DiI-labelled BTS-TNE or isotype BTS-TNE, calculated from flow cytometry following IP administration into mice and spleen harvest. The graph shows mean±standard deviation of two experiments.

The in vivo uptake of BTS-TNE was tested by injecting DiI-labelled BTS-TNE into mice intraperitoneally. Mice were bred at the Diamantina Institute Biological Research Facility (BRF). The animals were housed in an air-conditioned environment with constant temperature and fed with standard rodent feed under pathogen-free conditions. DiI labeled DAMP4-Clec9A Ab decorated BTS-TNE and a DAMP4-isotype Ab decorated BTS-TNE (isotype-TNE) was prepared as detailed in Example 9. 200 μL of either BTS-TNE or isotype-TNE was injected into mice intraperitoneally. 24 hours post injection, spleen was excised from mice and digested with Collagenase Type III (Worthington) for 25 min at room temperature. Digested tissue was passed through a cell strainer and then centrifuged at 800 g for 2 min before removing red blood cells by incubation in ACK lysis buffer (0.15 M NH$_4$Cl, 1 mM KHCO$_3$, 0.1 mM Na$_2$EDTA) for 45 s at room temperature. Cells were analyzed for TNE uptake by staining with antibodies for I-A/I-E$^{hi}$CD11c$^+$CD8$^+$ cells and then measuring DiI levels by flow cytometry. Flow cytometry data were analyzed by Kaluza® software. Increased percentage of DiI fluorescence positive CD8$^+$ DCs (33.25%) from mice injected with BTS-TNE compared with the one from mice injected with isotype-TNE is shown in FIG. 11 confirms targeted uptake of Clec9A Ab decorated BTS-TNE.

Example 16

In Vivo Cross-Presentation Test

An in vivo cross presentation assay was conducted to test whether the model antigen ovalbumin (OVA) delivered to CD8$^+$ DCs via BTS-TNE was correctly processed through cellular compartments to cross-present to OVA-specific CD8$^+$ OT-I T cells.

To prepare OVA in oil dispersion, 8 mg mL$^{-1}$ of OVA solution was prepared by dissolving 80 mg of OVA (Sigma-Aldrich, St Louis, Mo., USA) in 10 mL of ultrapure water. 1% (w/v) of Cithrol GMO HP solution was prepared by dissolving 200 mg of Cithrol GMO HP in 20 mL hexane. 1 mL of 8 mg mL$^{-1}$ OVA solution and 2 mL of 1% (w/v) Cithrol GMO HP solution were transferred into a 20 mL glass vial, emulsified by using a homogenizer at 24,000 rpm for 5 min. The resulting emulsion was frozen rapidly in dry ice for 2 h before being lyophilized for 24 h. The resulting OVA-Cithrol GMO HP pellet was dissolved in 2 mL of Miglyol 812 and used as oil phase for preparing OVA-BTS-TNE and OVA-Isotype-TNE followed same steps detailed in Example 9.

OT-I T cells (OVA-specific CD8$^+$ T cells) were isolated from spleen and lymph nodes (LNs) of transgenic OT-I mice and purified using Miltenyi CD8α$^+$ T Cell Isolation Kit II (Miltenyi Biotec Australia Pty. Ltd., NSW, Australia). Purified OT-I cells were stained with 5 μM CellTrace™ Violet (CTV) (Molecular Probe, Victoria, Australia) for in vitro tracking.

Figure 12:
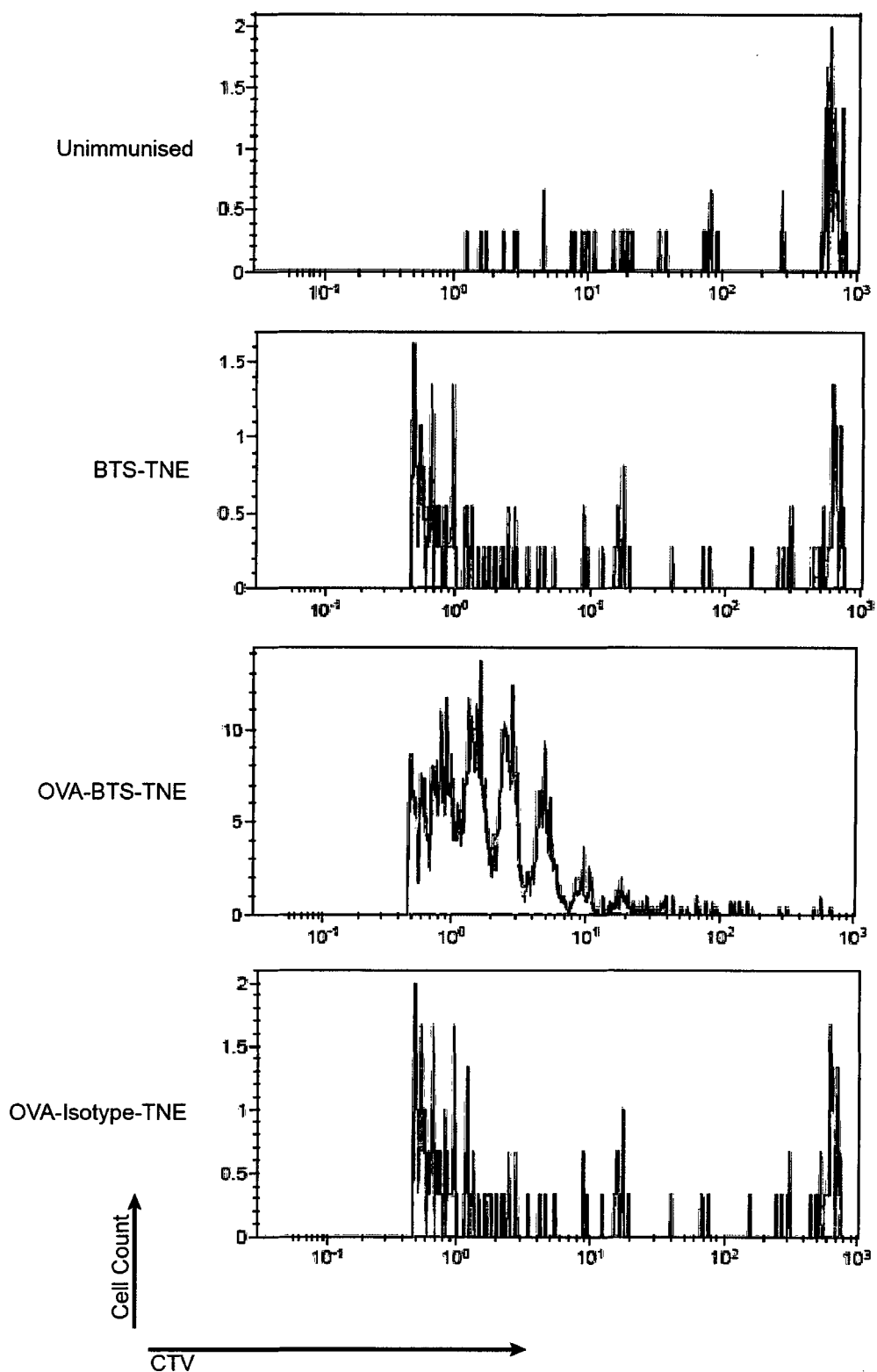
FIG. 12 provides CTV fluorescence histograms of splenic OT-I T cells from mice intravenously immunized with BTS-TNE, OVA-Isotype-TNE or OVA-BTS-TNE (ovalbumin loaded BTS-TNE). Proliferation response of the transferred T cells was determined as the dilution in CTV fluorescence. All profiles obtained were gated on $MHCII^-$ $CD3^+CD8^+$ T cells.

10$^6$ of CTV labelled OT-I cells were adoptively transferred to C57BL/6 mouse one day before immunization. Mice were intravenously immunized with 200 μL of OVA-BTS-TNE, OVA-Isotype-TNE or BTS-TNE. Mice immunized with PBS served as control. Five days later, spleens were excised from mice and single cells suspension was stained with FITC-anti-CD3, PE/Cy7-anti-MHCII and PE-anti-CD8. OT-I T cell proliferation was measured as a function of CTV dilution after gating on MHCII$^-$CD3$^+$CD8$^+$ T cells by flow cytometry. As demonstrated in FIG. 12, immunizing mice with non-targeting OVA-Isotype-TNE failed to induce T cells proliferation, indicating not sufficient antigen was presented to activate T cells response. By contrast, immunizing mice with OVA-BTS-TNE induced noticeable OT-I T cells proliferation, suggesting that the TNE was productively taken up by the target cell population in a receptor-targeted fashion, and its encapsulated antigen was correctly processed by the target cells.

Example 17

In Vivo CTL Assay

Figure 13:
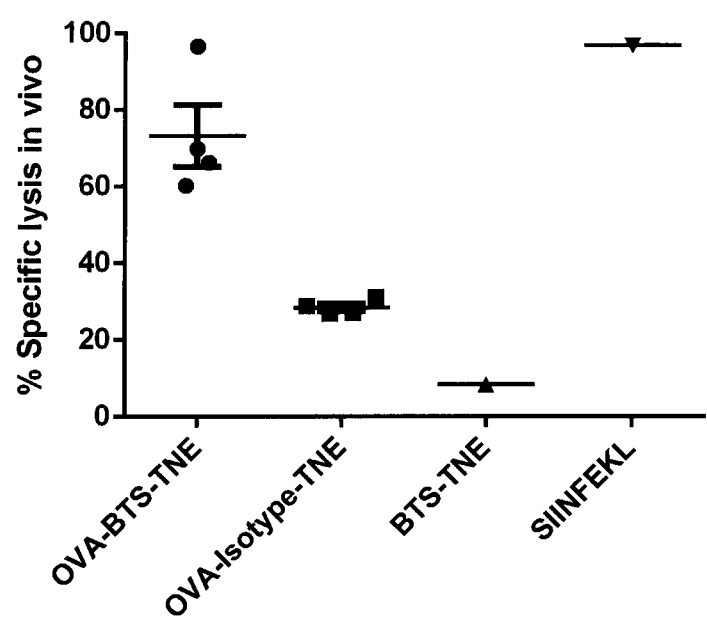
FIG. 13 is a graphical representation of the percentage of OVA peptide SIINFEKL coated splenocytes killed in mice that had been primed with OVA-BTS-TNE, OVA-Isotype-TNE or SIINFEKL. Data shown are mean±SEM, n=1-4 as indicated.

To determine whether targeting antigen to Clec9A leads to endogenous production of effector cytotoxic T-lymphocytes (CTLs), C57BL/6 mice were immunized i.v. with 200 μL of BTS-TNE, OVA-BTS-TNE or OVA-Isotype-TNE. As positive control, a mouse was also immunized with 100 μg of OVA peptide SIINFEKL (SEQ ID NO:67). Five days later, immunized mice were adoptively transferred with CTL target cells. To prepare CTL target cells, single cell suspensions of C57BL/6 mice spleens were depleted of red blood cells and divided into two equal parts. One suspension was pulsed with 10 μg mL$^{-1}$ SIINFEKL for 1 hr at 37° C., washed 3 times and then labelled with 5 μM of CTV (CTV$^{high}$). The other half of the splenocytes suspension was labelled with 0.5 μM of CTV (CTV$^{low}$). Equal number of cells from each population was pooled and 2×10$^7$ cells were adoptively transferred into immunized mice. After 20 h, spleens cells were harvested from mice and analysed by flow cytometry to determine the ratio of CTV$^{high}$ to CTV$^{low}$ target cells. Percentage specific lysis was calculated by [1−(r unprimed/r primed)]×100, where r=% CTV$^{low}$/% CTV$^{high}$ for each mouse. The results are shown in FIG. 13 and show that intravenous injection of OVA-BTS-TNE produced a functional cytotoxic T lymphocyte response.

The invention claimed is:

1. A nanoemulsion comprising an oil phase dispersed in an aqueous phase, at least one peptide surfactant and at least one polypeptide surfactant; wherein:

i) the at least one peptide surfactant comprises the amino acid sequence:

$$X_1\text{-}(abcdd'efg)_n\text{-}X_2$$

wherein n is an integer from 2 to 12;
amino acid residues a and d are hydrophobic amino acid residues;
amino acid residue d' is absent or is a hydrophobic amino acid residue;
at least one of residues b and c and at least one of residues e and f are hydrophilic amino acid residues and the other of amino acid residues b and c and e and f are any amino acid residue;

amino acid residue g is any amino acid residue;
$X_1$ is absent, an N-terminal capping group, or an amino acid residue or a peptide of 2 to 10 amino acid residues optionally capped with an N-terminal capping group; and
$X_2$ is absent, a C-terminal capping group, or an amino acid residue or a peptide of 2 to 10 amino acid residues optionally capped with a C-terminal capping group; and ii) the at least one polypeptide surfactant comprises at least two peptides having α-helical propensity linked by a linking sequence of 3 to 11 amino acid residues, wherein each peptide having α-helical propensity comprises the amino acid sequence:

$$(tuvww'xyz)_m \qquad \text{(II)}$$

wherein m is an integer from 2 to 12;
amino acid residues t and w are hydrophobic amino acid residues;

amino acid residue w' is absent or is a hydrophobic amino acid residue;

at least one of residues u and v and at least one of residues x and y are hydrophilic amino acid residues and the other of amino acid residues u and v and x and y are any amino acid residue; and amino acid residue z is any amino acid residue.

2. A nanoemulsion according to claim 1 wherein the at least one polypeptide surfactant is conjugated to at least one pharmacokinetic modifying agent or at least one targeting agent.

3. A nanoemulsion according to claim 2 wherein the pharmacokinetic modifying agent is polyethylene glycol (PEG).

4. A nanoemulsion according to claim 3 wherein the PEG has a molecular weight in the range of 2000 to 25000 Da.

5. A nanoemulsion according to claim 4 wherein the PEG has a molecular weight of about 5000 Da.

6. A nanoemulsion according to claim 2 wherein the polypeptide surfactant is conjugated to 1 to 5 pharmacokinetic modifying agents.

7. A nanoemulsion according to claim 2 wherein the targeting agent is an antibody or a fragment thereof.

8. A nanoemulsion according to claim 1 wherein the polypeptide surfactant sequence $(t\ u\ v\ w\ w'\ x\ y\ z)_m$ is the same as the peptide surfactant sequence $(a\ b\ c\ d\ d'\ e\ f\ g)_n$.

9. A nanoemulsion according to claim 1 wherein the polypeptide surfactant sequence $(t\ u\ v\ w\ w'\ x\ y\ z)_m$ differs from the peptide surfactant sequence $(a\ b\ c\ d\ d'\ e\ f\ g)_n$ by no more than 10 amino acid residues where any amino acid substitution is a conservative substitution.

10. A nanoemulsion according to claim 2 wherein the polypeptide surfactant is conjugated to at least one pharmacokinetic modifying agent or targeting agent through a linker.

11. A nanoemulsion according to claim 1 comprising one type of peptide surfactant and one type of polypeptide surfactant or one type of peptide surfactant and two types of polypeptide surfactant.

12. A nanoemulsion according to claim 1 comprising more than one type of peptide surfactant.

13. A nanoemulsion according to claim 11 comprising i) a peptide surfactant;

ii) a polypeptide surfactant conjugated to at least one pharmacokinetic modifying agent; and iii) a polypeptide surfactant conjugated to a targeting agent.

14. A nanoemulsion according to claim 1 further comprising a targeting agent that is bound to an entity that is able to associate with the peptide surfactant electrostatically or by coordination or associate with a polypeptide surfactant conjugated to a pharmacokinetic modifying agent before or after the polypeptide surfactant is located at the nanoemulsion liquid-liquid interface.

15. A nanoemulsion according to claim 1 further comprising a coating of an additional polypeptide surfactant of formula (II), wherein said additional polypeptide surfactant is conjugated to a pharmacokinetic modifying agent.

16. A nanoemulsion according to claim 1 further comprising a pharmaceutically active agent.

17. A nanoemulsion according to claim 16 wherein the pharmaceutically active agent is sparingly soluble in aqueous medium.

18. A nanoemulsion according to claim 16 wherein the pharmaceutically active agent is soluble in aqueous medium and is encapsulated in an aqueous droplet in the oil phase or is a solid-in-oil dispersion in the oil phase.

19. A nanoemulsion according to claim 18 wherein the pharmaceutically active agent is a protein antigen.

20. A nanoemulsion according to claim 16 wherein the pharmaceutically active agent is conjugated to a nanoparticle, polymer or dendrimer.

21. A method of preparing a nanoemulsion comprising the steps of:

a) providing an oil phase and an aqueous phase, said aqueous phase comprising a peptide surfactant comprising the amino acid sequence:

$$X_1\text{-}(abcdd'efg)_n\text{-}X_2$$

wherein n is an integer from 2 to 12;

amino acid residues a and d are hydrophobic amino acid residues;

amino acid residue d' is absent or is a hydrophobic amino acid residue;

at least one of residues b and c and at least one of residues e and f are hydrophilic amino acid residues and the other of amino acid residues b and c and e and f are any amino acid residue;

amino acid residue g is any amino acid residue;

$X_1$ is absent, an N-terminal capping group, or an amino acid residue or a peptide of 2 to 10 amino acid residues optionally capped with an N-terminal capping group; and $X_2$ is absent, a C-terminal capping group, or an amino acid residue or a peptide of 2 to 10 amino acid residues optionally capped with a C-terminal capping group;

b) mixing the oil phase and aqueous phase to provide a nanoemulsion;

c) adding a polypeptide surfactant to the nanoemulsion formed in step b); the polypeptide surfactant comprising at least two peptides having α-helical propensity linked by a linking sequence of 3 to 11 amino acid residues, wherein each peptide having α-helical propensity comprises the amino acid sequence:

$$(tuvww'xyz)_m$$

wherein m is an integer from 2 to 12;

amino acid residues t and w are hydrophobic amino acid residues;

amino acid residue w' is absent or is a hydrophobic amino acid residue;

at least one of residues u and v and at least one of residues x and y are hydrophilic amino acid residues and the other of amino acid residues u and v and x and y are any amino acid residue; and amino acid residue z is any amino acid residue;

d) mixing the mixture of step c) to provide a nanoemulsion.

22. A method according to claim 21 comprising the steps of:

a) providing an oil phase and an aqueous phase, said aqueous phase comprising a peptide surfactant comprising the amino acid sequence:

$$X_1\text{-}(abcdd'efg)_n\text{-}X_2$$

wherein n is an integer from 2 to 12;

amino acid residues a and d are hydrophobic amino acid residues;

amino acid residue d' is absent or is a hydrophobic amino acid residue;

at least one of residues b and c and at least one of residues e and f are hydrophilic amino acid residues and the other of amino acid residues b and c and e and f are any amino acid residue;

amino acid residue g is any amino acid residue;

$X_1$ is absent, an N-terminal capping group, or an amino acid residue or a peptide of 2 to 10 amino acid residues optionally capped with an N-terminal capping group; and $X_2$ is absent, a C-terminal capping group, or an amino acid residue or a peptide of 2 to 10 amino acid residues optionally capped with a C-terminal capping group;

b) mixing the composition of step a) to provide a nanoemulsion;

c) adding to the nanoemulsion of step b), a polypeptide surfactant comprising at least two peptides having α-helical propensity linked by a linking sequence of 3 to 11 amino acid residues, wherein each peptide having α-helical propensity comprises the amino acid sequence:

$(tuvww'xyz)_m$ wherein m is an integer from 2 to 12;

amino acid residues t and w are hydrophobic amino acid residues;

amino acid residue w' is absent or is a hydrophobic amino acid residue;

at least one of residues u and v and at least one of residues x and y are hydrophilic amino acid residues and the other of amino acid residues u and v and x and y are any amino acid residue; and amino acid residue z is any amino acid residue, wherein the polypeptide surfactant is conjugated to a pharmacokinetic modifying agent or a targeting moiety;

d) mixing the mixture of step c) to form a stabilized or targeted nanoemulsion.

23. A method according to claim 22 wherein the polypeptide surfactant of step c) is conjugated to a pharmacokinetic modifying agent and the method further comprises the step of:

e) adding an additional polypeptide surfactant of the formula in step c), wherein said additional polypeptide surfactant is conjugated to a targeting agent, to the stabilized nanoemulsion of step d) and mixing the mixture to form a stabilized, targeted nanoemulsion.

24. A method according to claim 22 further comprising the step of:

e) adding an additional polypeptide surfactant of the formula in step c), wherein said additional polypeptide surfactant is conjugated to a pharmacokinetic modifying agent, to the stabilized or targeted nanoemulsion of step d) and mixing the nanoemulsion to provide a coated (backfilled) stabilized nanoemulsion.

25. A method according to claim 23 further comprising the step of:

f) adding an additional polypeptide surfactant of the formula in step c), wherein said additional polypeptide surfactant is conjugated to a pharmacokinetic modifying agent, to the stabilized or targeted nanoemulsion of step d), or to the stabilized, targeted nanoemulsion of step e), and mixing the nanoemulsion to provide a coated (backfilled) nanoemulsion.

* * * * *